US006384203B1

(12) United States Patent
Anderson et al.

(10) Patent No.: US 6,384,203 B1
(45) Date of Patent: May 7, 2002

(54) FAMILY OF IMMUNOREGULATORS DESIGNATED LEUKOCYTE IMMUNOGLOBULIN-LIKE RECEPTORS (LIR)

(75) Inventors: Dirk M. Anderson; Luis G. Borges, both of Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/310,463

(22) Filed: May 12, 1999

(51) Int. Cl.[7] .......................... C07H 21/04; C12N 15/10; C12N 15/11; C12N 15/12; C12N 5/10

(52) U.S. Cl. .................... 536/23.5; 536/23.1; 536/23.4; 435/69.1; 435/91.1; 435/320.1; 435/252.3; 435/325

(58) Field of Search .............................. 536/23.5, 23.1, 536/23.4; 435/69.1, 91.1, 320.1, 325, 252.3

(56) References Cited

FOREIGN PATENT DOCUMENTS

| WO | WO 98/09638 | 3/1998 |
|---|---|---|
| WO | WO 98/24906 | 6/1998 |
| WO | WO 98/31806 | 7/1998 |
| WO | WO 98/48017 | * 10/1998 |

OTHER PUBLICATIONS

Borges, et al. A family of human lymphoid and myeloid Ig–like receptors, some of which bind to MHC Class I molecules. J. Immunol. 159:5192–5196, 1997.*

Allan et al., "Tetrameric complexes of human histocompatibility leukocyte antigen (HLA)–G bind to peripheral blood myelomonocytic cells," *J. Exp. Med.* 189(7):1149–1155, 1999.

Arm et al., "Molecular cloning of gp49, a cell–surface antigen that is preferentially expressed by mouse mast cell progenitors and is a new member of the immunoglobulin superfamily," *J. Biol. Chem.* 266(24):15966–15973, 1991.

Arm et al., "Molecular identification of a novel family of human Ig superfamily members that possess immunoreceptor tyrosine–based inhibition of motifs and homology to the mouse gp49B1 inhibitory receptor," *J. Immunol.* 159(5): 2342–2349, 1997.

Banham et al., "Identification of CD85 antigen as ILT2, an inhibitory MHC class I receptor of the immunoglobulin superfamily," *J. Leukoc. Biol.* 65:841–845, 1999.

Berg et al., "NILR–1, a novel immunoglobulin–like receptor expressed by neutrophilic granulocytes, is encoded by leukocyte gene complex on rat chromosome 1," *Eur. J. Immonol.* 29:2000–2006, 1999.

Biassoni et al., "The human leukocyte antigen (HLA)–C–specific 'activatory' or 'inhibitory' natural killer cell receptors display highly homologous extracellular domain but differ in their transmembrane and intracytoplasmic portions," *J. Exp. Med.* 183:645–650, Feb. 1996.

Bléry et al., "Reconstituted killer cell inhibitory receptors for major histocompatibility complex class 1 molecules control mast cell activation induced via immunoreceptor tyrosine–based activation motifs," *J. Biol. Chem.* 272(14):8989–8996, 1997.

Bléry et al., "The paired Ig–like receptor PIR–B is an inhibitory receptor that recruits the protein–tyrosine phosphatase SHP–1," *Proc. Natl. Acad. Sci. USA* 95:2446–2451, 1998.

Borges et al., "A family of human lymphoid and myeloid Ig–like receptors, some of which bind to MHC class I molecules," *J. Immunol.* 159 (11): 5192–5196, 1997.

Borges et al., "Interactions of LIRs, a family of immunoreceptors expressed in myeloid and lymphoid cells, with viral and cellular MHC class I antigens," *Curr. Top. Microbiol. Immunol.* 244:123–136, 1999.

Brooke et al., "Cloning of two members of the SIRPα family of protein tyrosine phosphatase binding proteins in cattle that are expressed on monocytes and a subpopulation of dendritic cells and which mediate binding to CD4 T cells," *Eur. J. Immunol.* 28:1–11, 1998.

Burshtyn et al., "Recruitment of tyrosine phosphatase HCP by the killer cell inhibitory receptor," *Immunity* 4:77–85, Jan. 1996.

Burshtyn et al., "Conserved residues amino–terminal of cytoplasmic tyrosines contribute to the SHP–1–mediated inhibitory function of killer cell Ig–like receptors," *J. Immunol.* 162:897–902, 1999.

Castells et al., "Cloning of the gp49B gene of the immunoglobulin superfamily and demonstration that one of its two products is an early–expressed mast cell surface protein originally described as gp49," *J. Biol. Chem.* 269(11): 8393–8401, 1994.

Cella et al., "A novel inhibitory receptor (ILT3) expressed on monocytes, macrophages, and dendritic cells involved in antigen processing," *J. Exp. Med.* 185(10):1743–1751, May 1997.

(List continued on next page.)

Primary Examiner—Phillip Gambel
Assistant Examiner—Jessica H. Roark
(74) Attorney, Agent, or Firm—Diana K. Sheiness; Janis C. Henry

(57) ABSTRACT

A new family of immunoreceptor molecules of the immunoglobulin superfamily, (LIR) polypeptides is described. Disclosed are sequences encoding LIR family members and their deduced amino acid sequences, polypeptides encoded by DNA that hybridizes to defined nucleotide sequences, processes for producing polypeptides of the LIR family, and specific antibodies directed against LIR polypeptides. LIR family members can be used to treat autoimmune diseases and disease states associated with suppressed immune function.

18 Claims, No Drawings

OTHER PUBLICATIONS

Chapman et al., "The inhibitory receptor LIR–1 uses a common binding interaction to recognize class I MHC molecules and the viral homolog UL18," *Immunity* 11:603–613, 1999.

Colonna et al., "Cloning of immunoglobulin–superfamily members associated with HLA–C and HLA–B recognition by human natural killer cells," *Science* 268: 405–408, Apr. 1995.

Colonna et al., "Cutting edge: human myelomonocytic cells express an inhibitory receptor for classical and nonclassical MHC class I molecules", *J. Immunol.* 160:3096–3100, 1998.

Colonna et al., "A novel family of Ig–like receptors for HLA class I molecules that modulate function of lymphoid and myeloid cells," *J. Leukoc. Biol.* 66:375–381, 1999.

Colonna et al., "Inhibitory and activating receptors involved in immune surveillance by human NK and myeloid cells," *J. Leukoc. Biol.* 66:718–722, 1999.

Cosman et al., "A novel immunoglobulin superfamily receptor for cellular and viral MHC class I molecules," *Immunity* 7:273–282, 1997.

Cosman et al., "Human cytomegalovirus, MHC class I and inhibitory signalling receptors: more questions than answers," *Immunol. Rev.* 168:177–185, 1999.

Fanger et al., "The MHC class I binding proteins LIR–I and LIR–2 inhibit Fc receptor–mediated signalling in monocytes," *Eur. J. Immunol.* 28:3423–3434, 1998.

Fanger et al., "The leukocyte immunoglobulin–like receptors (LIRs): a new family of immune regulators," *J. Leukoc. Biol.* 66:231–236, 1999.

Fournier et al., "FDF03, a novel Ig–like transmembrane protein with tyrosine–based motifs expressed by human dendritic and myeloid cells," *J. Leukoc. Biol.* (suppl 2):B47, Sep., 1998.

Fry et al., "Phosphotyrosines in the killer cell inhibitory receptor motif of NKB1 are required for negative signaling and for association with protein tyrosine phosphatase 1C," *J. Exp. Med.* 184:295–300, Jul. 1996.

Hayami et al., "Molecular cloning of a novel murine cell–surface glycoprotein homologous to killer cell inhibitory receptors," *J. Biol. Chem.* 272: 7320–7327, Mar. 1997.

Imboden, J. "Innate immunity: Turning off natural killers," *Curr. Biol.* 6 #9:1070–1072, 1996.

Kadowaki et al., "Engagement of new KIR–like receptors KLM promotes maturation of human dendritic cells," *J. Leukoc. Biol.* (suppl 2):B9, Sep., 1998.

Katz et al., "Mouse mast cell gp49B1 contains two immunoreceptor tyrosine–based inhibition motifs and suppresses mast cell activation when coligated with the high–affinity Fc receptor for IgE," *Proc. Natl. Acad. Sci. USA* 93: 10809–10814, Oct. 1996.

Kubagawa et al., "A novel pair of immunoglobulin–like receptors expressed by B cells and myeloid cells," *Proc. Natl. Acad. Sci. USA* 94:5261–5266, May 1997.

Kubagawa et al., "Biochemical nature and cellular distribution of the paired immunoglobulin–like receptors, PIR–A and PIR–B," *J. Exp. Med.* 189(2): 309–317, 1999.

Kuroiwa et al., "Association of tyrosine phosphatases SHP–1 and SHP–2, inositol 5–phosphatase SHIP with gp49B1, and chromosomal assignment of the gene," *J. Biol. Chem.* 273(2):1070–1074, 1998.

Lanier et al., "Inhibitory MHC class I receptors on NK cells and T cells," *Immunol. Today:* Feb. 1996, 17(2):86–91.

Lanier, L., "Natural killer cell receptors and MHC class I interactions," Curr. Opin. Immunol. 9(1):126–131, 1997.

Maeda et al., "Requirement of SH2–containing protein tyrosine phosphatases SHP–1 and SHP–2 for paired immunoglobulin–like receptor B (PIR–B)–mediated inhibitory signal," *J. Exp. Med.* 187(8):1355–1360, 1998.

Maeda et al., "Paired immunoglobulin–like receptor (PIR)–A is involved in activating mast cells through its association with Fc receptor γ chain," *J. Exp. Med.* 188(5):991–995, 1998.

Menaa et al., "Plenary Poster: T082. Upregulated expression of the immunoglobulin–like transcript 3 is required for human osteoclast–like cell formation," *Bone*, vol. 23 (5) (suppl), Nov., 1998.

Moretta et al., "Existence of both inhibitory (p58) and activatory (p50) receptors for HLA–C molecules in human natural killer cells," *J. Exp. Med.* 182:875–884, Sep. 1995.

Nakajima et al., "Cutting Edge: human myeloid cells express an activating ILT receptor (ILT1) that associates with Fc receptor γ–chain," *J. Immunol.* 162:5–8, 1999.

Navarro et al., "The ILT2(LIR1) and CD94/NKG2A NK cell receptors respectively recognize HLA–G1 and HLA–E molecules co–expressed on target cells," *Eur. J. Immunol.* 29:277–283, 1999.

Ponte et al., "Inhibitory receptors sensing HLA–G1 molecules in pregnancy: decidua–associated natural killer cells express LIR–1 and CD94/NKG2A and acquire p49, an HLA–G1–specific receptor," *Proc. Natl. Acad. Sci. USA* 96:5674–5679, 1999.

Rojo et al., "Type I transmembrane receptor with inhibitory function in mouse mast cells and NK cells," *J. Immunol.* 158(1):9–12, 1997.

Samaridis et al., "Cloning of novel immunoglobulin superfamily receptors expressed on human myeloid and lymphoid cells: structural evidence for new stimulatory and inhibitory pathways," *Eur. J. Immunol.* 27:660–665, 1997.

Torkar et al., "Isotypic variation of novel immunoglobulin–like transcript/killer cell inhibitory receptor loci in the leukocyte receptor complex," *Eur. J. Immunol.* 28:3959–3967, 1998.

Yamashita et al., "Inhibitory and stimulatory functions of paired Ig–like receptor (PIR) family in RBL–2H3 cells," *J. Immunol.* 161:4042–4047, 1998.

\* cited by examiner

FAMILY OF IMMUNOREGULATORS DESIGNATED LEUKOCYTE IMMUNOGLOBULIN-LIKE RECEPTORS (LIR)

BACKGROUND OF THE INVENTION

Immune system cellular activity is controlled by a complex network of cell surface interactions and associated signaling processes. When a cell surface receptor is activated by its ligand a signal is sent to the cell, depending upon the signal transduction pathway that is engaged, the signal can be inhibitory or activatory. For many receptor systems cellular activity is regulated by a balance between activatory signals and inhibitory signals. In some of these it is known that positive signals associated with the engagement of a cell surface receptor by its ligand are downmodulated or inhibited by negative signals sent by the engagement of a different cell surface receptor by its ligand.

The biochemical mechanisms of these positive and negative signaling pathways have been studied for a number of known immune system receptor and ligand interactions. Many receptors that mediate positive signaling have cytoplasmic tails containing sites of tyrosine phosphatase phosphorylation known as immunoreceptor tyrosine-based activation motifs (ITAM). A common mechanistic pathway for positive signaling involves the activation of tyrosine kinases which phosphorylate sites on the cytoplasmic domains of the receptors and on other signaling molecules. Once the receptors are phosphorylated, binding sites for signal transduction molecules are created which initiate the signaling pathways and activate the cell. The inhibitory pathways involve receptors having immunoreceptor tyrosine based inhibitory motifs (ITIM) which, like the ITAMs, are phosphorylated by tyrosine kinases. Receptors having these motifs are involved in inhibitory signaling because these motifs provide binding sites for tyrosine phosphatases which block signaling by removing tyrosine from activated receptors or signal transduction molecules. While many of the details of the activation and inhibitory mechanisms are unknown, it is clear that functional balance in the immune system depends upon opposing activatory and inhibitory signals.

One example of immune system activity that is regulated by a balance of positive and negative signaling is B cell proliferation. The B cell antigen receptor is a B cell surface immunoglobulin which, when bound to antigen, mediates a positive signal leading to B cell proliferation. However, B cells also express Fcγ RIIb1, a low affinity IgG receptor. When an antigen is part of an immune complex with soluble immunoglobulin, the immune complex can bind B cells by engaging both the B cell antigen receptor via the antigen and Fcγ RIIb1 via the soluble immunoglobulin. Co-engagement of the Fcγ RIIb1 with the B cell receptor complex downmodulates the activation signal and prevents B cell proliferation. Fcγ RIIb1 receptors contain ITIM motifs which are thought to deliver inhibitory signals to B cells via interaction of the ITIMs with tyrosine phosphatases upon co-engagement with B cell receptors.

The cytolytic activity of Natural Killer (NK) cells is another example of immune system activity which is regulated by a balance between positive signals that initiate cell function and inhibitory signals which prevent the activity. The receptors that activate NK cytotoxic activity are not fully understood. However, if the target cells express cell-surface MHC class I antigens for which the NK cell has a specific receptor, the target cell is protected from NK killing. These specific receptors, known as Killer Inhibitory Receptors (KIRs) send a negative signal when engaged by their MHC ligand, downregulating NK cell cytotoxic activity.

KIRs belong to the immunoglobulin superfamily or the C-type lectin family (see Lanier et al., *Immunology Today* 17:86–91,1996). Known human NK KIRs are members of the immunoglobulin superfamily and display differences and similarities in their extracellular, transmembrane and cytoplasmic regions. A cytoplasmic domain amino acid sequence common to many of the KIRs is an ITIM motif having the sequence YxxL/V. In some cases, it has been shown that phosphorylated ITIMs recruit tyrosine phosphatases which dephosphorylate molecules in the signal transduction pathway and prevent cell activation (see Burshtyn et al., *Immunity* 4:77–85, 1996). The KIRs commonly have two of these motifs spaced apart by 26 amino acids [YxxL/V(x)$_{26}$YxxL/V]. At least two NK cell receptors, each specific for a human leukocyte antigen (HLA) C allele (an MHC class I molecule), exist as an inhibitory and an activatory receptor. These receptors are highly homologous in the extracellular portions, but have major differences in their transmembrane and cytoplasmic portions. One of the differences is the appearance of the ITIM motif in the inhibitory receptor and the lack of the ITIM motif in the activating receptor (see Biassoni et al., *Journal. Exp. Med*, 183:645–650, 1996).

An immunoreceptor expressed by mouse mast cells, gp49B1, also a member of the immunoglobulin superfamily, is known to downregulate cell activation signals and contains a pair of ITIM motifs. gp49B1 shares a high degree of homology with human KIRs (Katz et al., *Cell Biology*, 93: 10809–10814, 1996). Mouse NK cells also express a family of immunoreceptors, the Ly49 family, which contain the ITIM motif and function in a manner similar to human KIRs. However, the Ly49 immunoreceptors have no structural homology with human KIRs and contain an extracellular C-type lectin domain, making them a member of the lectin superfamily of molecules (see Lanier et al., *Immunology Today* 17:86–91, 1996).

Clearly, the immune system activatory and inhibitory signals mediated by opposing kinases and phosphatases are very important for maintaining balance in the immune system. Systems with a predominance of activatory signals will lead to autoimmunity and inflammation. Immune systems with a predominance of inhibitory signals are less able to challenge infected cells or cancer cells. Isolating new activatory or inhibitory receptors is highly desirable for studying the biological signal(s) transduced via the receptor. Additionally, identifying such molecules provides a means of regulating and treating diseased states associated with autoimmunity, inflammation and infection.

For example engaging a newly discovered cell surface receptor having ITIM motifs with an agonistic antibody or ligand can be used to downregulate a cell function in disease states in which the immune system is overactive and excessive inflammation or immunopathology is present. On the other hand, using an antagonistic antibody specific to the receptor or a soluble form of the receptor can be used to block the interaction of the cell surface receptor with the receptor's ligand to activate the specific immune function in disease states associated with suppressed immune function. Conversely, since receptors lacking the ITIM motif send activatory signals once engaged as described above, the effect of antibodies and soluble receptors is the opposite of that just described.

SUMMARY OF THE INVENTION

The present invention provides a new family of immunoreceptor molecules of the immunoglobulin superfamily, designated herein as the Leukocyte Immunoglobulin-Like Receptor (LIR) polypeptides. Within the scope of the present invention are DNA sequences encoding LIR family members and their deduced amino acid sequences disclosed herein. Further included in the present invention are polypeptides encoded by DNA that hybridize to oligonucleotide probes having defined sequences or to DNA or RNA complementary to the probes. The present invention also includes recombinant expression vectors comprising DNA encoding LIR family members. Also within the scope of the present invention are nucleotide sequences which, due to the degeneracy of the genetic code, encode polypeptides that are identical to polypeptides encoded by the nucleic acid sequences described above, and sequences complementary to those nucleotide sequences.

Further, the present invention includes processes for producing polypeptides of the LIR family by culturing host cells transformed with a recombinant expression vector that contains an LIR family member encoding DNA sequence under conditions appropriate for expressing an LIR polypeptide family member, then recovering the expressed LIR polypeptide from the culture.

The invention also provides agonistic and antagonistic antibodies to LIR family proteins.

Further still within the present invention are fusion proteins that include a soluble portion of an LIR family member and the Fc portion of Ig.

Certain autoimmune disorders are associated with the failure of a negative signaling LIR to downregulate cell function. Such disorders may be treated by administering a therapeutically effective amount of an agonistic antibody or ligand of one or more a LIR family member to a patient afflicted with such a disorder. Disorders mediated by disease states associated with suppressed immune function can be treated by administering a soluble form of the negative signaling LIR. Conversely, disorders mediated by diseases associated with failure of a activatory signaling LIR can be treated by administering an agonistic antibody of the activatory receptor. Disorders mediated by states associated with autoimmune function can be treated by administering a soluble form of the activatory receptor.

DETAILED DESCRIPTION OF THE INVENTION

A viral glycoprotein having a sequence similarity to MHC class I antigens has been used to isolate and identify a new polypeptide, designated LIR-P3G2, and several members of a new family of cell surface polypeptides that has been designated the LIR polypeptide family. The present invention encompasses isolated nucleic acid molecules encoding LIR polypeptides, and further encompasses isolated LIR polypeptides. Exemplary nucleic acids encoding LIR polypeptides according to the present invention include those nucleotide sequences shown in SEQ ID NOS:1, 3, 7, 9, 11, 13, 15, 17, 19, 21, 29, 31, 33, 35 and 37, and exemplary LIR polypeptide sequences are shown in SEQ ID NOS:2, 4, 8, 10, 12, 14, 16, 18, 20, 22, 30, 32, 34, 36 and 38.

The LIR polypeptide family members possess extracellular regions having immunoglobulin-like domains, placing the members in a new subfamily of the immunoglobulin superfamily. While the LIR family members are characterized as having very similar extracellular portions, the family includes three groups of polypeptides that are distinguishable by their transmembrane regions and their cytoplasmic regions. One group of the LIR polypeptides has a transmembrane region that includes a positively charged residue and a short cytoplasmic tail and a second group has a nonpolar transmembrane region and a long cytoplasmic tail. A third group includes polypeptides expressed as soluble proteins having no transmembrane region or cytoplasmic tail. One of the LIR proteins has characteristics of both groups one and two, and may represent a fourth group. A number of recent reports have described nucleic acid molecules having sequences related to the LIR family of proteins (Hillier et al., GenBank Accession Number N95687, Apr. 9, 1996; Colonna, M., GenBank Accession Nos. AF041261 and AFo41262, Jan. 7, 1999; Lamerdin et al., GenBank Accession No. AC006293, Jan. 6, 1999; Steffans et al., GenBank Accession Nos. AH007466 and AH007465, Mar. 4, 1999; Cosman et al., *Immunity* 7:273–282 (1997); Borges et al.,*J. Imunol.* 159:5192–96 (1997); Samaridis and Colonna, *Eur. J. Immunol* 27:660–665 (1997); Colonna et al., *J. Exp. Med.* 186:1809–1818 (1997); Wagtmann et al., *Curr. Biol.* 7:615–618 (1997); Rojo et al., *J. Immunol.* 158:9–12 (1997); Arm et al., *J. Immunol.* 159:2342–2349 (1997); Cella et al., *J. Exp. Med.* 185:1743–51 (1997); Torkar et al., *Eur. J. Immunol.* 28:3959–67 (1998); Yamashita et al., *J. Biochem.* 123:358–68 (1998); WO 98/31806; WO 98/24906; WO 98/09638).

The LIR polypeptides encompassed by the subject invention contain at least one Ig-like domain in the extracellular region of the protein, preferably contain either two or four Ig-like domains in the extracellular region. Some LIR polypeptides may contain more than four Ig-like domains. An Ig-like domain is a structural unit that has been identified in a wide variety of cellular proteins. Ig-like domains contain a common fold that forms a sandwich of two β sheets that is stabilized by a characteristic intrachain disulfide bond. Ig-like domains are readily recognizable by reference to a large body of knowledge concerning this structural entity (see, e.g., Williams and Barclay, *Ann. Rev. Immunol.* 6:381–405 (1988)). Typically, Ig-like domains contain about 100 amino acids, although the number of amino acids may vary, e.g., from about 85 to 105 amino acids. Molecules that exhibit Ig-like domains generally play a recognition role at the cell surface, often mediating cell-cell interactions in a variety of biological systems.

LIR-P3G2 (SEQ ID NO:2) is expressed by a variety of cells and recognizes HLA-B44 molecules, HLA-A2 MHC molecules and the alleles described in Example 14. Another LIR family member, designated LIR-pbm8 (SEQ ID NO:9) is expressed by a variety of cells and also recognizes a number of MHC class I molecules. By analogy with known molecules, LIR-P3G2, LIR-pbm8 and LIR members have a role in immune recognition and self/nonself discrimination.

Examples 1–3 below describe isolating cDNA encoding P3G2 (LIR-P3G2) and a substantially identical polypeptide designated 18A3 (LIR-18A3). Briefly, the LIR-P3G2 family member was isolated by first expressing UL18, a Class I MHC-like molecule and using UL18 to isolate and identify P3G2 and 18A3, which are closely related and probably are variants of the same gene, which is designated "LIR-1." The nucleotide sequences of the isolated P3G2 cDNA and 18A3 cDNA are presented in SEQ ID NO:1 and SEQ ID NO:3, respectively. The amino acid sequences encoded by the cDNA presented in SEQ ID NO:1 and SEQ ID NO:3 are presented in SEQ ID NO:2 and SEQ ID NO:4, respectively. The P3G2 amino acid sequence (SEQ ID NO:2) has a predicted extracellular domain of 458 amino acids (1–458) including a signal peptide of 16 amino acids (amino acids 1–16); a transmembrane domain of 25 amino acids (amino acids 459–483) and, a cytoplasmic domain of 167 amino acids (amino acids 484–650). The extracellular domain includes four immunoglobulin-like domains. Ig-like domain I includes approximately amino acids 17–118; Ig-like domain II includes approximately amino acids 119–220; Ig-like domain III includes approximately amino acids 221–318; and Ig-like domain IV includes approximately amino acids 319–419. Significantly, the cytoplasmic domain of this polypeptide includes four ITIM motifs, each having the consensus sequence of YxxL/V. The first ITIM motif pair is found at amino acids 533–536 and 562–565 and the second pair is found at amino acids 614–617 and 644–647. This feature is identical to the ITIM motifs found in KIRs except that KIRs contain only one pair of ITIM motifs.

The 18A3 amino acid sequence (SEQ ID NO:4) has a predicted extracellular region of 459 amino acids (1–459) including a signal peptide of 16 amino acids (amino acids 1–16); a transmembrane domain of 25 amino acids (amino acids 460–484) and a cytoplasmic domain of 168 amino acids (485–652). The 18A3 amino acids sequence (SEQ ID NO:4) is substantially identical to that of P3G2 (SEQ ID NO:2) except that 18A3 has two additional amino acids (at amino acid 438 and 552) and 18A3 possesses an isoleucine residue at amino acid 142 in contrast to a threonine residue for P3G2. Additionally, 18A3 has a serine residue at amino acid 155 and P3G2 has an isoleucine at 155. Finally, the 18A3 polypeptide has a glutamic acid at amino acid 627 and P3G2 has a lysine at 625 which is aligned with the 627 residue of the 18A3 polypeptide. The four ITIM motifs in the 18A3 cytoplasmic domain are at amino acids 534–537 and 564–567 and at 616–619 and 646–649. Glycosylation sites occur at the amino acid triplet Asn-X-Y, where X is any amino acid except Pro and Y is Ser or Thr. Thus, potential glycosylation sites on LIR-P3G2 occur at amino acids 140–142; 281–283; 302–304; and 341–343. Sites on LIR-18A3 are at 281–283; 302–304; and 341–343. The features of these encoded polypeptides are consistent with type I transmembrane glycoproteins.

Examples 8–10 describe isolating and identifying eight additional LIR polypeptide family members by probing cDNA libraries for plasmids that hybridize to a probe obtained from DNA encoding the extracellular region of LIR-P3G2. The nucleotide sequences (cDNA) of the isolated LIR family members are presented in SEQ ID NO:7 (designated pbm25, or LIR-4), SEQ ID NO:9 (designated pbm8, or LIR-2), SEQ ID NO:11 (designated pbm36-2, or LIR-6b), SEQ ID NO:13 (designated pbm36-4, or LIR-6a);. SEQ ID NO:15 (designated pbmhh, or LIR-7); SEQ ID NO:17 (designated pbm2, or LIR-5), SEQ ID NO:19 (designated pbm17, or LIR-3) and SEQ ID NO:21 (designated pbmnew, or LIR-8). The amino acid sequences encoded thereby are presented in SEQ ID NO:8, SEQ ID NO:10, SEQ ID NO:12, SEQ ID NO:14, SEQ ID NO:16, SEQ ID NO: 18, SEQ ID NO: 20 and SEQ ID NO:22, respectively.

Example 15 describes the isolation of LIR-9m1 (SEQ ID NOS:29, 30), LIR-9m2 (SEQ ID NO:31, 32), LIR-9s1 (SEQ ID NO:33, 34), and LIR-9s2 (SEQ ID NO:35, 36), which are four alternatively spliced variants of LIR-9, another new member of the LIR family. The first step in identifying these LIR-9 group of clones was the isolation of a short cDNA clone that was obtained from a human dendritic cell library and whose sequence analysis indicated that it had significant homology with the LIR family, particularly with the sequences shown in SEQ ID NOS:11, 13 and 15. Using PCR primers based on this clone, further cloning efforts yielded four full-length cDNAs corresponding to LIR-9m1, -9m2, -9s1 and -9s2. LIR-9ml and LIR-9m2 are transmembrane proteins that differ by 12 amino acids that are found in the extracellular region of LIR-9m1, but that are absent from LIR9m2. These 12 amino acids correspond to amino acids 29–40 of SEQ ID NO:30. LIRs-9s1 and -9s2 do not contain a transmembrane domain, thus encode soluble versions of LIR-9. The LIR-9s1 polypeptide (SEQ ID NO:34) includes the 12 amino acid insert that is present in LIR-9m1. Amino acids 1–238 of LIR-9s1 (SEQ ID NO:34) and LIR-9m1 (SEQ ID NO:30) are identical, but the remainder of the LIR-9s1 sequence is not identical to the corresponding region of LIR-9m1. Amino acids 1–226 of LIR-9s2 (SEQ ID NO:36) are identical to the first 226 amino acids of LIR-9m2 (SEQ ID NO:32), but the remaining amino acid sequence of LIR-9s2 diverges from that of LIR-9m2.

The same PCR primers that were used to isolate the LIR-9 clones yielded an additional cloned LIR cDNA that has been designated LIR-10 (SEQ ID NOS:37 and 38). By comparing the nucleotide sequence of LIR-10 with the most closely related LIRs that were previously identified, i.e, with SEQ ID NOS:13 and 15, it has been determined that the LIR-10 cDNA is an incomplete clone that lacks sequences located at the 5' end of the corresponding mRNA, including the 5' untranslated region, and nucleotides encoding the first 26 amino acids of the LIR-10 protein.

The identified extracellular, transmembrane and cytoplasmic regions for the polypeptides of LIR family members shown in SEQ ID NOS:10, 12, 14, 16, 18, 20, 22, 30, 32, 34, 36 and 38 are presented below. The polypeptides presented in SEQ ID NOS:8, 34 and 36 are soluble proteins having no transmembrane or cytoplasmic regions. As will be understood by the skilled artisan, the transmembrane region of P3G2 and 18A3 described above and those of LIR polypeptide family members presented below are identified in accordance with conventional criteria for identifying hydrophobic domains associated with such regions. Accordingly, the precise boundaries of any selected transmembrane region may vary from those presented herein. Typically, the transmembrane domain does not vary by more than five amino acids on either end of the domain as described herein. Computer programs known in the art and useful for identifying such hydrophobic regions in proteins are available.

The polypeptide presented in SEQ ID NO:8 (LIR-pbm25) has an extracellular domain that includes the entire amino acid sequence of amino acids 1–439 and a signal peptide of amino acids 1–16. The amino acid sequence presented in SEQ ID NO:10 (LIR-pbm8) has a predicted extracellular region of 458 amino acids (1–458) including a 16 amino acid signal peptide (amino acids 1–16); a transmembrane domain that includes amino acids 459–483; and a cytoplasmic domain that includes amino acids 484–598. The extracellular domain includes four immunoglobulin-like domains and the cytoplasmic domain includes an ITIM motif at amino acids 533–536 and 562–565.

The amino acid sequence presented in SEQ ID NO:12 (LIR-pbm36–2) has a predicted extracellular domain of amino acids including a 16 amino acid signal peptide of from amino acids 1–16; a transmembrane domain which includes amino acids 262–280 and a cytoplasmic domain of from amino acids 281–289. The transmembrane domain includes a charged arginine residue at 264 and the cytoplasmic domain is short, having only a length of only 9 amino acids.

The amino acid sequence presented in SEQ ID NO: 14 (LIR-pbm36-4) has a predicted extracellular domain of amino acids 1–461 including a signal peptide from amino acids 1–16; a transmembrane domain that includes amino acids 462–480 and possesses a charged arginine residue at amino acid 464; and a cytoplasmic domain that includes amino acids 481–489. SEQ ID NO:14 is nearly identical to that of SEQ ID NO:12 except that it possesses four immunoglobulin domains in contrast to the two domains found in the extracellular region of SEQ ID NO:12. The amino acid sequences presented in SEQ ID NO:12 and SEQ ID NO:14 are likely proteins encoded by alternatively spliced transcripts from the same gene.

The amino acid sequence presented in SEQ ID NO:16 (LIR-pbmhh) has a predicted extracellular domain that includes amino acids 1–449 and a signal peptide from amino acids 1–16; a transmembrane domain that includes amino acids 450–468 with a charged arginine residue at amino acid 452; and a cytoplasmic domain that includes amino acids 469–483. The cytoplasmic domain is short with a length of 15 amino acids. The extracellular domain includes four immunoglobulin-like domains.

The amino acid sequence presented in SEQ ID NO:18 (LIR-pbm2) has a predicted extracellular region that includes amino acids 1–259 and a signal peptide of amino acids 1–16; a transmembrane domain that includes amino acids 260–280; and a cytoplasmic domain that includes amino acids 281–448. This LIR family member has cytoplasmic domain which includes an ITIM motif at amino acids 412–415 and 442–445. The extracellular domain includes two immunoglobulin-like domains.

The amino acid sequence presented in SEQ ID NO:20 (LIR-pbm17) has a predicted extracellular domain of amino acids 1–443 that includes a signal peptide of amino acids 1–16; a transmembrane domain which includes amino acids 444–464; and a cytoplasmic domain of amino acids 465–631. The extracellular domain has four immunoglobulin-like domains. SEQ ID NO:20 has two pairs of ITIM YxxL/V motifs in the cytoplasmic domain. A first pair is at amino acids 514–517 and 543–546, and a second pair is at amino acids 595–598 and 625–628.

The amino acid sequence presented in SEQ ID NO:22 (LIR-pbmnew) has a predicted extracellular domain of amino acids 1–456 including a signal peptide of amino acids 1–16; a transmembrane domain which includes amino acids 457–579; and a cytoplasmic domain of amino acids 580–590. The extracellular includes four immunoglobulin-like domains. SEQ ID NO:22 has an ITIM motif at amino acids 554–557 and 584–587.

The LIR-9m1 protein has an extracellular domain located at amino acids 1–262 of SEQ ID NO:30, including a signal peptide at amino acids 1–34 of SEQ ID NO:30. Amino acids 263–284 of SEQ ID NO:30 define the transmembrane region of LIR-9m1, and amino acids 285–299 of SEQ ID NO:30 form the cytoplasmic region. For LIR-9m2, the extracellular region corresponds to amino acids 1–250 of SEQ ID NO:32, including a signal sequence at amino acids 1–35 of SEQ ID NO:32, a transmembrane region at residues 251–272 of SEQ ID NO:32, and a cytoplasmic region at amino acids 273–287 of SEQ ID NO:32. LIR-9s1 (SEQ ID NO:34) and LIR-9s2 (SEQ ID NO:36) consist, respectively, of 265 and 253 amino acids, with their signal sequences being found at amino acids 1–34 of SEQ ID NO:34, and amino acids 1–35 of SEQ ID NO:36.

For LIR-10, amino acids 1–393 of SEQ ID NO:38 correspond to most of the extracellular portion of the LIR-10 protein, though the coding sequences for about 26 amino acids at the amino terminus of this protein, including the signal peptide, are believed to be missing from the LIR-10 cDNA clone that is described herein. The transmembrane region of LIR-10 is defined by amino acids 394–417 of SEQ ID NO:38, and the intracellular region by amino acids 418–449. A single ITIM motif is located at amino acids 438–443 of SEQ ID NO:38.

The amino acid sequences presented in SEQ ID NO: 2, 4, 8, 10, 12, 14, 16, 18, 20, 22, 30, 32, 34, 36 and 38 reveal that the LIR family, with the exception of LIR-10, can be categorized into three groups of polypeptides. One group includes the polypeptides of SEQ ID NOS: 12, 14, 16, 30 and 32, which are distinguishable by a charged arginine residue in their transmembrane regions and their short cytoplasmic regions. A second group includes SEQ ID NO: 2, 4, 10, 18, 20 and 22 which are distinguishable by their hydrophobic cytoplasmic domains and the presence of one or more ITIM motifs in their cytoplasmic regions. A third group includes the polypeptides of SEQ ID NOS: 8, 34 and 36, which are expressed as soluble polypeptides and have no transmembrane or cytoplasmic regions. These soluble polypeptides may function to block the interactions of cell surface family members with their receptors. Alternatively, the soluble polypeptides may act as an activatory signal when bound to the receptor. Like the members of group one, LIR-10 has a relatively short cytoplasmic domain and a charged residue in its transmembrane domain, though its charged residue is histidine instead of arginine. However, LIR-10 also has an ITIM motif in its cytoplasmic domain, like the members of group two. Thus, LIR-10 has some of the characteristics of both groups one and two, and may represent a fourth group of LIR proteins. The LIR polypeptides are characterized generally by the ability of their encoding DNA to hybridize to DNA encoding the P3G2 extracellular region.

The invention should be understood to encompass isolated nucleic acid molecules encoding LIR polypeptides having the amino acid sequences shown in SEQ ID NOS:2, 4, 8, 10, 12, 14, 16, 18, 20, 22, 30, 32, 34, 36 and 38. In one embodiment of the invention, these nucleic acid molecules have the nucleic acid sequences shown in SEQ ID NOS:1, 3, 7, 9, 11, 13, 15, 17, 19, 21, 29, 31, 33, 35 and 37.

The extracellular regions of the LIR family member proteins presented in SEQ ID NO:2, 4, 8, 10, 12, 14, 16, 18, 20, 22, 30, 32, 34, 36 and 38 have a high degree of homology, which varies from 59%–84. Several of the LIR isolates are closely related, thus must represent allelic variants or splicing variants. For example, the extracellular regions of SEQ ID NO:12 and SEQ ID NO:14 share sequence homology which is close to 100%, thus indicating that these polypeptides derive from the same gene. In addition, SEQ ID NOS:2 and 4 share sequence homology that is in excess of 95%, thus probably represent two alleles of the same gene. Moreover, as discussed above, the extracellular regions of SEQ ID NOS:30, 32, 34 and 36 are nearly identical, thus indicting that these four proteins derive from mRNAs that are splicing variants.

While sharing some structural similarities with other members of the immunoglobulin superfamily, the LIR family members have limited homology to other members of the immunoglobulin superfamily. Molecules having the closest structural similarity to the LIRs are the human KIRs and mouse gp49. However, LIR extracellular regions share only a 38–42% identity with the extracellular regions of NKAT3 and p58 Cl-39, respectively. The extracellular regions of the LIR family members are only 35–47% homologous with that of mouse gp49. In contrast, KIRs in general are known to share at least a 80% amino acid identity, with NKAT3 and p58 CL-39 being 81% homologous. Additionally, none of the known KIR molecules has four extracellular immunoglobulin domains which is characteristic of all but two of the known LIR family members. In view of the high sequence homology among the LIR related polypeptides disclosed herein and their relatively low homology with KIRs, the LIR polypeptides are members of a new family of immunoregulators.

An analysis of the amino acid sequences of the LIR polypeptides reveals that specific stretches of amino acids of the LIR polypeptides are highly conserved. One conserved region is a sequence of 46 amino acids found at amino acids 5–50 of SEQ ID NO:2. A data base search determined that the LIR family members differ substantially from the most structurally similar prior art polypeptides in this LIR conserved region. The data base search and structural analysis was performed using BLAST NB1, a local alignment search tool for searching data bases and aligning amino acid sequences to determine identities and variations in a given sequence. The BLAST NB1 software is accessible on the internet at http://www3.ncb1.nlm.nih.gov/entrez/blast. The BLAST NB1 search for sequences having homology to the sequence of amino acids 5 to 50 of SEQ ID NO:2 found that the most structurally similar proteins are FcγIIR, gp49B form 2, and gp49B form 1 having identities with amino acids 5 to 50 of SEQ ID NO:2 of 63%, 67%, and 67% respectively. This contrasts with an LIR family identity with amino acids 5 to 50 of SEQ ID NO:2 which ranges from about 71% to 100%. Specifically, LIR family members of the present invention contain conserved regions near their amino termini having the following identities with amino acids 5–50 of SEQ ID NO:2: SEQ ID NO:8 has a 96% identity; SEQ ID NO: 10 has a 90% identity; SEQ ID NO:12 has a 96% identity; SEQ ID NO:14 has a 91% identity; SEQ ID NO:16 has a 97 % identity; SEQ ID NO:18 has a 77% identity; SEQ ID NO:20 has an 80% identity; SEQ ID NO:22 has an 80% identity; SEQ ID NO:30 has a 78% identity; SEQ ID NO:32 has a 71% identity; SEQ ID NO:34 has a 78% identity; SEQ ID NO:36 has a 71% identity. This conserved region appears to be present also in LIR-10 (SEQ ID NO:38), but is incomplete due to the LIR-10 cDNA clone disclosed herein being truncated at its 5' end.

Sequence identity as used herein is the number of aligned amino acids which are identical, divided by the total number of amino acids in the shorter of the two sequences being compared. A number of computer programs are available commercially for aligning sequences and determining sequence identities and variations. These programs provide identity information based upon the above stated definition of identity. One suitable computer program is the GAP program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides or amino acids, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Another similar program, also available from the University of Wisconsin as part of the GAG computer package for sequence manipulation is the BESTFIT program.

In another aspect, the polypeptides of the present invention have conserved regions which are uniquely characterized as having the amino acid sequence (SEQ ID NO:28): Leu Xaa$_a$ Leu Ser Xaa$_b$ Xaa$_c$ Pro Arg Thr Xaa$_d$ Xaa$_e$ Gln Xaa$_f$ Gly Xaa$_g$ Xaa$_h$ Pro Xaa$_i$ Pro Thr Leu Trp Ala Glu Pro Xaa$_j$ Ser Phe Ile Xaa$_j$ Xaa$_{70}$ Ser Asp Pro Lys Leu Xaa$_k$ Leu Val Xaa$_m$ Thr Gly, where Xaa$_a$ is Gly or Arg; Xaa$_b$ is Leu or Val; Xaa$_c$ is Gly or Asp; Xaa$_d$ is His Arg or Cys; Xaa$_e$ is Val or Met; Xaa$_f$ is Ala or Thr; Xaa$_g$ is His Pro or Thr; Xaa$_h$ Leu Ile or Phe; Xaa$_i$ is Gly Asp or Ala; Xaa$_j$ is Thr Ile Ser or Ala; Xaa$_k$ is Gly or Val; Xaa$_m$ is Met or Ala; and Xaa$_{70}$ is a sequence of 70 amino acids.

As mentioned above, certain LIR family members have ITIM motifs (YxxL/V$_{25-26}$YxxL/V) in their cytoplasmic domains. It is known that many immune regulating receptors such as KIRs, CD22, FcγRIIb1 also have ITIMs in their cytoplasmic domain and function to send inhibitory signals which down regulate or inhibit cell function. It has been shown that these receptors associate with SHP-1 phosphatase via binding to the ITIM motifs. Recruitment of the SHP-1 phosphatase by the receptor appears to be required for intracellular signaling pathways that regulate the inhibitory function of the receptors. The experiment described in Example 11 demonstrates that LIR-P3G2 and LIR-pbm8 polypeptides associate with SHP-1 phosphatase upon phosphorylation and generate inhibitory signals through monocyte activation pathways. It is known that many immune regulating receptors such as KIRs, CD22, FcγRIIb1 have ITIMs in their cytoplasmic domain and function to send inhibitory signals which down regulate or inhibit cell function. Thus, by analogy with KIRs, CD22 and FcγRIIb1, LIR family members presented in SEQ ID NO:2, 4, 10, 18, 20, 22 and 38 that have ITIM motifs deliver an inhibitory signal via the interaction of its ITIM with SHP-1 tyrosine phosphatase, or other tyrosine phosphatases, when the LIR is coligated with an appropriate receptor. Also by analogy with immunoregulatory receptors possessing ITIMs, LIR family members have a regulatory influence on humoral, inflammatory and allergic responses.

The LIR family members presented in SEQ ID NO:12, 14, 16, 30 and 32 have relatively short cytoplasmic domains, have transmembrane regions possessing at least one charged residue, and do not possess the ITIM motif. By analogy with membrane proteins that lack ITIM motifs and have charged transmembrane regions, these family members mediate stimulatory or activatory signals to cells. For example, membrane bound proteins containing a charged residue in the transmembrane regions are known to associate with other membrane-bound proteins that possess cytoplasmic tails having motifs known as immunoreceptor tyrosine-based activation motifs (ITAM). Upon association, the ITAMs become phosphorylated and propagate an activation signal.

The LIR polypeptide designated LIR-P3G2 is expressed on the surface of transfected or normal cells. This is evidenced by the results of the experiments described in Example 3 and Example 5 in which flow cytometry and precipitation techniques demonstrate that LIR-P3G2 is found on monocytes, a subpopulation of NK cells, and B cells. P3G2 was detected on small subset of T cells. P3G2 is expressed as a 110–120 kDa glycoprotein. Since P3G2 has four potential glycosylation sites, the molecular size of this protein will vary with the degree of its glycosylation. Glycosylation sites occur at the amino acid triplet Asn-X-Y, where X is any amino acid except Pro and Y is Ser or Thr. Potential glycosylation sites on P3G2 occur at amino acids 139–141; 280–282; 302–304; and 340–342.

P3G2-LIR isolated as described in Example 3 was tested for its ability to bind to cell surface ligands distinct from UL18. As demonstrated by the experimental results detailed in Example 7, P3G2 binds HLA-B 44 and HLA-A2, class I MHC antigens. Similarly, as demonstrated in Example 14, LIR-P3G2 and LIR-pbm8 bind to a variety of HLA-A, -B, and -C alleles and recognize a broad spectrum of MHC class I specificities. Since Class I MHC molecules play a central role in immune surveillance, self/non-self discrimination, the immune response to infection etc., the LIR-P3G2 and LIR-pbm8 polypeptides have a role in regulation of immune responses. It is known that NK cytolytic activity for killing tumor cells and cells infected with a virus is regulated by a delicate modulation of activatory and inhibitory signals. It has been shown that receptors specific for the same HLA class I molecules to which LIR-P3G2 and LIR-pbm8 bind may be activatory or inhibitory in their triggering mechanism. By analogy, LIR-P3G2 and LIR-pbm8, which bind MHC class I molecules, play a role in balancing immune system cell activity and are useful in treating disease states in which the immune system balance is disrupted.

Within the scope of the present invention are polypeptides which include amino acid sequences encoded by DNA that hybridizes to LIR-P3G2 extracellular DNA probes under moderate to highly stringent conditions as taught herein. Probes that hybridize to DNA that encode polypeptides of the present invention include probes which encompass nucleotides 310–1684 of SEQ ID NO:1 or fragments thereof. Fragments of SEQ ID NO:1 utilized as hybridization probes are preferably greater than 17 nucleotides in length, and more typically are greater than 20 nucleotides in length, and may include nucleotides 358–1684; nucleotides 322–459 (encoding LIR conserved sequence); or DNA or RNA sequences complementary to SEQ ID NOS:5, 6, 23, 24, 27 and 1 or fragments thereof. Fragments of SEQ ID NOS:5, 6, 23, 24 and 27 include these sequences without the restriction sites. The nucleotide sequences described herein also can be used to design PCR primers, for which a convenient length is about 17–30 nucleotides.

Conditions for hybridization may be moderately stringent conditions described in, for example, in Sambrook et al, *Molecular Cloning: A Laboratory Manual*, 2nd ed., Cold Spring Harbor Laboratory Press, 1989, which is hereby incorporated by reference (see, e.g., Vol. 1, pp 1.101–104). Conditions of moderate stringency, as defined by Sambrook et al., include, for example, the use of a prewashing solution containing 5×SSC, 0.5% SDS, 1.0 mM EDTA (pH 8.0) and hybridization conditions of about 55° C. in 5×SSC, incubated overnight. Highly stringent conditions include higher temperatures of hybridization and washing. The skilled artisan will recognize that a given degree of stringency may be maintained while varying the hybridization or wash temperature or composition of the hybridization buffer in accord with formulae known to those in the art (e.g., see Sambrook et al., 9.50–9.51 and 11.45–11.47). Such formulae take into account factors such as the length of the probe, the G+C content of the probe, salt concentration of the hybridization buffer. If desired, formamide may be added to the hybridization buffer, which permits the use of lower hybridization temperatures (e.g., see Sambrook et al., 9.50–9.51).

Preferred embodiments include amino acid sequences encoded by DNA that hybridizes to probes of the extracellular region of LIR-P3G2 having at least 17 nucleotides. Preferred hybridizing conditions include an incubation temperature of 63° C. for 16 hours in a solution of Denhart's solution, 0.05 M TRIS at pH 7.5, 0.9 M NaCl, 0.1% sodium pyrophosphate, 1% SDS and 200 µg/mL salmon sperm DNA, followed by washing with 2×SSC at 63° C. for one hour and then washing with 1×SSC at 63° C. for one hour. However, as explained above, one skilled in the art can devise other hybridization conditions that produce the same degree of stringency. Generally, stringent hybridization conditions involve a combination of buffer and incubation temperature that supports the formation of specific, i.e., well-matched duplexes while still allowing the formation of stable duplexes at an acceptable rate. Conditions of reduced stringency permit the formation of stable duplexes containing a higher degree of mismatched base pairs than can form under more stringent conditions.

Stringent hybridization conditions for PCR primers can be achieved, for example, by hybridizing labeled probes to filter-bound target nucleic acid overnight at 50–55° C. in aqueous buffer containing 5×SSC or 6×SSC (1×SSC=0.15 M NaCl, 0.015 M sodium citrate), followed by washes in 6×SSC at 50–55° C. However, the skilled artisan will recognize that stringent hybridization conditions for oligonucleotide probes will vary, depending on the length, base composition and sequence of the probe (e.g., see Sambrook et al., 11.45–11.49).

The present invention includes polypeptides having amino acid sequences that differ from, but are highly homologous to, those presented in SEQ ID NOS:2, 4, 8, 10, 12, 14, 16, 18, 20, 22, 30, 32, 34, 36 and 38. Examples include, but are not limited to, homologs derived from other mammalian species, variants (both naturally occurring variants and those generated by recombinant DNA technology), and LIR P3G2 and LIR family member fragments that retain a desired biological activity. Preferably, such polypeptides exhibit a biological activity associated with the LIR polypeptides described in SEQ ID NOS:2, 4, 8, 10, 12, 14, 16, 18, 20, 22, 30, 32, 34, 36 and 38, and comprise an amino acid sequence that is at least 80% identical to any of the amino acid sequences of the signal peptide and extracellular domains of the polypeptides presented in SEQ ID NOS:2, 4, 8, 10, 12, 14, 16, 18, 20, 22, 30, 32, 34, 36 and 38. Preferably such polypeptides are at least 90% identical to any of the amino acid sequences of the signal peptide and extracellular domains of the polypeptides presented in SEQ ID NOS: 2, 4, 8, 10, 12, 14, 16, 18, 20, 22, 30, 32, 34, 36 and 38. Determining the degree of identity between polypeptides can be achieved using any algorithms or computer programs designed for analyzing protein sequences. The commercially available GAP program described below is one such program. Other programs include the BESTFIT and GCG programs which are also commercially available.

Within the scope of the present invention are LIR polypeptide fragments that retain a desired biological property of an LIR polypeptide family member such as binding to MHC class I or other ligand. In one such embodiment, LIR polypeptide fragments are soluble LIR polypeptides comprising all or part of the extracellular domain, but lacking the transmembrane region that would cause retention of the polypeptide on a cell membrane. Soluble LIR polypeptides are capable of being secreted from the cells in which they are expressed. Advantageously, a heterologous signal peptide is fused to the N-terminus such that the soluble LIR is secreted upon expression. Soluble LIR polypeptides include extracellular domains incorporating the signal peptide and those in which the signal peptide is cleaved signal peptide.

The use of soluble forms of a LIR family member is advantageous for certain applications. One such advantage is the ease of purifying soluble forms from recombinant host cells. Since the soluble proteins are secreted from the cells, the protein need not be extracted from cells during the recovery process. Additionally, soluble proteins are generally more suitable for intravenous administration and can be used to block the interaction of cell surface LIR family members with their ligands in order to mediate a desirable immune function.

Further encompassed within the present invention are soluble LIR polypeptides, which may include the entire extracellular domain or any desirable fragment thereof, including extracellular domains that exclude signal peptides. Thus, for example, soluble LIR polypeptides include amino acids $x_1$-458 of SEQ ID NO:2, where $x_1$ is amino acids 1 or 17; amino acids $x_2$-459 of SEQ ID NO:4, where $x_2$ is amino acid 1 or 17; amino acids $x_3$-439 of SEQ ID NO:8, where $x_3$ is amino acid 1 or 17; amino acids $x_4$-458 of SEQ ID NO:10, where $x_4$ is amino acid 1 or 17; amino acids $x_5$-241 of SEQ ID NO:12, where amino acid $x_5$ is amino acid 1 or 17; amino acids $x_6$-461 of SEQ ID NO:14, where $x_6$ is amino acid 1 or 17; amino acids $x_7$-449 of SEQ ID NO:16, where $x_7$ is amino acid 1 or 17; amino acids $x_8$-259 of SEQ ID NO:18, where $x_8$ is amino acid 1 or 17; amino acids $x_9$-443 of SEQ ID NO:20, where $x_9$ is amino acid 1 or 17; amino acids $x_{10}$-456 of SEQ ID NO:22, where $x_{10}$ is amino acid 1 or 17; amino acids $x_{11}$-262 of SEQ ID NO:30, where $x_{11}$ is amino acid 1 or 35; amino acids $x_{12}$-250 of SEQ ID NO:32, where $x_{12}$ is amino acid 1 or 36; amino acids $x_{13}$ of SEQ ID NO:34, where $x_{13}$ is amino acid 1 or 35; amino acids $x_{14}$ of SEQ ID NO:36, where $x_{14}$ is amino acid 1 or 36; and amino acids 1–393 of SEQ ID NO:38. The above identified soluble LIR polypeptides include LIR extracellular regions that include and exclude signal peptides. Also encompassed herein are LIRs that lack a transmembrane and cytoplasmic region, such as SEQ ID NOS:8, 34 and 36. Additional soluble LIR polypeptides include fragments of the extracellular domains of family members that retain a desired biological activity, such as binding to ligands that include MHC class I molecules.

LIR family member fragments, including soluble polypeptides, may be prepared by any of a number of conventional techniques. A DNA sequence encoding a desired LIR polypeptide encoding fragment may be subcloned into an expression vector for production of the LIR polypeptide fragment. The selected encoding DNA sequence advantageously is fused to a sequence encoding a suitable leader or signal peptide. The desired LIR member encoding DNA fragment may be chemically synthesized using known DNA synthesis techniques. DNA fragments also may be produced by restriction endonuclease digestion of a full length cloned DNA sequence, and isolated by electrophoresis on an appropriate gel. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

Another technique useful for obtaining a DNA sequence encoding a desired protein fragment is the well-known polymerase chain reaction (PCR) procedure. Oligonucleotides which define the termini of the desired DNA are used as primers to synthesize additional DNA from a desired DNA template. The oligonucleotides may also contain recognition sites for restriction endonucleases, to facilitate inserting the amplified DNA fragment into an expression vector. PCR techniques are described, for example, in Saiki et al., *Science* 239:487(1988): *Recombinant DNA Methodology*, Wu et al., eds., Academic Press, Inc., San Diego (1989), pp. 189–196; and PCR *Protocols: A Guide to Methods and Applications*, Innis et al., eds., Academic Press, Inc. (1990).

The LIR nucleic acid molecules of the present invention include isolated cDNA, chemically synthesized DNA, DNA isolated by PCR, cloned genomic DNA, and combinations thereof. Genomic LIR family DNA may be isolated by hybridization to the LIR family cDNA disclosed herein using standard techniques. Isolated RNA transcribed from LIR family DNA molecules is also encompassed by the present invention.

Within the scope of the present invention are DNA fragments such as LIR polypeptide coding regions and DNA fragments that encode soluble polypeptides. Examples of DNA fragments that encode soluble polypeptides include DNA that encodes entire extracellular regions of LIR family members and DNA that encodes extracellular region fragments such as regions lacking the signal peptide. More specifically, the present invention includes nucleotides 310–2262 of SEQ ID NO:1 (P3G2 coding region); nucleotides $x_1$-1683 of SEQ ID NO:1, where $x_1$ is 310 or 358 (encoding the P3G2 extracellular domain); nucleotides 168–2126 of SEQ ID NO:3 (the 18A3 coding region) and nucleotides $x_2$-1544 of SEQ ID NO:3, where $x_2$ is 168 or 216 (the 18A3 extracellular domain coding region); nucleotides $x_3$-1412 of SEQ ID NO:7, where $x_3$ is 93 or 141 (the pbm25 coding region and extracellular region); nucleotides 184–1980 of SEQ ID NO:9, (the pbm8 coding region) and nucleotides $x_4$-1557 of SEQ ID NO:9, where $x_3$ is 184 or 232 (the pmb8 extracellular domain coding region); nucleotides 171–1040 of SEQ ID NO:11 (pbm36-2 coding region) and nucleotides $x_5$-878 of SEQ ID NO:11, where $x_5$ is 171 or 219 (encoding the pbm36-2 extracellular domain); nucleotides 183–1652 of SEQ ID NO: 13 (coding region for pbm36-4) and nucleotides $x_6$-1565 of SEQ ID NO:13, where $x_6$ is 183 or 231 (encoding the pbm36-4 extracellular domain); nucleotides 40–1491 of SEQ ID NO:15 (the pbmhh coding region) and nucleotides $x_7$-1386 of SEQ ID NO:15, where x7 is 40 or 88 (encoding the pbmhh extracellular domain); nucleotides 30–1376 of SEQ ID NO:17 (the pbm2 coding region) and nucleotides $x_8$-806 of SEQ ID NO:17, where $x_8$ is 30 or 78 (encoding the pbm2 extracellular region); nucleotides 66–1961 of SEQ ID NO:19 (the pbm17 coding region) and nucleotides $x_9$-1394 of SEQ ID NO:19, where $x_9$ is 66 or 114 (encoding the pbm17 extracellular domain); nucleotides 67–1839 of SEQ ID NO:21 (the pbmnew coding region) and nucleotides $x_{10}$-1434 of SEQ ID NO:21, where $x_{10}$ is 67 or 115 (encoding the pbmnew extracellular domain); nucleotides 69–968 of SEQ ID NO:29 (the coding region of LIR-9m1) and nucleotides $x_{11}$-854 of SEQ ID NO:29, where $x_{11}$ is 69 or 170 (encoding the LIR-9m1 extracellular domain); nucleotides 95–958 of SEQ ID NO:31 (the LIR-9m2 coding region) and nucleotides $x_{12}$-844 of SEQ ID NO:31, where $x_{12}$ is 95 or 200 (encoding the LIR-9m2 extracellular domain); nucleotides $x_{13}$-912 of SEQ ID NO:33, where $x_{13}$ is 115 or 216 (the LIR-9s1 coding region and extracellular region); nucleotides $x_{14}$-834 of SEQ ID NO:35, where $x_{14}$ is 73 or 178 (the LIR-9s2 coding region and extracellular region); nucleotides 1–1350 of SEQ ID NO:37 (the LIR-10 coding region) and nucleotides 1–1179 of SEQ ID NO:37 (encoding all but a few amino-terminal amino acids of the LIR-10 extracellular domain).

Included in the present invention are DNAs encoding biologically active fragments of the LIR proteins whose amino acid sequences are presented in SEQ ID NOS:2, 4, 8, 10, 12, 14, 16, 18, 20, 22, 30, 32, 34, 36 and 38.

The present invention encompasses nucleotide sequences which, due to the degeneracy of the genetic code, encode polypeptides that are identical to polypeptides encoded by the nucleic acid sequences described above, and sequences complementary to them. Accordingly, within the present invention are DNA encoding biologically active LIR family members that include the coding region of a native human LIR family member cDNA, or fragments thereof, and DNA that is degenerate as a result of the genetic code to the native LIR polypeptide DNA sequence or the DNA of native LIR family members described herein.

In another aspect, the present invention includes LIR variants and derivatives as well as variants and derivatives of LIR family polypeptides, both recombinant and non-recombinant, that retain a desired biological activity. An LIR variant, as referred to herein, is a polypeptide substantially homologous to a native LIR polypeptide, as described herein, except the variant amino acid sequence differs from that of the native polypeptide because of one or more deletions, insertions or substitutions.

LIR family variants may be obtained from mutations of native LIR nucleotide sequences. Within the present invention are such DNA mutations or variants that include nucleotide sequences having one or more nucleotide additions, nucleotide deletions, or nucleotide substitutions compared to native DNA of LIR family members and that encode variant LIR polypeptides or variant LIR family members having a desired biological activity. Preferably the biological activity is substantially the same as that of the native LIR polypeptide.

Variant amino acid sequences and variant nucleotide sequences of the present invention preferably are at least 80% identical to that of a native LIR family member sequence. One method for determining the degree of homology or identity between a native amino acid or nucleotide sequence and a variant amino acid or nucleotide sequence is to compare the sequences using computer programs available for such purposes. One suitable computer program is the GAP program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Briefly, the GAP program defines identity as the number of aligned symbols (i.e., nucleotides or amino acids) which are identical, divided by the total number of symbols in the shorter of the two sequences being compared. The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of native LIR amino acid sequences may be provided by using any of a number of known techniques. As described above, mutations can be introduced at selected sequence sites by synthesizing oligonucleotides containing a mutant coding sequence, flanked by restriction sites enabling its ligation to fragments of the native sequence. After ligating the synthesized oligonucleotides to the native sequence fragments, the resulting reconstructed nucleotide sequence will encode an analog or variant polypeptide having the desired amino acid insertion, substitution, or deletion. Another procedure suitable for preparing variant polypeptides is oligonucleotide-directed site-specific mutagenesis procedures which provide genes having specific codons altered in accordance with the desired substitution, deletion, or insertion. Techniques for making such alterations include those disclosed in the following references: Walder et al. *Gene,* 42:133, 1986; Bauer et al., *Gene* 37:73, 1985; Craik, *BioTechniques, Jan.* 12–19, 1985; Smith et al. *Genetic Engineering: Principles and Methods*, Plenum Press, 1981; and U.S. Pat. Nos. 4,518,584 and 4,737,462, all of which are incorporated herein by reference.

Variant polypeptides of the present invention may have amino acid sequences which are conservatively substituted, meaning that one or more amino acid residues of a native LIR polypeptide family member is replaced by different residues, such that the variant polypeptide retains a desired biological activity that is essentially equivalent to that of a native LIR family member. In general, a number of approaches to conservative substitutions are well known in the art and can be applied in preparing variant of the present invention. For example, amino acids of the native polypeptide sequence may be substituted for amino acids which do not alter the secondary and/or tertiary structure of the LIR polypeptide. Other suitable substitutions include those which involve amino acids outside of the ligand-binding domain of interest. One approach to conservative amino acid substitutions involves replacing one or amino acids with those having similar physiochemical characteristics, e.g. substituting one aliphatic residue for another such as Ile, Val, Leu, or Ala for one another); substituting one polar residue for another (such as between Lys and Arg; Glu and Asp; or Gln and Asn); or substituting entire regions having similar hydrophobicity or hydrophilic characteristics.

LIR polypeptide variants can be tested for binding to cells as described in Examples 5 and 6 and for phosphatase binding activity as described in Example 11 to confirm biological activity. Other LIR variants within the present invention include polypeptides which are altered by changing the nucleotide sequence encoding the polypeptide so that selected polypeptide Cys residues are deleted or replaced with one or more alternative amino acids. These LIR variants will not form intramolecular disulfide bridges upon renaturation. Naturally occurring LIR polypeptides selected for alteration by deleting or altering Cys residues preferably do not have biological activities which depend upon disulfide bridges formed by the Cys residue. Other possible variants are prepared by techniques which cause the modification of adjacent dibasic amino acid residues to enhance expression in yeast systems in which KEX2 protease activity is present. EP 212,914 discloses site-specific mutagenesis techniques for inactivating KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys and pairings are considerably less susceptible to KEX2 cleavage, and conversion of Arg-Lys or Lys-Arg to Lys-Lys represents a conservative and preferred approach to inactivating KEX2 sites.

Naturally occurring LIR variants are also encompassed by the present invention. Examples of such variants are proteins that result from alternative mRNA splicing events or from proteolytic cleavage of an LIR polypeptide. Alternative splicing of mRNA may yield a truncated but biologically active LIR polypeptide such as a naturally occurring soluble form of the protein. Variations attributable to proteolysis include difference in the N- or C-termini upon expression in different types of host cells, due to proteolytic removal of one or more terminal amino acids from the LIR polypeptide. In addition, proteolytic cleavage may release a soluble form of LIR from a membrane-bound form of the polypeptide. Other naturally occurring LIR variations are those in which differences from the amino acid sequence of SEQ ID Nos:2, 4, 8, 10, 12, 14, 16, 18, 20, 22, 30, 32, 34, 36 and 38 are attributable to genetic polymorphism, the allelic variation among individuals.

Within the scope of the present invention are derivative LIR family polypeptides which include native or variant LIR polypeptides modified to form conjugates with selected chemical moieties. The conjugates can be formed by covalently linking another moiety to a native or variant LIR or by non-covalently linking another moiety to a native or variant LIR. Suitable chemical moieties include but are not limited to glycosyl groups, lipids, phosphates, acetyl groups, and other proteins or fragments thereof. Techniques for covalently linking chemical moieties to proteins are well known in the art and are generally suitable for preparing derivative LIR polypeptides. For example, active or activated functional groups on amino acid side chains can be used as reaction sites for covalently linking a chemical moiety to a LIR polypeptide. Similarly, the N-terminus or C-terminus can provide a reaction site for a chemical moiety. LIR polypeptides or fragments conjugated with other proteins or protein fragments can be prepared in recombinant culture as N-terminal or C-terminal fusion products. For example, the conjugate or fusion portions may include a signal or leader sequence attached to an LIR molecule at its N-terminus. The signal or leader peptide co-translationally or post-translationally directs transfer of the conjugate from its site of synthesis to a site inside or outside of the cell membrane.

One useful LIR polypeptide conjugate is one incorporating a poly-His or the antigenic identification peptides described in U.S. Pat. No. 5,011,912 and in Hopp et al., *Bio/Technology* 6:1124, 1988. For example, the FLAG® peptide, Asp-Tyr-Lys-Asp-Asp-Asp-Asp-Lys (SEQ ID NO:39) is highly antigenic and provides an epitope reversibly bound by a specific monoclonal antibody, thus enabling rapid assay and facile purification of expressed recombinant protein. This sequence is specifically cleaved by bovine mucosal enterokinase at the residue immediately following the Asp-Lys pairing. Fusion proteins capped with this peptide may be resistant to intracellular degradation in *E. coli*. Murine hybridoma designated 4E11 produced a monoclonal antibody that binds the peptide of SEQ ID NO:39 in the presence of certain divalent metal cations, and has been deposited with the American Type Culture Collection under accession no HB9259. Expression systems useful for producing recombinant proteins fused to the FLAG® peptide, and monoclonal antibodies that bind the peptide and are useful in purifying the recombinant proteins, are available from Eastman Kodak Company, Scientific Imaging Systems, New Haven, Conn.

Particularly suitable LIR fusion proteins are those in which an LIR polypeptide is in the form of an oligomer. Oligomers may be formed by disulfide bonds between cysteine residues on more than one LIR polypeptide, or by noncovalent interactions between LIR polypeptide chains. In another approach, LIR oligomers can be formed by joining LIR polypeptides or fragment thereof via covalent or noncovalent interactions between peptide moieties fused to the LIR polypeptide. Suitable peptide moieties include peptide linkers or spacers, or peptides that have the property of promoting oligomerization. Leucine zippers and certain polypeptides derived from antibodies are among the peptides that can promote oligomerization of LIR polypeptides attached thereto.

Other LIR fusion proteins which promote oligomer formation are fusion proteins having heterologous polypeptides fused to various portions of antibody-derived polypeptides (including the Fc domain). Procedures for preparing such fusion proteins are described in Ashkenazi et al. *PNAS USA* 88:10535, 1991; Byrne et al. *Nature* 344:667, 1990, and Hollenbaugh and Aruffo *Current Protocols in Immunology*, Supplement 4, pages 10.19.1–10.19.11, 1992; all of which are incorporated herein by reference. Example 1 and Example 5 below describe methods for preparing UL18:Fc and P3G2:Fc fusion proteins, respectively, by fusing P3G2 and UL18 to an Fc region polypeptide derived from an antibody. This is accomplished by inserting into an expression vector a gene fusion encoding the P3G2:Fc fusion protein and expressing the P3G2:Fc fusion protein. The fusion proteins are allowed to assemble much like antibody molecules, whereupon interchain disulfide bonds form between the Fc polypeptides, yielding divalent P3G2 polypeptide. In a similar approach, P3G2 or any LIR polypeptide may be substituted for the variable portion of an antibody heavy or light chain. If fusion proteins are made with heavy and light chains of an antibody, it is possible to form a LIR oligomer with as many as four LIR regions.

Thus, the invention encompasses nucleic acids that encode fusion proteins that include the Fc region of Ig and an amino acid sequence including the extracellular region of any of the LIR family member proteins. Such extracellular regions include, e.g., amino acids $x_1$-458 of SEQ ID NO:2, where $x_1$ is amino acids 1 or 17; amino acids $x_2$-459 of SEQ ID NO:4, where $x_2$ is amino acid 1 or 17; amino acids $x_3$-439 of SEQ ID NO:8, where $x_3$ is amino acid 1 or 17; amino acids $x_4$-458 of SEQ ID NO:10, where $x_4$ is amino acid 1 or 17; amino acids $x_5$ to 261 of SEQ ID NO:12, wherein $x_5$ is amino acid 1 or 17; amino acids $x_6$ to 461 of SEQ ID NO:14, wherein $x_6$ is amino acid 1 or 17; amino acids $x_7$-449 of SEQ ID NO:16, where $x_7$ is amino acid 1 or 17; amino acids $x_8$-259 of SEQ ID NO:18, where $x_8$ is amino acid 1 or 17; amino acids $x_9$-443 of SEQ ID NO:20, where $x_9$ is amino acid 1 or 17; amino acids $x_{10}$ to 456 of SEQ ID) NO:22, wherein $x_{10}$ is amino acid 1 or 17; amino acids $x_{11}$ to 262 of SEQ ID NO:30, wherein $x_{11}$ is amino acid 1 or 35; amino acids $x_{12}$ to 250 of SEQ ID NO:32, wherein $x_{12}$ is amino acid 1 or 36; amino acids $x_{13}$ to 265 of SEQ ID NO:34, wherein $x_{13}$ is amino acid 1 or 35; and amino acids $x_{14}$ to 253 of SEQ ID NO:36, wherein $x_{14}$ is amino acid 1 or 36; and amino acids 1–393 of SEQ ID NO:38.

As used herein, a Fc polypeptide includes native and mutein forms, as well as truncated Fc polypeptides containing the hinge region that promotes dimerization. One suitable Fc polypeptide is the native Fc region polypeptide derived from a human IgG1, which is described in PCT application WO 93/10151, hereby incorporated herein by reference. Another useful Fc polypeptide is the Fc mutein described in U.S. Pat. No. 5,457,035. The amino acid sequence of the mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

Alternatively, oligomeric LIR polypeptide variants may include two or more LIR peptides joined through peptide linkers. Examples include those peptide linkers described in U.S. Pat. No. 5,073,627, incorporated herein by reference. Fusion proteins which include multiple LIR polypeptides separated by peptide linkers may be produced conventional recombinant DNA technology.

Another method for preparing oligomeric LIR polypeptide variants involves use of a leucine zipper. Leucine zipper domains are peptides that promote oligomerization of the proteins in which they are found. Leucine zippers were first identified in several DNA-binding proteins (Landschulz et al. *Science* 240:1759, 1988). Among the known leucine zippers are naturally occurring peptides and peptide derivatives that dimerize or trimerize. Examples of leucine zipper domains suitable for producing soluble oligomeric LIR polypeptides or oligomeric polypeptides of the LIR family are those described in PCT application WO 94/10308, incorporated herein by reference. Recombinant fusion proteins having a soluble LIR polypeptide fused to a peptide that dimerizes or trimerizes in solution may be expressed in suitable host cells, and the resulting soluble oligomeric LIR polypeptide recovered from the culture supernatant.

Numerous reagents useful for cross-linking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains, thus linking one polypeptide to another.

One type of peptide linker that may be employed in the present invention separates polypeptide domains by a distance sufficient to ensure that each domain properly folds into the secondary and tertiary structures necessary for the desired biological activity. The linker also should allow the extracellular portion to assume the proper spatial orientation to form the binding sites for ligands.

Suitable peptide linkers are known in the art, and may be employed according to conventional techniques. Among the suitable peptide linkers are those described in U.S. Pat. Nos. 4,751,180 and 4,935,233, which are hereby incorporated by reference. A peptide linker may be attached to LIR polypeptides by any of the conventional procedures used to attach one polypeptide to another. The cross-linking reagents available from Pierce Chemical Company as described above are among those that may be employed. Amino acids having side chains reactive with such reagents may be included in the peptide linker, e.g., at the termini thereof. Preferably, a fusion proteins formed via a peptide linker are prepared by recombinant DNA technology.

The fusion proteins of the present invention include constructs in which the C-terminal portion of one protein is fused to the linker which is fused to the N-terminal portion of another protein. Peptides linked in such a manner produce a single protein which retains the desired biological activities. The components of the fusion protein are listed in their order of occurrence (i.e., the N-terminal polypeptide is listed first, followed by the linker and then the C-terminal polypeptide).

A DNA sequence encoding a fusion protein is constructed using recombinant DNA techniques to insert separate DNA fragments encoding the desired proteins into an appropriate expression vector. The 3' end of a DNA fragment encoding one protein is ligated (via the linker) to the 5' end of the DNA fragment encoding another protein with the reading frames of the sequences in phase to permit translation of the mRNA into a single biologically active fusion protein. A DNA sequence encoding an N-terminal signal sequence may be retained on the DNA sequence encoding the N-terminal polypeptide, while stop codons, which would prevent readthrough to the second (C-terminal) DNA sequence, are eliminated. Conversely, a stop codon required to end translation is retained on the second DNA sequence. DNA encoding a signal sequence is preferably removed from the DNA sequence encoding the C-terminal polypeptide.

A DNA sequence encoding a desired polypeptide linker may be inserted between, and in the same reading frame as, the DNA sequences encoding the two proteins using any suitable conventional technique. For example, a chemically synthesized oligonucleotide encoding the linker and containing appropriate restriction endonuclease cleavage sites may be ligated between the sequences encoding Fc and a P3G2 polypeptide.

Within the scope of the present invention are recombinant expression vectors for expressing polypeptides of the LIR family, and host cells transformed with the expression vectors. Expression vectors of the invention include DNA that encodes a LIR family member operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the LIR DNA sequence. Thus, a promoter nucleotide sequence is operably linked to a LIR DNA sequence if the promoter nucleotide sequence controls the transcription of the LIR DNA sequence. An origin of replication that confers the ability to replicate in the desired host cells, and a selection gene by which transformants are identified, are generally incorporated in the expression vector.

In addition, a sequence encoding an appropriate signal peptide can be incorporated into expression vectors. A DNA sequence for a signal peptide (secretory leader) may be fused in frame to the LIR sequence so that the LIR is initially translated as a fusion protein comprising the signal peptide. A signal peptide that is functional in the intended host cells promotes extracellular secretion of the LIR polypeptide. The signal peptide is cleaved from the LIR polypeptide upon secretion of the LIR polypeptide from the cell.

The recombinant expression vectors of the present invention may include any DNA encoding a LIR polypeptide. Exemplary DNAs for inclusion in such expression vectors include the nucleic acid molecules whose sequences are shown in SEQ ID NOS:1, 3, 7, 9, 11, 13, 15, 17, 19, 21, 29, 31, 33, 35 and 37.

Suitable host cells for expression of LIR polypeptides include prokaryotes, yeast or higher eukaryotic cells. Appropriate cloning and expression vectors for use with bacterial, fungal, yeast, and mammalian cellular hosts are described, for example, in Pouwels et al. *Coning Vectors: A Laboratory Manual*, Elsevier, New York, (1985). Cell-free translation systems could also be employed to produce P3G2 polypeptides using RNAs derived from DNA constructs disclosed herein.

Prokaryote host cells suitable in the practice of the present invention include gram negative or gram positive organisms, for example, *E. coli* or Bacilli. Suitable prokaryotic host cells for transformation include, for example, *E. coli, Bacillus subtilis, Salmonella typhimurium*, and various other species such as Pseudomonas, Streptomyces, and Staphylococcus. In a prokaryotic host cell, such as *E. coli*, a P3G2 polypeptide may include an N-terminal methionine residue to facilitate expression of the recombinant polypeptide. The N-terminal Met may be cleaved from the expressed recombinant LIR polypeptide.

Expression vectors for use in prokaryotic host cells generally include one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a LIR family DNA may be inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al. *Nature* 75:615, 1978; and Goeddel et. al., *Nature* 281:544, 1979), tryptophan (trp) promoter system (Goeddel et al., *Nucl. Acids Res.* 8:4057, 1980); and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phase $\lambda P_L$ promoter and a cI857ts thermolabile repressor sequence. Plasmid vectors available from the American Type Culture Collection which incorporate derivatives of the $\lambda P_L$ promoter include plastid pHUB2 (resident in *E. coli* strain JMB9, ATCC 37092) and pPLc28 (resident in *E. coli* RR1, ATCC 53082).

Alternatively, LIR polypeptides may be expressed in yeast host cells, preferably from the Saccharomyces genus (e.g., *S. cerevisiae*). Other genera of yeast, such as Pichia or Kluyveromyces may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem* 255:2073, 1980) or other glycolytic enzymes (Hess et al., *J. Adv. Enzyme Reg.* 7:149, 1968); and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,675. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA from pBR322 for selection and replication in *E. coli* (Amp$^r$ gene and origin of replication) into the above-described yeast vectors.

The yeast a-factor leader sequence may be employed to direct secretion of the LIR polypeptide. The α-factor leader sequence is often inserted between the promoter sequence and the structural gene sequence. See, e.g., Kurjan et al., *Cell* 30:933,1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/mL adenine and 20 μg/mL uracil.

Yeast host cells transformed by vectors containing an ADH2 promoter sequence may be grown for inducing expression in a "rich" medium. An example of a rich medium is one having 1% yeast extract, 2% peptone, and 1% glucose supplemented with 80 μg/mL uracil. Derepression of the ADH2 promoter occurs when glucose is exhausted from the medium.

Mammalian or insect host cell culture systems may be used to express recombinant LIR polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651)(Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CVI/EBNA cell cline derived from the African green monkey cell line CVI (ATCC CCL 70) as described by McMahan et al. (*EMBO J.* 10:2821, 1991). COS-1 (ATCC CRL-1650).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the HIND III site toward the Bg/I site located in the SV40 viral origin of replication site is included.

Suitable expression vectors for use in mammalian host cells can be constructed as disclosed by Okayama and Berg (*Mol. Cell. Biol.* 3:280, 1983). One useful system for stable high level expression of mammalian receptor cDNAs in C127 murine mammary epithelial cells can be constructed substantially as described by Cosman et al. (*Mol. Immunol.* 23:935, 1986). A high expression vector, PMLSV N1/N4, described by Cosman et al., *Nature* 312:768, 1984 has been deposited as ATCC 39890. Additional mammalian expression vectors are described in EP-A-0367566, and in WO 91/18982. Still additional expression vectors for use in mammalian host cells include pDC201 (Sims et al., *Science* 241:585, 1988), pDC302 (Mosley et al. *Cell* 59:335, 1989), and pDC406 (McMahan et al., *EMBO J.* 10:2821, 1991). Vectors derived from retroviruses also may be employed. One preferred expression system employs pDC409 as discussed in Example 5 below.

For expression of LIR polypeptides the expression vector may comprise DNA encoding a signal or leader peptide. In place of the native signal sequence, a heterologous signal sequence may be added, such as the signal sequence for interleukin-7 (IL-7) described in U.S. Pat. No. 4,965,195; the signal sequence for interleukin-2 receptor described in Cosman et al., Nature 312:768, 1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

Further contemplated within the present invention are purified LIR family polypeptides, and processes for their purification. The purified polypeptides of the present invention may be purified from the above-described recombinant expression systems or may be purified from naturally occurring cells. The desired degree of purity may depend on the intended use of the protein with a relatively high degree of purity preferred when the protein is intended for in vivo use. Preferably, LIR polypeptide purification processes are such that no protein bands corresponding to proteins other than the desired LIR protein are detectable by SDS-polyacrylamide gel electrophoresis (SDS-PAGE). It will be recognized by one skilled in the art that multiple bands corresponding to any LIR polypeptide my be detected by SDS-PAGE, due to differential glycosylation, variations in post-translational processing, and the like, as discussed above. Most preferably, any specific LIR polypeptide is purified to substantial homogeneity, as indicated by a single protein band upon analysis by SDS-PAGE. The protein band may be visualized by silver staining, Coomassie blue staining, or by autoradiography or fluorescence if the protein is appropriately labeled.

One process for providing purified LIR polypeptides includes first culturing a host cell transformed with an expression vector comprising a DNA sequence that encodes the desired polypeptide under conditions that promote expressing the desired LIR polypeptide and then recovering the LIR polypeptide. As the skilled artisan will recognize, procedures for recovering the polypeptide will vary according to such factors as the type of host cells employed and whether the polypeptide is secreted in the culture medium is extracted from cells.

When the expression system secretes the polypeptide into the culture medium, the medium may be first concentrated using a commercially available protein concentration filter, for example, an Amicon or Millipore Pellicon ultrafiltration unit. Following the concentration step, the concentrate can be applied to a suitable purification matrix such as a gel filtration medium. Alternatively, an anion exchange resin can be employed, such as a resin matrix or resin substrate having pendant diethylaminoethyl (DEAE) groups. The matrices can be acrylamide, agarose, dextran, cellulose or other types commonly employed in protein purification. Similarly, a purification matrix having cation exchange groups such as sulfopropyl or carboxymethyl functionalities on an insoluble matrix can be used. Sulfopropyl groups are preferred. Still other purification matrices and methods suitable for providing purified LIR are high performance liquid chromatography using hydrophobic reversed phase media (RP-HPLC). One skilled in the art will recognized the any or all of the foregoing purification steps, in various combinations, can be employed to provide a purified LIR polypeptide.

Alternatively, LIR polypeptides can be purified by immunoaffinity chromatography. An affinity column containing an antibody that binds a LIR polypeptide may be prepared by conventional procedures and employed in purifying LIR. Example 5 describes a procedures for generating monoclonal antibodies directed against P3G2 which may be utilized in immunoaffinity chromatography.

Recombinant protein produced in bacterial culture may be isolated by first disrupting the host cells by any convenient method, including freeze-thaw cycling, sonication, mechanical disruption, or use of cell lysing agents and then extracting the polypeptide from cell pellets if the polypeptide is insoluble, or from the supernatant fluid if the polypeptide is soluble. After the initial isolation step, the purification process may include one or more concentrating, salting out, ion exchange, affinity, or size exclusion chromatography purification steps. For many application a final RP-HPLC purification step is beneficial.

Additional methods for providing LIR polypeptides and purified LIR polypeptides involves fermenting yeast which express proteins as a secreted protein. Secreted recombinant protein resulting from a large-scale fermentation can be purified by methods analogous to those disclosed by Urdal et al. (J. Chromatog. 296:171, 1984), involving two sequential, reversed-phase HPLC steps for purification of a recombinant protein on a preparative HPLC column.

LIR-P3G2 DNA in pDC406 vector was deposited with the American Type Culture Collection on Apr. 22, 1997 and assigned accession No.97995. The deposit was made under the terms of the Budapest Treaty.

As described above and shown in Examples 6 and 14, LIR-P3G2 and LIR-pbm8 are MHC class I receptor molecules found on the surface of certain monocytes, B cells, and NK cells. With respect to monocytes, the expression of LIRs that are MHC class I binding proteins suggests that there is some requirement for monocytes to recognize MHC class I molecules. LIR-P3G2, LIR-pbm8 LIR and certain additional LIR family members contain cytoplasmic ITIM motifs. By analogy with the structure and function of known MHC class I receptor molecules, these LIRs are inhibitory receptors mediating negative signaling. Indeed, the results demonstrated in Example 11 reveal that LIRS associate with SHP-1 and inhibit FcR-mediated activation events. Thus, monocytes may express class I receptors in order to suppress cell-mediated lytic mechanisms. Monocytes rapidly phagocytes extracellular pathogens via FcR and, monocyte-FcR engagement induces propagation of immune responses by producing more systemic mediators, particularly TNF-$\alpha$, IL-6 and IL-8. Thus, the LIRs play a role in monocyte and macrophage regulation of cytolytic and inflammatory responses against self tissues. The interplay between the FcR activatory signals and LIR inhibitory signal may allow low levels of self-reactive IgG to exist in circulation and bind to the monocyte membrane with initiating an immune response. For example, the expression of these inhibitory receptors can protect the developing embryo from maternal antibody-mediated allogeneic recognition.

With respect to LIRs on cells of the DC lineage, as described in Example 13 $CD33^+CD14^-CD16^-HLA^-DR^+$ DC co-express LIR-P3G2 and LIR-pbm8. It is suggested the DC FcR play a role in binding immune complexes and triggering DC activation signal following binding. Thus, LIRs expressed on DC may suppress DC activation through interactions of FcR.

Many LIR family members lack the ITIM motif and by analogy with the structure and function of known MHC class I receptors lacking ITIMs are activatory receptors. Failure of a receptor that mediates negative signaling could result in autoimmune diseases. Thus, engaging an LIR family member having ITIM motifs with an agonistic antibody or ligand can be used to downregulate a cell function in disease states in which the immune system is overactive and excessive inflammation or immunopathology is present. On the other hand, using an antagonistic antibody specific to the ITIM possessing LIR receptor or a soluble form of the receptor can be used to block the interaction of the cell surface receptor with the receptor's ligand to activate the specific immune function in disease states associated with suppressed immune function. Since receptors lacking the ITIM motif send activatory signals once engaged as described above, failure of a receptor that mediates an activatory signal could result in suppressed immune function. Engaging the receptor with its agonistic antibody or ligand can be used to treat diseases associated with the suppressed immune function. Using an antagonistic antibody specific to the activatory LIR receptor or a soluble form of the receptor can be used to block the interaction of the activatory receptor with the receptor's ligand to downregulate the activatory signaling.

Since LIR-P3G2 binds to various cells, LIR-P3G2 may be used to purify or isolate these cells from heterogeneous preparations. Additionally, P3G2 probes can be used to isolate and identify related molecules.

LIR polypeptides of the present invention may be used in developing treatments for any disorder mediated directly or indirectly by defective or insufficient amounts of any of the LIR polypeptides. A therapeutically effective amount of purified LIR protein is administered by a patient afflicted with such a disorder. Alternatively, LIR DNA may be employed in developing a gene therapy approach to treating such disorders. Disclosure herein of native LIR nucleotide sequence permits the detection of defective LIR genes, and the replacement thereof with normal LIR-encoding genes. Defective genes may be detected in vitro diagnostic assays, and by comparison of the native LIR nucleotide sequence disclosed herein with that of an LIR gene derived from a person suspected of harboring a defect in the gene.

The present invention also provides pharmaceutical compositions which may include an LIR polypeptide, or fragments or variants thereof with a physiologically acceptable carrier or diluent. Such carriers and diluents will be nontoxic to recipients at the dosages and concentrations employed. Such compositions may further include buffers, antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients commonly used in pharmaceutical compositions. The pharmaceutical compositions of the present invention may be formulated as a lyophilizate using appropriate excipient solutions as diluents. The pharmaceutical compositions may include an LIR polypeptide in any for described herein, including but not limited to active variants, fragments, and oligomers. LIR polypeptides may be formulated according to known methods that are used to prepare pharmaceutically useful compositions. Components that are commonly employed in pharmaceutical formulations include those described in *Remington's Pharmaceutical Sciences,* 16th ed. (Mack Publishing Company, Easton, Pa., 1980).

The pharmaceutical preparations of the present invention may be administered to a patient, preferably a human, in a manner appropriate to the indication. Thus, for example, the compositions can be administered by intravenous injection, local administration, continuous infusion, sustained release from implants, etc. Appropriate dosages and the frequency of administration will depend on such factors as the nature and severity of the indication being treated, the desired response, the condition of the patient and so forth.

In preferred embodiments an LIR polypeptide used in the pharmaceutical compositions of the present invention is purified such that the LIR polypeptide is substantially free of other proteins of natural or endogenous origin, desirably containing less than about 1% by mass of protein contaminants residual of the production processes. Such compositions, however, can contain other proteins added as stabilizers, carriers, excipients or co-therapeutics.

LIR encoding DNAs and DNA fragments disclosed herein find use in the production of LIR polypeptides, as described above. In one embodiment, such fragments comprise at least about 17 consecutive nucleotides, more preferably at least 30 consecutive nucleotides, of LIR DNA. DNA and RNA complements of the fragments have similar utility. Among the uses of LIR nucleic acid fragments are as probes or primers in polymerase chain reactions. For example, a probe corresponding to a fragment of DNA encoding the extracellular domain of LIR may be employed to detect the presence of LIR nucleic acids in in vitro assays and in other probing assays such as Northern Blot and Southern blot assays. Cell types expressing an LIR polypeptide can be identified using LIR family nucleic acid probes using probing procedures well known in the art. Those skilled in the art have the knowledge to choose a probe of suitable length and apply conventional PCR techniques to isolate and amplify a DNA sequence.

Nucleic acid fragments may also be used as a probe in cross species hybridization procedures to isolate LIR DNA from other mammalian species. As one example, a probe corresponding to the extracellular domain of an LIR polypeptide may be employed. The probes may be labeled (e.g., with $^{32}$P) by conventional techniques.

Other useful fragments of LIR nucleic acids are sense or antisense oligonucleotides, which may comprise either RNA or DNA, and which correspond in sequence to an LIR mRNA (sense), to the complement of an LIR mRNA (antisense), or to the non-coding strand of a double-stranded LIR DNA, such as P3G2 DNA (antisense). Thus, an antisense oligonucleotide will form a hybrid duplex with an mRNA sequence. Such oligonucleotides generally are at least 14 nucleotides, and preferably are from about 14 to about 30 nucleotides. The ability to create an antisense or a sense oligonucleotide based upon a cDNA sequence for a given protein is described in, for example, Stein and Cohen, *Cancer Res.* 48:2659, 1988 and van der Krol et al., *BioTechniques* 6:958, 1988.

Binding antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. These oligonucleotides thus may be used to block LIR expression.

In one embodiment antisense or sense LIR oligonucleotides used in binding procedures may encompass oligonucleotides having modified sugar-phosphodiester backbones (or other sugar linkages, such as those described in WO91/06629) and wherein such sugar linkages are resistant to endogenous nucleases. Oligonucleotides having sugar linkages resistant to endogenous nucleases are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. Antisense or sense oligonucleotides are preferably introduced into a cell containing the target nucleic acid sequence by inserting the antisense or sense oligonucleotide into a suitable retroviral vector, then contacting the cell with the retroviral vector containing the inserted sequence, either in vivo or ex vivo. Suitable retroviral vectors include, but are not limited to, those derived from the murine retrovirus M-MuL/V, N2 (a retrovirus derived from M-MuL/V), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugating the ligand binding molecule does not substantially interfere with the ability of the ligand binding molecule to bind its corresponding molecule or receptor, or block entry of the sense of antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In still a further aspect, the present invention provides antibodies that specifically bind LIR polypeptides, i.e., antibodies bind to LIR polypeptides via an antigen-binding site of the antibody (as opposed to non-specific binding). Antibodies of the present invention may be generated using LIR polypeptides or immunogenic fragments thereof. Polyclonal and monoclonal antibodies may be prepared by conventional techniques. See, for example, Monoclonal Antibodies, Hybridomas: A New Dimension in Biological Analyses, Kennet et al. (eds.), Plenum Press, New York 1980; and *Antibodies: A Laboratory Manual*, Harlow and Land (eds.), Cold Spring Harbor Laboratory Press, Cold Spring Harbor, N.Y., 1988. An exemplary procedure for producing monoclonal antibodies immunoreactive with P3G2-LIR is further illustrated in Example 5 below.

Included within the scope of the present invention are antigen binding fragments of antibodies which specifically bind to an LIR polypeptide. Such fragments include, but are not limited to, Fab, F(ab'), and F(ab')$_2$. Antibody variants and derivatives produced by genetic engineering techniques are contemplated as within the presented invention.

The monoclonal antibodies of the present invention include chimeric antibodies, e.g., humanized versions of murine monoclonal antibodies. Such antibodies may be prepared by known techniques and offer the advantage of reduced immunogenicity when the antibodies are administered to humans. In one embodiment a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al., *Nature* 332:232, 1988; Lie et al. *PNAS* 84:3439, 1987; Larrick et al. *Bio/Technology* 7:934, 1989; and Winter and Harris *TIPS* 14:139, 1993.

As mentioned above, antibodies of the present invention are useful in in vitro or in vivo assays to detect the presence of LIR polypeptides and in purifying an LIR polypeptide by affinity chromatography.

Additionally, antibodies capable of blocking an LIR from binding to target cells may be used to inhibit a biological activity of an LIR polypeptide. More specifically, therapeutic compositions of an antibody antagonistic to one or more LIR family members having the ITIM motif may be administered to an individual in order to block the interaction of a cell surface LIR with its ligand. The result is an activation of immune function and is particularly beneficial in disease states in which the immune system is hyporesponsive or suppressed. Conversely, therapeutic compositions of an antibody antagonistic to one or more LIR family members lacking the ITIM motif may be used to obtain the opposite effect and be beneficial in disease states in which the immune system is overactive and excessive inflammation or immunopathology is present.

Pharmaceutical compositions which include at least one antibody that is immunoreactive with an LIR polypeptide and a suitable diluent, excipient, or carrier, are considered with the present invention. Suitable diluents, excipients, and carriers are described in the context of pharmaceutical compositions which include polypeptides of the present invention.

The following examples are provided to illustrate certain embodiments of the invention, and are not to be construed as limiting the scope of the invention.

EXAMPLES

Example 1

Isolating and Expressing Viral Protein

DNA encoding P3G2 polypeptide of the present invention was identified by isolating and expressing a viral glycoprotein, UL18, known to be expressed on cells infected with HCMV, and then expressing and using a UL18/Fc fusion protein to search for UL18 receptors. DNA encoding UL18 and its amino acid sequence are known and described in Beck, S., B. G. Barrell, *Nature* 331:269–272, 1988. The following describes isolating UL18 and preparing the UL18/Fc fusion protein.

Using standard techniques, total RNA was isolated from Human Foreskin Fibroblasts infected with HCMV (AD169) at three different transcription stages-immediate early (IE, 8 p.i.h.), early (24 p.i.h.) and late (48 p.i.h.). Because UL18 is known to be transcribed early in the infection, the IE total RNA was polyA+ selected and used to construct an HCMV-IE cDNA library using a cDNA kit according to the manufacturer's instructions (Pharmacia TIME SAVER cDNA Kit). In order to isolate the full length UL18 gene, two oligonucleotide primers known to include the terminal sequences of the UL18 gene were synthesized and used to isolate and amplify the UL18 gene from the HCMV-IE cDNA library. The primers had the following sequences and included Not I restriction sites which incorporate into the PCR product:

```
              Not 1
5'-TAT GCGGCC GCC ATG ATG ACA ATG TGG T-3'    (SEQ ID NO:23)

5'-TAT GCGGCC GCC CCT TGC GAT AGC G-3'        (SEQ ID NO:24)
       Not 1
```

The PCR conditions included one 5 minute 95° C. cycle followed by 30 cycles of 45 seconds at 95°, 45 seconds at 58° and 45 seconds at 72°, and then one cycle for 5 minutes at 72° C. The PCR product was electrophoresed on a 1% agarose gel and sized using ethidium bromide to visualize the separated DNA products. The presence of DNA of having the expected size of approximately 1.1 kb was confirmed.

The pDC409 expression vector, a vector derived from pDC406 (McMahan et al., *EMBO J.* 10:2821, 1991) but having a single Bgl II site was selected for the cloning process. The PCR product was subcloned into a pDC409 expression vector through the Not I sites, sequenced and the amino acid sequence deduced from the DNA sequence. The determined nucleotide sequence and amino acid sequence were identical to the previously published sequences (ibid.).

A fusion protein of the extracellular region of UL18 and a mutein human IgG1 Fc region (UL18:Fc) was prepared by first isolating cDNA encoding the extracellular region of UL18 using primers which flank the extracellular region of UL18. The primers were synthesized with Sal I and Bgl II restriction sites inserted at the 5' and 3' termini so that the PCR amplified cDNA introduced Sal I and Bgl II restriction sites at the 5' and 3' ends, respectively. The primers had the following sequences:

```
5'-ATA GTCGAC AAC GCC ATG ATG ACA ATG TGG TG-3'   (SEQ ID NO:25)
        SalI

5'-TAA AGATCT GGG CTC GTT AGC TGT CGG GT 3'       (SEQ ID NO:26)
        Bgl II
```

The conditions for the PCR reaction were as described above except that the template was the full length gene isolated as just described.

To prepare a vector construct for expressing fusion protein, sUL18:Fc, for use in cell binding studies, a DNA fragment encoding the Fc region of a human IgG1 antibody was isolated from a plasmid using Bgl II and Not I restriction enzymes. The encoded Fc portion was the mutein Fc described in U.S. Pat. No. 5,457,035 having reduced affinity for immunoglobulin receptors. The Bgl II site on the sUL18 gene was used to ligate the sUL18 gene DNA to the Bgl II site on the Fc gene to form a sUL18:Fc fusion DNA construction having an N-terminal Sal I restriction site and a C-terminal Not I restriction site. This fusion sUL18:Fc DNA construct was then ligated into pDC409 expression vector at its Sal I and Not I sites to form a 409/sUL18/Fc DNA construct.

The monkey cell line COS-1 (ATCC CRL-1650) was used to confirm expression of the fusion protein. COS-1 cells in 6-well plates (2×10$^5$ cells per well) were transfected with about 2 μg of the DNA construct 409/sUL18/Fc per well. The cells were cultured for 2–3 days in 5% FBSDMEM/F12 (available from GIBCO), then washed twice with PBS, starved for 1 hour in cysteine/methionine depleted RPMI (available from GIBCO as RPMI 1640) and metabolically labeled with 100 μCi/mL of $^{35}$S-Met/Cys for 4 hours. The supernatant was spun clear to remove loose cells and 150 μL of the supernatant was incubated with 100 μL of RIPA (0.05% Tween 20, 0.1% SDS, 1% Triton X-100, 0.5% deoxycholate in PBS) buffer and 50 μL of 50% Protein A-Sepharose solid support beads at 4° C. for 1 hour. Protein A-Sepharose is a Sepharose solid support (available from Pharmacia) having immobilized Protein A which binds the Fc portion of the fusion protein. After washing the solid support with RIPA to remove unbound material, fusion protein bound to the Protein A-Sepharose solid support was eluted from the Protein A-Sepharose using 35 μL of SDS-PAGE reducing sample buffer and then heated at 100° C. for 5 minutes. The eluant was then electrophoresed on a 4–20% SDS polyacrylamide gradient gel with $^{14}$C labeled protein molecular weight markers. After electrophoresis the gel was fixed with 8% acetic acid and enhanced at room temperature for 20 minutes with Amplifier available from Amersham. After drying the gel under vacuum it was exposed to x-ray film. Film analysis confirmed that the expected protein, a 100–120 kDa protein which includes the mutein Fc region of IgG and UL18 extracellular domains fused to the Fc, was expressed.

Once cells expressing the fusion protein were identified large scale cultures of transfected cells were grown to accumulate supernatant from cells expressing the fusion protein. This procedure involved transfecting COS-1 cells in T175 flasks with 15 μg of the UL18/Fc/409 fusion DNA per flask. After 7 days of culture in medium containing 0.5% low immunoglobulin bovine serum, a solution of 0.2% azide was added to the supernatant and the supernatant was filtered through a 0.22 μm filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc portion of the sUL18/Fc fusion protein in the supernatant, immobilizing the fusion protein and allowing other components of the supernatant to pass through the column. The column was washed with 30 mL of PBS solution and bound sUL18/Fc was eluted from the HPLC column with citric acid adjusted to pH 3.0. Eluted purified sUL18/Fc was neutralized as it eluted using 1M Hepes solution at pH 7.4. The pooled eluted protein was analyzed using SDS PAGE with silver staining, confirming expression of the 100–120 kDa UL18/Fc fusion protein.

Example 2

Screening Cell Lines for Binding to UL18

The sUL18/Fc protein isolated as described in Example 1 was used to screen cells lines to which it binds using quantitative binding studies according to standard flow cytometry methodologies. For each cell line screened, the procedure involved incubating approximately 100,000 of the cells blocked with 2% FCS (fetal calf serum), 5% normal goat serum and 5% rabbit serum in PBS for 1 hour. Then the blocked cells were incubated with 5 μg/mL of sUL18/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the anti human Fc/biotin to bind to any bound sUL18/Fc and the SAPE to bind to the anti human Fc/biotin resulting in a fluorescent identifying label on sUL18/Fc which is bound to cells. The cells were analyzed for any bound protein using fluorescent detection flow cytometry. The results indicated that UL18 binds well to B cell lines CB23, RAJI and MP-1; monocytic cell lines Thp-1 and U937; and primary B cell and primary monocytes. UL18 does not bind detectably to T cell lines nor does it bind to primary T cells.

Example 3

Isolating a P3G2 cDNA and Polypeptide

The following describes screening cDNA of one of the cell lines found to bind UL18 and the isolation of a novel polypeptide expressed by the cell line. A CB23 cDNA library in the mammalian expression vector pDC406, prepared as described in U.S. Pat. No. 5,350,683 (incorporated herein by reference) was obtained and plasmid DNA was isolated from pools consisting of approximately 2,000 clones per pool. The isolated DNA was transfected into CV1-EBNA cells (ATCC CRL 10478) using DEAE-dextran followed by chloroquine treatment. The CV1-EBNA cells were maintained in complete medium (Dulbecco's modified Eagles' media containing 10% (v/v) fetal calf serum, 50 U/mL penicillin, 50 U/mL streptomycin, and 2 mM L-glutamine) and were plated to a density of approximately $2 \times 10^5$ cells/well in single-well chambered slides. The slides had been pre-treated with 1 mL of a solution of 10 μg/mL human fibronectin in PBS for 30 minutes followed by a single washing with PBS. Media was removed from adherent cells growing in a layer and replaced with 1.5 mL complete medium containing 66.6 μM chloroquine sulfate. About 0.2 mL of a DNA solution (2 μg DNA, 0.5 mg/mL DEAE-dextran in complete medium containing chloroquine) was added to the cells and the mixture was incubated at 37 C. for about five hours. Following incubation, the media was removed and the cells were shocked by addition of complete medium containing 10% DMSO (dimethylsulfoxide) for 2.5 minutes. Shocking was followed by replacing the solution with fresh complete medium. The cells were grown in culture for two to three days to permit transient expression of the inserted DNA sequences. These conditions led to a 30% to 80% transfection frequency in surviving CV1-EBNA cells.

Each slide was incubated with 1 mL of UL18:Fc at a concentration of 1 μg/mL in binding buffer (RPMI 1640 containing 25 mg/mL bovine serum albumin, 2 mg/mL sodium azide, 20 mM Hepes at pH 7.2, and 50 mg/mL nonfat dry milk) at room temperature for 1 hour. The incubated slides were washed with the binding buffer and then incubated with Fc specific $^{125}$I-mouse anti-human IgG (see Goodwin et al., *Cell* 73:447–456, 1993). This was followed by a second wash with buffer after which the slides were fixed with a 2.5% glutaraldehyde/PBS solution, washed with PBS solution and allowed to air dry. The dried slides were dipped in Kodak GTNB-2 photographic emulsion (6× dilution in water). After air drying, the slides were placed in a dark box and refrigerated. After three days the slides were developed in Kodak D19 developer, rinsed in water and fixed in Agfa G433C fixer. The fixed slides were individually examined under a microscope at 25–40× magnification. Positive cells demonstrating binding of sUL18:Fc were visualized by the presence of autoradiographic silver grains against the film background. Two positive pools were identified. Bacterial clones from each pool were titered and plated to provide plates containing approximately 200 colonies each. Each plate was scraped to provide pooled plasmid DNA for transfection into CV1-EBNA cells and screening as described above. Following subsequent breakdowns and screenings, two positive individual colonies were obtained. The cDNA inserts of the two positive clones were 2922 and 2777 nucleotides in length as determined by automated DNA sequences. The coding regions of the two inserts, designated P3G2 and 18A3 were 1953 (nucleotides 310–2262) and 1959 (nucleotides 168–2126) nucleotides, respectively. The two cDNA clones encode proteins that are substantially similar and probably represent different alleles of the same gene.

The cDNA sequence and encoded amino acid of P3G2 are presented in SEQ ID NO: 1 and SEQ ID NO:2, respectively. The cDNA sequence and encoded amino acid of 18A3 are presented in SEQ ID NO:3 and SEQ ID NO:4, respectively. The P3G2 amino acid sequence (SEQ ID NO:2) has a predicted signal peptide of 16 amino acids (amino acids 1–16); an extracellular domain of 442 amino acids. (amino acids 17–458); a transmembrane domain of 25 amino acids (amino acids 459–483) and, a cytoplasmic domain of 167 amino acids (amino acids 484–650. The extracellular domain includes four immunoglobulin-like domains. Ig-like domain I includes approximately amino acids 17–118; Ig-like domain II includes approximately amino acids 119–220; Ig-like domain III includes approximately amino acids 221–318; and Ig-like domain IV includes approximately amino acids 319–419. Significantly, the cytoplasmic domain of this polypeptide includes four ITIM motifs, each having the consensus sequence of YxxL/V. The first ITIM motif pair is found at amino acids 533–536 and 562–565 and the second pair is found at amino acids 614–617 and 644–647. The amino acid sequence of 18A3 is nearly identical having the features describes above.

The features of these encoded polypeptides are consistent with a type I transmembrane glycoprotein.

Example 4

Preparing P3G2 Fusion Protein

The following describes procedures used to generate a P3G2 fusion protein which was then used to identify cell lines to which it binds and finally isolate a normal cell-surface P3G2 ligand which is distinct from UL18. A fusion protein of the extracellular region of P3G2 and the mutein human Fc region (sP3G2:Fc) was prepared by first isolating cDNA encoding the extracellular region of P3G2 using primers which flank the extracellular region of P3G2. The primers were synthesized with Sal I and Bgl II restriction sites inserted at the 5' and 3' termini so that the PCR amplified cDNA introduced Sal I and Bgl II restriction sites at the 5' and 3' ends, respectively. The primers had the following sequences:

```
        Sal I
5'-TAT GTCGAC CAT GAC CCC CAT CCT CAC GGT-3'           (SEQ ID NO:5)

Bgl II    Xa
5'-TAT GGG CTC TGC TCC AGG AGA AGATCTTCCTTCTAT AAC     (SEQ ID NO:6)
    CCC CAG GTG CCT T
```

The conditions for the PCR reaction were as described above and the template was the full length gene P3G2 gene isolated as described in Example 3 above.

To prepare a vector construct for expressing fusion protein sP3G2:Fc for use in cell binding studies, the mutein human Fc region of IgG1 was cut from the plasmid described above in Example 1 using Bgl II and Not I restriction enzymes. The Bgl II site on the sP3G2 gene was used to ligate the sP3G2 gene DNA to the Bgl II site on the human mutein Fc gene to form a sP3G2/Fc fusion DNA construction having an N-terminal Sal I restriction site and a terminal Not I restriction site. This fusion sP3G2:Fc DNA construct was then ligated into pDC409 expression vector at its Sal I and Not I sites to form a 409/sP3G2/Fc DNA construct.

The monkey cell line COS-1 (ATCC CTL-1650) was used to confirm expression of the fusion protein. COS-1 cells in 6-well plates ($2 \times 10^5$ cells per well) were transfected with about 2 μg of the DNA construct 409/sP3G2/Fc per well. The cells were cultured in 5% FBS/DMEM/F12 (available from GIBCO) and at day two or three following transfection, the cells were starved for 1 hour in cysteine/methionine depleted RPMI and the transfected cells were metabolically labeled with 100 μCi/mL of 35S-Met/Cys for 4 hours. The supernatant was spun clear to removed loose cells and debris and 150 μL of the supernatant was incubated with 100 μL of RIPA buffer and 50 μL of 50% Protein A-Sepharose solid support beads at 4° C. for 1 hour. After washing the solid support with RIPA to remove unbound material, fusion protein bound to the Protein A-Sepharose solid support was eluted from the Protein A-Sepharose using 30 μL of SDS-PAGE reducing sample buffer and then heated at 100° C. for 5 minutes. The eluant was then electrophoresed on a 4–20% SDS polyacrylamide gradient gel with $^{14}$C labeled protein molecular weight markers. After electrophoresis the gel was fixed with 8% acetic acid and enhanced at room temperature for 20 minutes with Amplifier available from Amersham. After drying the gel under vacuum it was exposed to x-ray film. Film analysis confirmed that the expected protein, having a molecular weight of 120–130 kDa, was expressed.

Once fusion protein expression was verified, large scale cultures of transfected cells were grown to accumulate supernatant from COS-1 cells expressing the fusion protein as described in Example 1 above. The P3G2/Fc fusion protein was purified according to the procedure described in Example 3 above using the BioCad system and the POROS 20A column from PerSeptive Biosystems. The pooled eluted protein was analyzed using SDS PAGE with silver staining, confirming expression.

Example 5

Generating LIR-P3G2 Antibody

The following example describes generating monoclonal antibody to P3G2 that was used in flow cytometry analysis to identify cells on which P3G2 is expressed. Purified P3G2/Fc fusion protein was prepared by COS-1 cell expression and affinity purification as described in Example 4. The purified protein or cells transfected with an expression vector encoding the full length protein can generate monoclonal antibodies against P3G2 using conventional techniques, for example those techniques described in U.S. Pat. No. 4,411,993. Briefly BALB-C mice were immunized at 0, 2 and 6 weeks with 10 μg P3G2/Fc. The primary immunization was prepared with TITERMAX adjuvant, from Vaxcell, Inc., and subsequent immunization were prepared with incomplete Freund's adjuvant (IFA). At 11 weeks, the mice were IV boosted with 3–4 μg P3G2 in PBS. Three days after the IV boost, splenocytes were harvested and fused with an Ag8.653 myeloma fusion partner using 50% aqueous PEG 1500 solution. Hybridoma supernatants were screened by ELISA using P3G2 transfected COS-1 cells in PBS at $2 \times 10^3$ cells per well and dried to polystyrene 96-well microtiter plates as the platecoat antigen. Positive supernatants were subsequently confirmed by FACS analysis and RIP using P3G2 transfected COS-1 cells. Hybridomas were cloned and followed using the same assays. Monoclonal cultures were expanded and supernatants purified by affinity chromatography using BioRad Protein A agarose.

The monoclonal antibodies to P3G2/Fc were used to screen cells and cell lines using standard flow cytometry procedures to identify cells on which P3G2 is expressed. Cell lines and cells screened in the flow cytometry analyses were CB23, CB39, RAJI, AK778, K299, PS-1, U937, THP-1, JURKAT and HSB2. For each cell line or cell sample screened, the procedure involved incubating approximately 100,000 of the cells blocked with 2% FCS (fetal calf serum), 5% normal Goat serum and 5% rabbit serum in PBS with 5 μg of FITC conjugated mouse anti-P3G2 antibody for 1 hour. Following the incubation the sample was washed 2 times with FACS buffer (2% FCS in PBS). The cells were analyzed for any bound protein using fluorescent detection flow cytometry to detect FITC. The results indicated that LIR-P3G2 antibody binds well to B cell lines CB23 and RAJI1; monocytic cell lines THP-1 and U937; and primary B cell and primary monocytes. The highest expression of LIR-P3G2 was shown on monocytes that stained brightly for CD16 and less brightly for CD14 and CD64. The antibody does not bind detectably to T cell lines nor does it bind detectably to primary T cells.

In a related experiment, the P3G2 antibody generated as described above was used in immunoprecipitation experiments. The immunoprecipitation analyses involved first surface biotinylating $2.5 \times 10^6$ monocytes by washing the cells with PBS and suspending the cells in a biotinylation buffer of 10 mM sodium borate and 150 mM NaCl at pH 8.8, followed by adding 5 μL of a 10 mg/mL solution of biotin-CNHS-ester (D-biotinoyl-e-aminocaproic acid-N-hydroxysuccinimide ester purchased from Amersham) in DMSO to the cells. After quenching the reaction with 10 μL of 1 M ammonium chloride per 1 mL of cells and washing the cells in PBS, the cells were lysed in 1 mL of 0.5% NP40-PBS and the lysate was recovered following centrifugation. Then 100 μL of 0.5% NP40-PBS was added to 150 μL of the lysate and the resulting mixture was incubated with 2 μg/mL of antibody, at 4° C. for 16 hours. Fifty microliters of 50% Protein A-Sepharose slurry was added to the antibody mixture and the slurry was shaken at 4° C. for 1 hour. The slurry was centrifuged and the resulting pellet was washed with 0.75 mL of 0.5% NP40 in PBS six times. Protein bound to the Protein A-Sepharose was eluted with 30 µL of SDS-PAGE reducing sample buffer and heating at 100° C. for five minutes.

The eluted proteins were analyzed using 4–20% gradient SDS-PAGE with enhanced chemiluminescence (ECL) protein markers. Then the electrophoreses samples were transferred in a Western Blot onto nitrocellulose membranes. The membranes were treated with blocking reagent (0.1% Tween-20 and 3% nonfat dry milk in PBS) for one hour at room temperature and then they were washed once for 15 minutes followed and twice for 5 minutes with 0.1% Tween-20 in PBS. The washed membranes were incubated with 10 mL of 1:100 HRP-Streptavidin for 30 minutes and then washed 1 times for 15 minutes followed by 4 times for 5 minutes with 0.1% Tween-20 in PBS.

Bound streptavidin HRP was detected with ECL Detection Reagents purchased from Amersham and used according to manufacturer's instructions. The developed membranes were exposed to x-ray film and then visualized. The results showed that LIR-P3G2 was immunoprecipitated from CB23 cells and P3G2 transfected COS-1 cells, indicating that P3G2 is expressed by these cells.

Example 6

Screening Cells and Cell Lines for Binding to P3G2

The following describes flow cytometry analyses used to identify cells and cell lines which bind to P3G2. The cells and cell lines tested were CB23, HSB2, MP-1, Jurkat, primary T cells, primary B cells, and primary NK cells. For each cell line or cell line tested the procedure involved washing the cells three times with FACS buffer (2% FCS in PBS with 0.2% azide) and incubating each sample ($10^5$ cells) in 100 µL blocking buffer (2% FCS, 5% NGS, 5% rabbit serum in PBS) for one hour. For each cell line 4 test samples were prepared, one each having 0, 2, 5, or 10 µg of W6/32 (ATCC HB-95) in 100 µL blocking buffer added to the samples, respectively. W6/32 is an antibody against MHC Class I heavy chains (an anti HLA-A, B, and C molecule). Following the addition of the W6/32 solution, the samples were incubated on ice for 1 hour and then washed three times with 200 µL of FACS buffer. Then 5 µg of P3G2/Fc in blocking buffer was added to each sample and they were incubated on ice for one hour. The P3G2/Fc competes with W6/32 for binding sites on the cells.

Following the incubation, the cells were washed three times with 200 µL of FACS buffer and treated with mouse anti human Fc/biotin and SAPE for 45 minutes. This treatment causes the anti human Fc/biotin to bind to any cell bound sP3G2/Fc and the SAPE to bind to the anti human F/Biotin. Since the SAPE is a fluorescing compound its detection using appropriate excitation and emission conditions positively identifies cell bound P3G2/Fc. Finally the treated cells were washed three times with FACS buffer and subjected to flow cytometry to identify cells bound to protein.

The results demonstrated that W6/32 competed with P3G2 for binding to all cells and cell lines tested. The P3G2 binding was totally blocked at 5 µg W6/32 indicating that W6/32 and P3G2 are binding to the same or overlapping sites on the MHC Class I heavy chains.

Example 7

Screening HSB2 cDNA Library to Isolate a P3G2 Binding Ligand

The following describes screening a cDNA library from of one of the cell lines, HSB-2, a T lymphoblastic leukemia cell line, found to bind P3G2, and identifying a P3G2 binding ligand. An HSB2 cDNA library in the mammalian expression vector pDC302, was prepared as generally described in U.S. Pat. No. 5,516,658 and specifically in Kozlosky et al. *Oncogene* 10.299–306, 1995. Briefly, mRNA was isolated from sorted HSB-2 cells and a first cDNA strand was synthesized using 5 µg polyA$^+$ and the reverse transcriptase AMV RTase from Life Science. The second cDNA strand was synthesized using DNA polymerase I from BRL at concentration of 1.5 U/µL. Using standard techniques as described in Haymerle et al., *Nucl. Acids Res.* 14:8615, 1986, the cDNA was ligated into the appropriate site of the pDC302 vector.

*E. coli.* strain DH5α cells were transformed with the cDNA library in pDC302. After amplifying the library a titer check indicated that there was a total of 157,200 clones. The transformed cells were plated into 15 different plates. Plasmid DNA was isolated from pools consisting of approximately 2,000 clones per pool. The isolated DNA was transfected into CV1-EBNA cells (ATCC CRL 10478) using DEAE-dextran followed by chloroquine treatment. The CV1-EBNA cells were maintained in complete medium (Dulbecco's modified Eagles' media containing 10% (v/v) fetal calf serum, 50 U/mL penicillin, 50 U/mL streptomycin, and 2 mM L-glutamine) and were plated to a density of approximately $2 \times 10^5$ cells/well in single-well chambered slides. The slides had been pre-treated with 1 mL of a solution of 10 µg/mL human fibronectin in PBS for 30 minutes followed by a single washing with PBS. Media was removed from adherent cells growing in a layer and replaced with 1.5 mL complete medium containing 66.6 µM chloroquine sulfate. About 0.2 mL of a DNA solution (2 µg DNA, 0.5 mg/mL DEAE-dextran in complete medium containing chloroquine) was added to the cells and mixture was incubated at 37 C. for about five hours. Following incubation media was removed and the cells were shocked by adding complete medium containing 10% DMSO for 2.5 minutes. After shocking the cells the complete medium was replaced with fresh complete medium and the cells were grown in culture for three days to permit transient expression of the inserted DNA sequences. These conditions led to a 30% to 80% transfection frequency in surviving CV1-EBNA cells.

Each slide was incubated with 1 mL of P3G2:Fc at a concentration of 0.45 µg/mL in binding buffer (RPMI 1640 containing 25 mg/mL bovine serum albumin, 2 mg/mL sodium azide, 20 mM Hepes at pH 7.2, and 50 mg/mL nonfat dry milk) at room temperature for 1 hour. After incubating the slides, they were washed with binding buffer and then incubated with Fc specific $^{125}$I-mouse anti-human IgG (see Goodwin et al. *Cell* 73:447–456, 1993). This was followed by a second wash with buffer after which the slides were fixed with a 2.5% glutaraldehyde/PBS solution, washed in PBS and allowed to air dry. The slides were dipped in Kodak GTNB-2 photographic emulsion (6× dilution in water). After air drying the slides were placed in a dark box and refrigerated. After three days the slides were developed in Kodak D19 developer, rinsed in water and fixed in Agfa G433C fixer. The fixed slides were individually examined under a microscope at 25–40× magnification. Positive pools demonstrating binding of sP3G2:Fc were visualized by the presence of autoradiographic silver grains against the film background. Two positive pools were titered and plated to provide plates containing approximately 200 colonies each. Each plate was scraped to provide pooled plasmid DNA for transfection into CV1-EBNA cells and screening as described above. Following subsequent breakdowns and screenings, one positive individual colony was obtained for each pool. The cDNA insert of the positive clones were identified as HLA-B44 and HLA-A2, class I MHC antigens.

Example 8

Northern Blot Analysis

Since the experiments described in Example 4 resulted in the detection of LIR-P3G2 surface expression on a number of cell lines, conventional Northern Blot analysis procedures were used to study the expression of LIR-P3G2 and any LIR-P3G2 related mRNAs in different tissue types. The cell lines selected for Northern Blot analysis were RAJI, PBT, PBM, YT, HEP3B, HELA, KB, KG-1, IMTLH, HPT, HFF, THP-1, and U937. The following describes the Northern Blot analysis and the analysis results.

The cDNA encoding the extracellular region of P3G2 was isolated using primers which flank the extracellular region of P3G2 and having the following sequences:

```
      Sal I
5'-TAT GTCGAC CAT GAC CCC CAT CCT CAC GGT 3'     (SEQ ID NO:5)

Bgl II
5'-TAT AGATCT ACC CCC AGG TGC CTT CCC AGA CCA    (SEQ ID NO:27)
```

The PCR template was the full length P3G2 gene isolated as described in Example 3 above. The conditions for the PCR reaction were as follows: One cycle at 95° C. for 5 minutes; 30 cycles which included 95° C. for 45 seconds, 64° C. for 45 seconds and 72° C. for 45 seconds; and, one cycle at 72° C. for 5 minutes. The PCR product was cloned into PCR II vector, purchased from Invitrogen, in accordance with the supplier's instructions. The isolated DNA encoding the extracellular region of P3G2 was used to make a riboprobe with the Ambion MAXISCRIPT Kit according to the manufacturer's instructions.

Northern blots containing poly A+ selected RNA or total RNA from a variety of human cell lines were prepared by resolving RNA samples on a 1.1% agarose-formaldehyde gel, blotting onto Hybond-N as recommended by the manufacturer (Amersham Corporation) and staining with methylene blue to monitor RNA concentrations. The blots were prepared using 1 μg of the PolyA+ RNA or 10 μg of total RNA and each blot was probed with $10^6$ cpm/mL RNA extracellular P3G2 riboprobe, prepared as just described, at 63° C. for 16 hours. The probed blots were washed with 2×SSC at 63° C. for 30 minutes 2 times; 1×SSC at 63° C. for 30 minutes 2 times; and, 0.1×SSC at 63° C. for 5 minutes 2 times.

The probed blots were autoradiographically developed. The developed blots showed that the P3G2 RNA hybridized to a 3.5 kb RNA expressed by RAJI, CB23 and U937; an approximately 1.5 kb RNA expressed by THP-1; and multiple RNAs ranging from 1.5 kb to 3.5 kb expressed by PBM. These results suggest that different genes having extracellular domains similar in structure to that of P3G2 may be expressed by peripheral blood monocytes.

Example 9

Probing PBM cDNA Library to Isolate LIR Polypeptides

The following describes steps taken to screen a peripheral blood monocyte cDNA library to isolate polypeptides relating to the P3G2 polypeptide using conventional Southern Blot methodologies. A peripheral blood monocyte cDNA library was prepared using substantially the same procedures described in Example 7.

DNA from an initial 15 pools of cDNA having 10,000 clones per pool was digested with Bgl II restriction enzyme and electrophoresed on a 1% agarose gel at 100 V for 2 hours. Southern Blots were prepared by electroblotting the electrophoresed DNA in 0.55% TBE buffer onto Hybond membranes. The blotted DNA was denatured in 0.5 M NaOH in 0.6M NaCl solution for 5 minutes and then neutralized in 0.5 M TRIS in 1.5 M NaCl at pH 7.8 for 5 minutes. The membranes were placed in a STRATALINKER UV crosslinker for 20 seconds to crosslink the blotted DNA to the membrane. The membrane and bound DNA were placed in pre-hybridization solution of 10×Denhart's Solution, 0.05M TRIS at pH 7.5, 0.9M NaCl, 0.1% sodium pyrophosphate, 1% SDS and 200 μg/mL salmon sperm DNA at 63° C. for 2 hours and then the bound DNA was probed with $^{32}$P labeled probe of DNA encoding the extracellular region of LIR-P3G2, including the signal peptide and Sal I and Bgl II restriction sites. The concentration of the DNA probe in hybridization solution was $10^6$ CPM per mL of hybridization solution. The probed blots were incubated for 16 hours at 63° C. and then washed with 2×SSC at 63° C. for 1 hour with one solution change; 1× with SSC at 63° C. for one hour with one solution change; and, with 0.1×SSC at 68° C. for 45 minutes with one solution change. After drying the blots they were autoradiographically developed and visualized for DNA bands which hybridized to the P3G2 extracellular DNA probe.

The results of the autoradiography visualization indicated that all pools contained DNA which hybridized to the probe. One pool showing 7 positive DNA bands was selected and subsequently subdivided to 10 pools having 3,000 clones per pool. Applying subsequent Southern Blotting methodologies to the 10 pools resulted in one pool showing 9 positively hybridizing DNA sequences. Single hybridizing clones were isolated by standard colony hybridization techniques.

Duplicate bacterial colonies on filters were probed with the P3G2 extracellular probe described above at a concentration of 500,000 cpm/mL at 63° C. for 16 hours. The hybridized filters were washed with 2×SSC at 63° C. for 30 minutes; with 1×SSC at 63° C. for 30 minutes; and finally with 0.1×SSC at 68° C. for 15 minutes.

Forty-eight clones were visualized as hybridizing on duplicate filters by autoradiography and DNA obtained from these clones using standard DNA preparation methodologies was digested with Bgl II. Then Southern Blots of the digests were obtained and probed with the P3G2 extracellular probe described above. Seven different sized cloned inserts were identified as positively hybridizing to the P3G2 probe. The nucleotide sequence of each of the inserts was obtained using automated sequencing technology. Of the 8 different cloned inserts, one was identical in sequence to LIR-P3G2. The others were identified as DNA encoding polypeptides of the new LIR family of polypeptides. The nucleotide sequences (cDNA) of the isolated LIR family members are resented in SEQ ID NO:7 (designated pbm25), SEQ ID NO:9 (designated pbm8), SEQ D NO:11 (designated pbm36-2), SEQ ID NO: 13 (designated pbm36-4); SEQ ID NO:15 (designated pbmhh); SEQ ID NO:17 (designated pbm2) and SEQ ID NO:19 (designated pbm17). The amino acid sequences encoded thereby are presented in SEQ ID NO:8 (designated pbm25), SEQ ID NO:10 (designated pbm8), SEQ ID NO:12 (designated pbm36-2), SEQ ID NO:14 (designated pbm36-4), SEQ ID NO:16 (designated pbmhh); SEQ ID NO:18 (designated pbm2); and SEQ ID NO:20 (designated pbm17).

Example 10

Screening a Human Dendritic Cell cDNA Library for LIR cDNA Sequences

The following describes the isolation and identification of an LIR family member by screening a human bone marrow-derived dendritic cell cDNA library in the λ Zap vector with a radiolabeled Hh0779 cDNA fragment. The Hh0779 cDNA fragment is a 0.7kb insert of the Hh0779 clone previously isolated from a human dendritic cell cDNA library and obtained by restriction digestion with the enzymes PstI and SpeI. The Hh0779 cDNA fragment was labeled with [a-$^{32}$P] dCTP using the DECAprime II DNA labeling kit purchased from Ambion.

The λ Zap cDNA library was plated at a density of 20,000 pfu per plate to provide a total of 480,000 plagues for the initial screening. The λ Zap cDNA was blotted in duplicate onto Hybond membranes, purchased from Amersham, and then denatured in a solution of 0.5N NaOH and 0.5M NaCl for 5 minutes. The membranes were neutralized in a solution of 0.5M Tris (pH 7.8) and 1.5M NaCl for 5 minutes, and then washed in 2×SSC for 3 minutes. The cDNA was crosslinked to the Hybond membranes using a STRATALINKER UV crosslinker in the auto setting.

The membranes were pre-hybridized at 65° C. for 2.25 hours in hybridization buffer containing 10×Denhardt's, 0.05M Tris (pH 7.5), 0.9M NaCl, 0.1% sodium pyrophosphate, 1% SDS and 4 mg/mL heat denatured salmon sperm DNA. After the pre-hybridization, the radio-labeled Hh0779 cDNA was added to the hybridization buffer to a final concentration of 0.54×10$^6$ cpm/mL. After 24 hours of hybridization, the membranes were washed in 0.25×SSC, 0.25% SDS at 65° C. for 1.5 hours. The blots were then exposed to autoradiographic film to visual positive clones.

A total of 146 positive clones showing hybridization signals in both membranes of a duplicate set were identified, isolated, and saved for future use. Of the 146 clones, 35 were selected for secondary screening. The selected clones were plated at low density and single clones were isolated after hybridization to the HH0779 probe using the hybridization conditions described above. The plasmids were then isolated from the λ Zap clones using the VCSM13 helper phage purchased from Stratagene. The plasmid DNA was analyzed by restriction digestion and PCR, and the clones containing the 24 largest inserts were selected and sequenced. Of the 24 sequenced clones, 6 encoded LIR-P3G2, 3 encoded LIR-pbm2, 8 encoded LIR-pbm36-4 and LIR-pbm36-2, 1 encoded LIR-pbm8, 2 encoded LIR-pmbhh, and 1 encoded a novel sequence designated LIR-pbmnew. Three clones were identified as encoding amino acid sequences that are not relevant to the LIR polypeptide family.

Example 11

Association of LIR-P3G2 and LIR-pbm8 with Tyrosine Phosphatase, SHP-1

The following describes the tests performed to demonstrate that LIR-P3G2 and LIR-pbm8 associate with SHP-1. Human monocytes were cultured in RPMI medium supplemented with 10% FBS, concentrated by centrifugation and finally subdivided into two aliquots. One aliquot was stimulated with a solution of 50 mM/mL sodium pervanadate for 5 minutes. The second aliquot was not stimulated. After stimulation, the cells in each aliquot were immediately lysed in RIPA buffer containing 1% NP-40, 0.5% sodium deoxycholate, 50 mM Tris pH8, 2 mM EDTA, 0.5 mM sodium orthovanadate, 5 mM sodium fluoride, 25 mM β-glycerol phosphate, and protease inhibitors. Samples of 24×10$^6$ cell equivalents were incubated for 2 hours at 4° C. with either 5 µg/mL of anti-SHP-1 antibody purchased from Transduction Laboratories, or 5 µg/mL of an isotype-matched antibody control (anti-Flag-M5 IgG1). The resulting immunocomplexes were precipitated by incubation with protein G-agarose (Boehringer Mannheim), washed, and resuspended in 40 mL of 2×SDS-PAGE sample buffer. Twenty microliters of each immunoprecipitate were loaded onto electrophoresis gels, electrophoresed under reducing conditions, and transferred to nitrocellulose membranes purchased from Amersham. Western blots were probed with anti-LIR-P3G2 monoclonal antibody sera and anti-LIR-pbm8 monoclonal antibody antisera and the immunocomplexes were detected by enhanced chemiluminescence (NEN).

A protein having a molecular weight of approximately 120 kDa, corresponding to LIR-P3G2 was readily detected in SHP-1 immunoprecipitates, but not the immunoprecipitates generated with the anti-Flag-M5 antibody control. Similarly, a protein of 90–100 kDa, corresponding to LIR-pbm8, was detected in SHP-1 immunoprecipitates, but not in the control immunoprecipitates. Neither the LIR-P3G2 band nor the LIR-pbm8 band was seen in the absence of sodium pervanadate treatment. This confirms that tyrosine phosphorylation of LIR-P3G2 is essential for the association of LIR-P3G2 and SHP-1 and phosphorylation of LIR-pbm8 is essential for the association of LIR-pbm8 and SHP-1.

To study the inhibition of FcγRI-mediated tyrosine phosphorylation events upon LIR coligation, peripheral blood monocytes were incubated with or without 10 µg/mL of F(ab)$_2$ version of a number of antibodies (α-LIR-1+α-LIR-2, α-CD11c, αCD14, αCD64, α-CD64+α-LIR-1, α-CD64+α-LIR-2, α-CD64+α-LIR-1+α-LIR-2, αCD64+αCD11c, α-CD64+α-CD14). This was followed with crosslinking with 30 µ/mL of polyclonal F(ab)$_2$ goat anti-mouse. Cell lysates were immunoprecipitated overnight with anti-phosphotyrosine conjugated agarose, electrophoresed, and transferred onto nitrocellulose Western blotting was performed using a combination of PY-20 and 4G10 HRP-conjugated anti-phosphotyrosine mAbs. This data demonstrates the specific inhibition of FcγRI-mediated tyrosine phosphorylation events upon LIR-P3G2 and LIR-pbm8 coligation.

Example 12

Generating Antibodies Immunoreactive with LIR Polypeptides

The following describes generating monoclonal antibody immunoreactive with LIR family members. A purified LIR polypeptide is prepared by COS-1 cell expression and affinity purification as described in Example 4. The purified protein or cells transfected with an expression vector encoding the full length protein can generate monoclonal antibodies against the LIR polypeptide using conventional techniques, for example those techniques described in U.S. Pat. No. 4,411,993. Briefly BALB-C mice are immunized at 0, 2 and 6 weeks with 10 μg of the LIR polypeptide. The primary immunization is prepared with TITERMAX adjuvant and subsequent immunizations are prepared with incomplete Freund's adjuvant (IFA). At 11 weeks, the mice are IV boosted with 3–4 μg the LIR polypeptide in PBS. Three days after the IV boost, splenocytes are harvested and fused with an Ag8.653 myeloma fusion partner using 50% aqueous PEG 1500 solution. Hybridoma supernatants are screened by ELISA using the LIR transfected cells in PBS at $7\times10^3$ cells per well and dried to polystyrene 96-well microtiter plates as the platecoat antigen. Positive supernatants are subsequently confirmed by FACS analysis and RIP using LIR transfected cells. Hybridomas are cloned and followed in the same manner of screening. Monoclonal cultures are expanded and supernatants purified by affinity chromatography.

Example 13

Flow Cytometric Analysis for Expression of LIR-P3G2 and LIR-pbm8 on Lymphoid and Myeloid Cells In order to compare the differential expression and distribution of LIR-P3G2 and LIR-pbm8 on lymphocyte populations, freshly isolated peripheral blood mononuclear cells (PBMC) were stained with PE-labeled anti-CD3, anti-CD19, or anti-CD56 mAb in the presence of either biotin labeled anti-LIR-P3G2 or anti LIR-pbm8 mAb. Then the stained cells were treated with APC-labeled streptavidin. Density plots representing $5\times10^4$ events were collected on a FACScaliber (from Beckton Dickinson). The results demonstrated that LIR-P3G2 is expressed on 80%–95% of $CD19^+$ B cells, on 5%–15% $CD3^+$ T cells, and on 10%–30% $CD56^+$ NK cells. On the cells examiner from the same 12 donors, LIR-pbm8 expression was not detected on $CD19^+$ B cells, $CD3^+$ T cells, and $CD56^+$ NK cells.

Countercurrent elutriated fractions containing a high percentage of circulating monocytes and dendritic cells (DC) were obtained. The monocytes were characterized according to the phenotypes subsets $CD14^+CD16^-$ and $CD14^+CD16^+$. The peripheral blood DC were characterized with the phenotype $CD33^+CD14^-CD16^-HLA-DR^+$. The monocytes subsets and DC's were stained with FITC-labeled antiCD14, PE-labeled anti CD3, perCp-labeled antiHLA-DR, and either biotin-labeled anti-CD16, anti-LIR-P3G2, or anti LIR-pbm8. Then the stained cells were treated with APC-labeled streptavidin. Both monocyte subsets co-express similar levels of LIR-P3G2 and LIR-pbm8, with the highest LIR-P3G2 and LIR-pbm8 expression detected on the $CD14^+$ $CD16^+$ subset. Blood DC express lower levels of LIR-P3G2 and LIR-pbm8 compared to monocytes. The results of these experiments demonstrate the LIR-P3G2 is expressed on lymphocytes, monocytes and DC, and LIR-pbm8 is expressed on monocytes and DC.

Example 14

Screening LIR-P3G2 and LIR-pbm8 Binding to HLA Class I Alleles

The following describes flow cytometry analyses used to screen LIR-P3G2 and LIR-pbm8 for binding to HLA Class I alleles. The B lymphoblastoid class I-deficient 721.221 cell line, untransfected or transfected with a panel of HLA class I alleles was used for staining. LIR-P3G2/Fc and LIR-pbm8/Fc fusion proteins were used in the binding studies and both bound detectably to seven of the eleven HLA-A, HLA-B and HLA-C alleles that were tested. In general, LIR-P3G2/Fc and LIR-pbm8/Fc bind with higher affinity to HLA-B alleles than to HLA-A or HLA-C alleles. W6/32 (ATCC HB-95), an antibody against MHC Class I heavy chains (an anti HLA-A, B, and C molecule) inhibits LIR-P3G2/Fc and LIR-pbm8/Fc binding to all class I transfectants. Finally, LIR-P3G2 and LIR-pbm8 binding does not correlate with the MHC class I expression levels. Thus, LIR-P3G2 and LIR-pbm8 bind to several HLA-A, -B, and -C alleles, and recognize a similar broad spectrum of MHC class I specificities.

Example 15

Isolation of LIR-9m1, LIR-9m, LIR-9s1, LIR-9s2 and LIR-10

In the course of high throughput sequencing of a human dendritic cell cDNA library, it was noted that the sequence of an incomplete cDNA (clone ss4894) was strikingly similar to the nucleotide sequences of LIRs 6a, 6b and 7, thus suggesting that ss4894 was a member of the LIR gene family. To obtain the remainder of this cDNA clone, the Rapid Amplification cDNA Extension system (RACE) was used to amplify a human leukocyte cDNA library (Chenchik et al., A new method for full-length cDNA cloning by PCR, In *A Laboratory Guide to RNA: Isolation, Analysis, and Synthesis*, Ed. Kreig, P. A. (Wiley-Liss, Inc.), pages 273–321). The first round of amplification employed one primer corresponding to the RACE adapter at the 5' end of the cDNAs, and a second primer corresponding to sequences near the 3' end of ss4894. This effort yielded several clones that contained sequence that was highly homologous though not identical to that of ss4894 and that extended upstream beyond an initiating methionine codon. These clones, however, lacked some of the sequence at the 3' end of the coding region. In an effort to obtain an entire coding region, another round of RACE sequencing was performed, this time using a first primer from near the 5' end of the first RACE products, and a second primer corresponding to the 3' adapter. This effort yielded five clones containing LIR inserts, four of which are closely related and appear to encode variants of the same gene. These four closely related cDNA sequences were designated LIR-9m1, LIR-9m2, LIR-9s1 and LIR-9s2 (SEQ ID NOS:29, 31, 33 and 35). The fifth of the clones obtained using this last set of primers represented a different gene, which has been designated LIR-10 (SEQ ID NO:37).

All four of the LIR-9 clones encode variants of the same protein, and are presumed to be the products of alternative splicing. The proteins encoded by LIR-9m1 (SEQ ID NO:30) and LIR-9s1 (SEQ ID NO:34) contain a 12 amino acid insert that is absent from LIR-9m2 (SEQ ID NO:32) and LIR-9s2 (SEQ ID NO:36). The soluble forms of the LIR-9 protein, i.e., LIR-9s1 and LIR-9s2, diverge near their carboxy termini from the membrane forms, i.e., LIRs-9m1 and -9m2. This divergence presumably is due to different exons being used by the soluble and membrane forms to encode that region of the protein.

What is claimed is:

1. An isolated nucleic acid molecule encoding an LIR polypeptide, wherein said LIR polypeptide comprises an amino acid sequence selected from the group consisting of SEQ ID NO:30, SEQ ID NO:32, SEQ ID NO:34, SEQ ID NO:36 and SEQ ID NO:38.

2. An isolated nucleic acid molecule of claim 1, wherein the nucleic acid molecule has a nucleotide sequence selected from the group consisting of SEQ ID NO:29, SEQ ID NO:31, SEQ ID NO:33, SEQ ID NO:35 and SEQ ID NO:37.

3. An isolated nucleic acid molecule according to claim 1, wherein the nucleic acid molecule comprises nucleotides 69–968 of SEQ ID NO:29.

4. An isolated nucleic acid molecule according to claim 1, wherein the nucleic acid molecule comprises nucleotides 95–958 of SEQ ID NO:31.

5. An isolated nucleic acid molecule according to claim 1, wherein the nucleic acid molecule comprises nucleotides 115–912 of SEQ ID NO:33.

6. An isolated nucleic acid molecule according to claim 1, wherein the nucleic acid molecule comprises nucleotides 73–834 of SEQ ID NO:35.

7. An isolated nucleic acid molecule according to claim 1, wherein the nucleic acid molecule comprises nucleotides 1–1350 of SEQ ID NO:37.

8. An isolated nucleic acid molecule encoding a soluble LIR polypeptide, wherein said LIR polypeptide comprises an amino acid sequence selected from the group consisting of:

the extracellular domain of a LIR family member, wherein the extracellular domain is selected from the group consisting of:

amino acids $x_{11}$ to 262 of SEQ ID NO:30, wherein $x_{11}$ is amino acid 1 or 35;

amino acids $x_{12}$ to 250 of SEQ ID NO:32, wherein $x_{12}$ is amino acid 1 or 36;

amino acids $x_{13}$ to 265 of SEQ ID NO:34, wherein $x_{13}$ is amino acid 1 or 35;

amino acids $x_{14}$ to 253 of SEQ ID NO:36, wherein $x_{14}$ is amino acid 1 or 36; and amino acids 1–393 of SEQ ID NO:38.

9. An isolated nucleic acid molecule encoding a soluble LIR polypeptide comprising at least one Ig-like domain, wherein said LIR polypeptide comprises at least 85 amino acids selected from the group consisting of:

amino acids $x_{11}$ to 262 of SEQ ID NO:30, wherein $x_{11}$ is amino acid 1 or 35;

amino acids $x_{12}$ to 250 of SEQ ID NO:32, wherein $x_{12}$ is amino acid 1 or 36;

amino acids $x_{13}$ to 265 of SEQ ID NO:34, wherein $x_{13}$ is amino acid 1 or 35;

amino acids $x_{14}$ to 253 of SEQ ID NO:36, wherein $x_{14}$ is amino acid 1 or 36; and amino acids 1 to 393 of SEQ ID NO:38.

10. A nucleic acid molecule that encodes a fusion protein comprising the Fc region of Ig and an amino acid sequence selected from the group consisting of:

amino acids $x_{11}$ to 262 of SEQ ID NO:30, wherein $x_{11}$ is amino acid 1 or 35;

amino acids $x_{12}$ to 250 of SEQ ID NO:32, wherein $x_{12}$ is amino acid 1 or 36;

amino acids $x_{13}$ to 265 of SEQ ID NO:34, wherein $x_{13}$ is amino acid 1 or 35;

amino acids $x_{14}$ to 253 of SEQ ID NO:36, wherein $x_{14}$ is amino acid 1 or 36; and amino acids 1 to 393 of SEQ ID NO:38.

11. A recombinant expression vector comprising a nucleic acid molecule according to claim 1.

12. A process for preparing an LIR polypeptide, the process comprising culturing a host cell transformed with an expression vector of claim 11 under conditions that promote expression of said polypeptide, and recovering said polypeptide.

13. A host cell transformed or transfected with an expression vector according to claim 11.

14. A nucleic acid molecule according to claim 9, wherein said nucleic acid molecule is selected from the group consisting of nucleic acid molecules comprising:

nucleotides 171–854 of SEQ ID NO:29;
nucleotides 200–844 of SEQ ID NO:31;
nucleotides 217–909 of SEQ ID NO:33;
nucleotides 178–831 of SEQ ID NO:35; and
nucleotides 1–1179 of SEQ ID NO:37.

15. A nucleic acid molecule according to claim 14, wherein said nucleic acid molecule further comprises a nucleotide sequence encoding a polypeptide selected from the group consisting of a signal sequence, a poly-HIS sequence, an amino acid sequence comprising Asp-Tyr-Lys-Asp-Asp-Asp-Asp-Lys (SEQ ID NO:39), a leucine zipper and a peptide linker.

16. A recombinant expression vector comprising a nucleic acid molecule according to claim 9.

17. A process for preparing an LIR polypeptide, the process comprising culturing a host cell transformed with an expression vector of claim 16 under conditions that promote expression of said polypeptide, and recovering said polypeptide.

18. A host cell transformed or transfected with an expression vector according to claim 16.

* * * * *

SEQUENCE LISTING

<160> NUMBER OF SEQ ID NOS: 39

<210> SEQ ID NO 1
<211> LENGTH: 2922
<212> TYPE: DNA
<213> ORGANISM: human
<220> FEATURE:
<221> NAME/KEY: CDS
<222> LOCATION: (310)..(2262)

<400> SEQUENCE: 1

```
agggccacgc gtgcatgcgt cgactggaac gagacgacct gctgtgaccc c cttgtgggc        60 actccattgg ttttatggcg cctctacttt ctggagtttg tgtaaaacaa a aatattatg       120 gtctttgtgc acatttacat caagctcagc ctgggcggca cagccagatg c gagatgcgt       180 ctctgctgat ctgagtctgc ctgcagcatg gacctgggtc ttccctgaag c atctccagg       240 gctggaggga cgactgccat gcaccgaggg ctcatccatc cacagagcag g gcagtggga       300 ggagacgcc atg acc ccc atc ctc acg gtc ctg at c tgt ctc ggg ctg           348
          Met Thr Pro Ile Leu  Thr Val Leu Ile Cys Leu Gly Leu
            1               5                  10 agt ctg ggc ccc cgg acc cac gtg cag gca g gg cac ctc ccc aag ccc         396
Ser Leu Gly Pro Arg Thr His Val Gln Ala G ly His Leu Pro Lys Pro
     15                  20                 25 acc ctc tgg gct gaa cca ggc tct gtg atc a cc cag ggg agt cct gtg         444
Thr Leu Trp Ala Glu Pro Gly Ser Val Ile T hr Gln Gly Ser Pro Val
 30                  35                 40                    45 acc ctc agg tgt cag ggg ggc cag gag acc c ag gag tac cgt cta tat         492
Thr Leu Arg Cys Gln Gly Gly Gln Glu Thr G ln Glu Tyr Arg Leu Tyr
                 50                   55                 60 aga gaa aag aaa aca gca ccc tgg att aca c gg atc cca cag gag ctt         540
Arg Glu Lys Lys Thr Ala Pro Trp Ile Thr A rg Ile Pro Gln Glu Leu
             65                   70                 75 gtg aag aag ggc cag ttc ccc atc cca tcc a tc acc tgg gaa cat gca         588
Val Lys Lys Gly Gln Phe Pro Ile Pro Ser I le Thr Trp Glu His Ala
         80                   85                 90 ggg cgg tat cgc tgt tac tat ggt agc gac a ct gca ggc cgc tca gag         636
Gly Arg Tyr Arg Cys Tyr Tyr Gly Ser Asp T hr Ala Gly Arg Ser Glu
     95                  100                105 agc agt gac ccc ctg gag ctg gtg gtg aca g ga gcc tac atc aaa ccc         684
Ser Ser Asp Pro Leu Glu Leu Val Val Thr G ly Ala Tyr Ile Lys Pro
110                  115                 120                 125 acc ctc tca gcc cag ccc agc ccc gtg gtg a ac tca gga ggg aat gta         732
Thr Leu Ser Ala Gln Pro Ser Pro Val Val A sn Ser Gly Gly Asn Val
                 130                 135                 140 acc ctc cag tgt gac tca cag gtg gca ttt g at ggc ttc att ctg tgt         780
Thr Leu Gln Cys Asp Ser Gln Val Ala Phe A sp Gly Phe Ile Leu Cys
             145                 150                 155 aag gaa gga gaa gat gaa cac cca caa tgc c tg aac tca cag ccc cat         828
Lys Glu Gly Glu Asp Glu His Pro Gln Cys L eu Asn Ser Gln Pro His
         160                 165                 170 gcc cgt ggg tcg tcc cgc gcc atc ttc tcc g tg ggc ccc gtg agc ccg         876
Ala Arg Gly Ser Ser Arg Ala Ile Phe Ser V al Gly Pro Val Ser Pro
     175                 180                 185 agt cgc agg tgg tgg tac agg tgc tat gct t at gac tcg aac tct ccc         924
Ser Arg Arg Trp Trp Tyr Arg Cys Tyr Ala T yr Asp Ser Asn Ser Pro
190                 195                 200                 205
```

| | |
|---|---|
| tat gag tgg tct cta ccc agt gat ctc ctg g ag ctc ctg gtc cta ggt<br>Tyr Glu Trp Ser Leu Pro Ser Asp Leu Leu G lu Leu Leu Val Leu Gly<br>210 215 220 | 972 |
| gtt tct aag aag cca tca ctc tca gtg cag c ca ggt cct atc gtg gcc<br>Val Ser Lys Lys Pro Ser Leu Ser Val Gln P ro Gly Pro Ile Val Ala<br>225 230 235 | 1020 |
| cct gag gag acc ctg act ctg cag tgt ggc t ct gat gct ggc tac aac<br>Pro Glu Glu Thr Leu Thr Leu Gln Cys Gly S er Asp Ala Gly Tyr Asn<br>240 245 250 | 1068 |
| aga ttt gtt ctg tat aag gac ggg gaa cgt g ac ttc ctt cag ctc gct<br>Arg Phe Val Leu Tyr Lys Asp Gly Glu Arg A sp Phe Leu Gln Leu Ala<br>255 260 265 | 1116 |
| ggc gca cag ccc cag gct ggg ctc tcc cag g cc aac ttc acc ctg ggc<br>Gly Ala Gln Pro Gln Ala Gly Leu Ser Gln A la Asn Phe Thr Leu Gly<br>270 275 280 285 | 1164 |
| cct gtg agc cgc tcc tac ggg ggc cag tac a ga tgc tac ggt gca cac<br>Pro Val Ser Arg Ser Tyr Gly Gly Gln Tyr A rg Cys Tyr Gly Ala His<br>290 295 300 | 1212 |
| aac ctc tcc tcc gag tgg tcg gcc ccc agc g ac ccc ctg gac atc ctg<br>Asn Leu Ser Ser Glu Trp Ser Ala Pro Ser A sp Pro Leu Asp Ile Leu<br>305 310 315 | 1260 |
| atc gca gga cag ttc tat gac aga gtc tcc c tc tcg gtg cag ccg ggc<br>Ile Ala Gly Gln Phe Tyr Asp Arg Val Ser L eu Ser Val Gln Pro Gly<br>320 325 330 | 1308 |
| ccc acg gtg gcc tca gga gag aac gtg acc c tg ctg tgt cag tca cag<br>Pro Thr Val Ala Ser Gly Glu Asn Val Thr L eu Leu Cys Gln Ser Gln<br>335 340 345 | 1356 |
| gga tgg atg caa act ttc ctt ctg acc aag g ag ggg gca gct gat gac<br>Gly Trp Met Gln Thr Phe Leu Leu Thr Lys G lu Gly Ala Ala Asp Asp<br>350 355 360 365 | 1404 |
| cca tgg cgt cta aga tca acg tac caa tct c aa aaa tac cag gct gaa<br>Pro Trp Arg Leu Arg Ser Thr Tyr Gln Ser G ln Lys Tyr Gln Ala Glu<br>370 375 380 | 1452 |
| ttc ccc atg ggt cct gtg acc tca gcc cat g cg ggg acc tac agg tgc<br>Phe Pro Met Gly Pro Val Thr Ser Ala His A la Gly Thr Tyr Arg Cys<br>385 390 395 | 1500 |
| tac ggc tca cag agc tcc aaa ccc tac ctg c tg act cac ccc agt gac<br>Tyr Gly Ser Gln Ser Ser Lys Pro Tyr Leu L eu Thr His Pro Ser Asp<br>400 405 410 | 1548 |
| ccc ctg gag ctc gtg gtc tca gga ccg tct g gg ggc ccc agc tcc ccg<br>Pro Leu Glu Leu Val Val Ser Gly Pro Ser G ly Gly Pro Ser Ser Pro<br>415 420 425 | 1596 |
| aca aca ggc ccc acc tcc aca tct ggc cct g ag gac cag ccc ctc acc<br>Thr Thr Gly Pro Thr Ser Thr Ser Gly Pro G lu Asp Gln Pro Leu Thr<br>430 435 440 445 | 1644 |
| ccc acc ggg tcg gat ccc cag agt ggt ctg g ga agg cac ctg ggg gtt<br>Pro Thr Gly Ser Asp Pro Gln Ser Gly Leu G ly Arg His Leu Gly Val<br>450 455 460 | 1692 |
| gtg atc ggc atc ttg gtg gcc gtc atc cta c tg ctc ctc ctc ctc ctc<br>Val Ile Gly Ile Leu Val Ala Val Ile Leu L eu Leu Leu Leu Leu Leu<br>465 470 475 | 1740 |
| ctc ctc ttc ctc atc ctc cga cat cga cgt c ag ggc aaa cac tgg aca<br>Leu Leu Phe Leu Ile Leu Arg His Arg Arg G ln Gly Lys His Trp Thr<br>480 485 490 | 1788 |
| tcg acc cag aga aag gct gat ttc caa cat c ct gca ggg gct gtg ggg<br>Ser Thr Gln Arg Lys Ala Asp Phe Gln His P ro Ala Gly Ala Val Gly<br>495 500 505 | 1836 |
| cca gag ccc aca gac aga ggc ctg cag tgg a gg tcc agc cca gct gcc<br>Pro Glu Pro Thr Asp Arg Gly Leu Gln Trp A rg Ser Ser Pro Ala Ala<br>510 515 520 525 | 1884 |

-continued

| | | |
|---|---|---|
| gat gcc cag gaa gaa aac ctc tat gct gcc g tg aag cac aca cag cct<br>Asp Ala Gln Glu Glu Asn Leu Tyr Ala Ala V al Lys His Thr Gln Pro<br>530 535 540 | | 1932 |
| gag gat ggg gtg gag atg gac act cgg agc c ca cac gat gaa gac ccc<br>Glu Asp Gly Val Glu Met Asp Thr Arg Ser P ro His Asp Glu Asp Pro<br>545 550 555 | | 1980 |
| cag gca gtg acg tat gcc gag gtg aaa cac t cc aga cct agg aga gaa<br>Gln Ala Val Thr Tyr Ala Glu Val Lys His S er Arg Pro Arg Arg Glu<br>560 565 570 | | 2028 |
| atg gcc tct cct cct tcc cca ctg tct ggg g aa ttc ctg gac aca aag<br>Met Ala Ser Pro Pro Ser Pro Leu Ser Gly G lu Phe Leu Asp Thr Lys<br>575 580 585 | | 2076 |
| gac aga cag gcg gaa gag gac agg cag atg g ac act gag gct gct gca<br>Asp Arg Gln Ala Glu Glu Asp Arg Gln Met A sp Thr Glu Ala Ala Ala<br>590 595 600 605 | | 2124 |
| tct gaa gcc ccc cag gat gtg acc tac gcc c ag ctg cac agc ttg acc<br>Ser Glu Ala Pro Gln Asp Val Thr Tyr Ala G ln Leu His Ser Leu Thr<br>610 615 620 | | 2172 |
| ctt aga cgg aag gca act gag cct cct cca t cc cag gaa ggg ccc tct<br>Leu Arg Arg Lys Ala Thr Glu Pro Pro Pro S er Gln Glu Gly Pro Ser<br>625 630 635 | | 2220 |
| cca gct gtg ccc agc atc tac gcc act ctg g cc atc cac tag<br>Pro Ala Val Pro Ser Ile Tyr Ala Thr Leu A la Ile His<br>640 645 650 | | 2262 |
| cccaggggggg gacgcagacc ccacactcca tggagtctgg aatgcatggg a gctgccccc | | 2322 |
| ccagtggaca ccattggacc ccacccagcc tggatctacc ccaggagact c tgggaactt | | 2382 |
| ttagggggtca ctcaattctg cagtataaat aactaatgtc tctacaattt t gaaataaag | | 2442 |
| caacagactt ctcaataatc aatgaagtag ctgagaaaac taagtcagaa a gtgcattaa | | 2502 |
| actgaatcac aatgtaaata ttacacatca agcgatgaaa ctggaaaact a caagccacg | | 2562 |
| aatgaatgaa ttaggaaaga aaaaagtag gaaatgaatg atcttggctt t cctataaga | | 2622 |
| aatttagggc agggcacggt ggctcacgcc tgtaattcca gcactttggg a ggccgaggc | | 2682 |
| gggcagatca cgagttcagg agatcgagac catcttggcc aacatggtga a accctgtct | | 2742 |
| ctcctaaaaa tacaaaaatt agctggatgt ggtggcagtg cctgtaatcc c agctatttg | | 2802 |
| ggaggctgag gcaggagaat cgcttgaacc agggagtcag aggtttcagt g agccaagat | | 2862 |
| cgcaccactg ctctccagcc tggcgacaag caggtcgtct cgttccagtc g acggcccat | | 2922 |

<210> SEQ ID NO 2
<211> LENGTH: 650
<212> TYPE: PRT
<213> ORGANISM: human

<400> SEQUENCE: 2

Met Thr Pro Ile Leu Thr Val Leu Ile Cys L eu Gly Leu Ser Leu Gly
1               5                   10                  15

Pro Arg Thr His Val Gln Ala Gly His Leu P ro Lys Pro Thr Leu Trp
        20                  25                  30

Ala Glu Pro Gly Ser Val Ile Thr Gln Gly S er Pro Val Thr Leu Arg
    35                  40                  45

Cys Gln Gly Gly Gln Glu Thr Gln Glu Tyr A rg Leu Tyr Arg Glu Lys
50                  55                  60

Lys Thr Ala Pro Trp Ile Thr Arg Ile Pro G ln Glu Leu Val Lys Lys
65                  70                  75                  80

Gly Gln Phe Pro Ile Pro Ser Ile Thr Trp G lu His Ala Gly Arg Tyr
                85                  90                  95

```
Arg Cys Tyr Tyr Gly Ser Asp Thr Ala Gly A rg Ser Glu Ser Ser Asp
            100                 105                 110

Pro Leu Glu Leu Val Val Thr Gly Ala Tyr I le Lys Pro Thr Leu Ser
        115                 120                 125

Ala Gln Pro Ser Pro Val Val Asn Ser Gly G ly Asn Val Thr Leu Gln
        130                 135                 140

Cys Asp Ser Gln Val Ala Phe Asp Gly Phe I le Leu Cys Lys Glu Gly
145                 150                 155                 160

Glu Asp Glu His Pro Gln Cys Leu Asn Ser G ln Pro His Ala Arg Gly
                165                 170                 175

Ser Ser Arg Ala Ile Phe Ser Val Gly Pro V al Ser Pro Ser Arg Arg
            180                 185                 190

Trp Trp Tyr Arg Cys Tyr Ala Tyr Asp Ser A sn Ser Pro Tyr Glu Trp
        195                 200                 205

Ser Leu Pro Ser Asp Leu Leu Glu Leu Leu V al Leu Gly Val Ser Lys
        210                 215                 220

Lys Pro Ser Leu Ser Val Gln Pro Gly Pro I le Val Ala Pro Glu Glu
225                 230                 235                 240

Thr Leu Thr Leu Gln Cys Gly Ser Asp Ala G ly Tyr Asn Arg Phe Val
                245                 250                 255

Leu Tyr Lys Asp Gly Glu Arg Asp Phe Leu G ln Leu Ala Gly Ala Gln
            260                 265                 270

Pro Gln Ala Gly Leu Ser Gln Ala Asn Phe T hr Leu Gly Pro Val Ser
        275                 280                 285

Arg Ser Tyr Gly Gly Gln Tyr Arg Cys Tyr G ly Ala His Asn Leu Ser
        290                 295                 300

Ser Glu Trp Ser Ala Pro Ser Asp Pro Leu A sp Ile Leu Ile Ala Gly
305                 310                 315                 320

Gln Phe Tyr Asp Arg Val Ser Leu Ser Val G ln Pro Gly Pro Thr Val
                325                 330                 335

Ala Ser Gly Glu Asn Val Thr Leu Leu Cys G ln Ser Gln Gly Trp Met
            340                 345                 350

Gln Thr Phe Leu Leu Thr Lys Glu Gly Ala A la Asp Asp Pro Trp Arg
        355                 360                 365

Leu Arg Ser Thr Tyr Gln Ser Gln Lys Tyr G ln Ala Glu Phe Pro Met
370                 375                 380

Gly Pro Val Thr Ser Ala His Ala Gly Thr T yr Arg Cys Tyr Gly Ser
385                 390                 395                 400

Gln Ser Ser Lys Pro Tyr Leu Leu Thr His P ro Ser Asp Pro Leu Glu
                405                 410                 415

Leu Val Val Ser Gly Pro Ser Gly Gly Pro S er Ser Pro Thr Thr Gly
            420                 425                 430

Pro Thr Ser Thr Ser Gly Pro Glu Asp Gln P ro Leu Thr Pro Thr Gly
        435                 440                 445

Ser Asp Pro Gln Ser Gly Leu Gly Arg His L eu Gly Val Val Ile Gly
        450                 455                 460

Ile Leu Val Ala Val Ile Leu Leu Leu Leu L eu Leu Leu Leu Leu Phe
465                 470                 475                 480

Leu Ile Leu Arg His Arg Arg Gln Gly Lys H is Trp Thr Ser Thr Gln
                485                 490                 495

Arg Lys Ala Asp Phe Gln His Pro Ala Gly A la Val Gly Pro Glu Pro
            500                 505                 510
```

-continued

```
Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
                580                 585                 590

Ala Glu Glu Asp Arg Gln Met Asp Thr Glu Ala Ala Ala Ser Glu Ala
            595                 600                 605

Pro Gln Asp Val Thr Tyr Ala Gln Leu His Ser Leu Thr Leu Arg Arg
        610                 615                 620

Lys Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650

<210> SEQ ID NO 3
<211> LENGTH: 2777
<212> TYPE: DNA
<213> ORGANISM: human
<220> FEATURE:
<221> NAME/KEY: CDS
<222> LOCATION: (168)..(2126)

<400> SEQUENCE: 3
agctcagcct gggcggcaca gccagatgcg agatgcgtct ctgctgatct g agtctgcct      60 gcagcatgga cctgggtctt ccctgaagca tctccagggc tggagggacg a ctgccatgc    120 accgagggct catccatcca cagagcaggg cagtgggagg agacgcc atg acc ccc       176
                                                    Met Thr Pro
                                                      1 atc ctc acg gtc ctg atc tgt ctc ggg ctg a gt ctg ggc ccc agg acc      224
Ile Leu Thr Val Leu Ile Cys Leu Gly Leu S er Leu Gly Pro Arg Thr
      5                  10                  15 cac gtg cag gca ggg cac ctc ccc aag ccc a cc ctc tgg gct gaa cca      272
His Val Gln Ala Gly His Leu Pro Lys Pro T hr Leu Trp Ala Glu Pro
 20                  25                  30                  35 ggc tct gtg atc acc cag ggg agt cct gtg a cc ctc agg tgt cag ggg      320
Gly Ser Val Ile Thr Gln Gly Ser Pro Val T hr Leu Arg Cys Gln Gly
             40                  45                  50 ggc cag gag acc cag gag tac cgt cta tat a ga gaa aag aaa aca gca      368
Gly Gln Glu Thr Gln Glu Tyr Arg Leu Tyr A rg Glu Lys Lys Thr Ala
         55                  60                  65 ctc tgg att aca cgg atc cca cag gag ctt g tg aag aag ggc cag ttc      416
Leu Trp Ile Thr Arg Ile Pro Gln Glu Leu V al Lys Lys Gly Gln Phe
     70                  75                  80 ccc atc cca tcc atc acc tgg gaa cat gca g gg cgg tat cgc tgt tac      464
Pro Ile Pro Ser Ile Thr Trp Glu His Ala G ly Arg Tyr Arg Cys Tyr
 85                  90                  95 tat ggt agc gac act gca ggc cgc tca gag a gc agt gac ccc ctg gag      512
Tyr Gly Ser Asp Thr Ala Gly Arg Ser Glu S er Ser Asp Pro Leu Glu
100                 105                 110                 115 ctg gtg gtg aca gga gcc tac atc aaa ccc a cc ctc tca gcc cag ccc      560
Leu Val Val Thr Gly Ala Tyr Ile Lys Pro T hr Leu Ser Ala Gln Pro
            120                 125                 130
```

```
agc ccc gtg gtg aac tca gga ggg aat gta a tc ctc cag tgt gac tca      608
Ser Pro Val Val Asn Ser Gly Gly Asn Val I le Leu Gln Cys Asp Ser
            135                 140                 145 cag gtg gca ttt gat ggc ttc agt ctg tgt a ag gaa gga gaa gat gaa      656
Gln Val Ala Phe Asp Gly Phe Ser Leu Cys L ys Glu Gly Glu Asp Glu
            150                 155                 160 cac cca caa tgc ctg aac tcc cag ccc cat g cc cgt ggg tcg tcc cgc      704
His Pro Gln Cys Leu Asn Ser Gln Pro His A la Arg Gly Ser Ser Arg
            165                 170                 175 gcc atc ttc tcc gtg ggc ccc gtg agc ccg a gt cgc agg tgg tgg tac      752
Ala Ile Phe Ser Val Gly Pro Val Ser Pro S er Arg Arg Trp Trp Tyr
180                 185                 190                 195 agg tgc tat gct tat gac tcg aac tct ccc t at gag tgg tct cta ccc      800
Arg Cys Tyr Ala Tyr Asp Ser Asn Ser Pro T yr Glu Trp Ser Leu Pro
            200                 205                 210 agt gat ctc ctg gag ctc ctg gtc cta ggt g tt tct aag aag cca tca      848
Ser Asp Leu Leu Glu Leu Leu Val Leu Gly V al Ser Lys Lys Pro Ser
            215                 220                 225 ctc tca gtg cag cca ggt cct atc gtg gcc c ct gag gag acc ctg act      896
Leu Ser Val Gln Pro Gly Pro Ile Val Ala P ro Glu Glu Thr Leu Thr
            230                 235                 240 ctg cag tgt ggc tct gat gct ggc tac aac a ga ttt gtt ctg tat aag      944
Leu Gln Cys Gly Ser Asp Ala Gly Tyr Asn A rg Phe Val Leu Tyr Lys
            245                 250                 255 gac ggg gaa cgt gac ttc ctt cag ctc gct g gc gca cag ccc cag gct      992
Asp Gly Glu Arg Asp Phe Leu Gln Leu Ala G ly Ala Gln Pro Gln Ala
260                 265                 270                 275 ggg ctc tcc cag gcc aac ttc acc ctg ggc c ct gtg agc cgc tcc tac     1040
Gly Leu Ser Gln Ala Asn Phe Thr Leu Gly P ro Val Ser Arg Ser Tyr
            280                 285                 290 ggg ggc cag tac aga tgc tac ggt gca cac a ac ctc tcc tcc gag tgg     1088
Gly Gly Gln Tyr Arg Cys Tyr Gly Ala His A sn Leu Ser Ser Glu Trp
            295                 300                 305 tcg gcc ccc agt gac ccc ctg gac atc ctg a tc gca gga cag ttc tat     1136
Ser Ala Pro Ser Asp Pro Leu Asp Ile Leu I le Ala Gly Gln Phe Tyr
            310                 315                 320 gac aga gtc tcc ctc tcg gtg cag ccg ggc c cc acg gtg gcc tca gga     1184
Asp Arg Val Ser Leu Ser Val Gln Pro Gly P ro Thr Val Ala Ser Gly
            325                 330                 335 gag aac gtg acc ctg ctg tgt cag tca cag g ga tgg atg caa act ttc     1232
Glu Asn Val Thr Leu Leu Cys Gln Ser Gln G ly Trp Met Gln Thr Phe
340                 345                 350                 355 ctt ctg acc aag gag ggg gca gct gat gac c ca tgg cgt cta aga tca     1280
Leu Leu Thr Lys Glu Gly Ala Ala Asp Asp P ro Trp Arg Leu Arg Ser
            360                 365                 370 acg tac caa tct caa aaa tac cag gct gaa t tc ccc atg ggt cct gtg     1328
Thr Tyr Gln Ser Gln Lys Tyr Gln Ala Glu P he Pro Met Gly Pro Val
            375                 380                 385 acc tca gcc cat gcg ggg acc tac agg tgc t ac ggc tca cag agc tcc     1376
Thr Ser Ala His Ala Gly Thr Tyr Arg Cys T yr Gly Ser Gln Ser Ser
            390                 395                 400 aaa ccc tac ctg ctg act cac ccc agt gac c cc ctg gag ctc gtg gtc     1424
Lys Pro Tyr Leu Leu Thr His Pro Ser Asp P ro Leu Glu Leu Val Val
            405                 410                 415 tca gga ccg tct ggg ggc ccc agc tcc ccg a ca aca ggc ccc acc tcc     1472
Ser Gly Pro Ser Gly Gly Pro Ser Ser Pro T hr Thr Gly Pro Thr Ser
420                 425                 430                 435
```

```
aca tct gca ggc cct gag gac cag ccc ctc a cc ccc acc ggg tcg gat    1520
Thr Ser Ala Gly Pro Glu Asp Gln Pro Leu T hr Pro Thr Gly Ser Asp
                    440                 445                 450 ccc cag agt ggt ctg gga agg cac ctg ggg g tt gtg atc ggc atc ttg    1568
Pro Gln Ser Gly Leu Gly Arg His Leu Gly V al Val Ile Gly Ile Leu
        455                 460                 465 gtg gcc gtc atc cta ctg ctc ctc ctc c tc ctc ctc ttc ctc atc        1616
Val Ala Val Ile Leu Leu Leu Leu Leu L eu Leu Leu Phe Leu Ile
            470                 475                 480 ctc cga cat cga cgt cag ggc aaa cac tgg a ca tcg acc cag aga aag    1664
Leu Arg His Arg Arg Gln Gly Lys His Trp T hr Ser Thr Gln Arg Lys
485                 490                 495 gct gat ttc caa cat cct gca ggg gct gtg g gg cca gag ccc aca gac    1712
Ala Asp Phe Gln His Pro Ala Gly Ala Val G ly Pro Glu Pro Thr Asp
500                 505                 510                 515 aga ggc ctg cag tgg agg tcc agc cca gct g cc gat gcc cag gaa gaa    1760
Arg Gly Leu Gln Trp Arg Ser Ser Pro Ala A la Asp Ala Gln Glu Glu
                520                 525                 530 aac ctc tat gct gcc gtg aag cac aca cag c ct gag gat ggg gtg gag    1808
Asn Leu Tyr Ala Ala Val Lys His Thr Gln P ro Glu Asp Gly Val Glu
            535                 540                 545 atg gac act cgg cag agc cca cac gat gaa g ac ccc cag gca gtg acg    1856
Met Asp Thr Arg Gln Ser Pro His Asp Glu A sp Pro Gln Ala Val Thr
        550                 555                 560 tat gcc gag gtg aaa cac tcc aga cct agg a ga gaa atg gcc tct cct    1904
Tyr Ala Glu Val Lys His Ser Arg Pro Arg A rg Glu Met Ala Ser Pro
565                 570                 575 cct tcc cca ctg tct ggg gaa ttc ctg gac a ca aag gac aga cag gcg    1952
Pro Ser Pro Leu Ser Gly Glu Phe Leu Asp T hr Lys Asp Arg Gln Ala
580                 585                 590                 595 gaa gag gac agg cag atg gac act gag gct g ct gca tct gaa gcc ccc    2000
Glu Glu Asp Arg Gln Met Asp Thr Glu Ala A la Ala Ser Glu Ala Pro
                600                 605                 610 cag gat gtg acc tac gcc cag ctg cac agc t tg acc ctc aga cgg gag    2048
Gln Asp Val Thr Tyr Ala Gln Leu His Ser L eu Thr Leu Arg Arg Glu
            615                 620                 625 gca act gag cct cct cca tcc cag gaa ggg c cc tct cca gct gtg ccc    2096
Ala Thr Glu Pro Pro Pro Ser Gln Glu Gly P ro Ser Pro Ala Val Pro
        630                 635                 640 agc atc tac gcc act ctg gcc atc cac tag c ccagggggg gacgcagacc      2146
Ser Ile Tyr Ala Thr Leu Ala Ile His
    645                 650 ccacactcca tggagtctgg aatgcatggg agctgccccc ccagtggaca c cattggacc  2206 ccacccagcc tggatctacc ccaggagact ctgggaactt ttaggggtca c tcaattctg  2266 cagtataaat aactaatgtc tctacaattt tgaaataaag caatagactt c tcaataatc  2326 aatgaagtag ctgagaaaac taagtcagaa agtgcattaa actgaatcac a atgtaaata  2386 ttacacatca agcgatgaaa ctggaaaact acaagccacg aatgaatgaa t taggaaaga  2446 aaaaagtag gaaatgaatg atcttggctt tcctataaga aatttagggc a gggcacggt  2506 ggctcacgcc tgtaattcca gcactttggg aggccgaggc gggcagatca c gagttcagg  2566 agatcgagac catcttggcc aacatggtga acccctgtct ctcctaaaaa t acaaaaatt  2626 agctggatgt ggtggcagtg cctgtaatcc cagctatttg ggaggctgag g caggagaat  2686 cgcttgaacc agggagtcag aggtttcagt gagccaagat cgcaccactg c tctccagcc  2746 tggcgacaga gggagactcc atctcaaatt a                                  2777
```

-continued

```
<210> SEQ ID NO 4
<211> LENGTH: 652
<212> TYPE: PRT
<213> ORGANISM: human

<400> SEQUENCE: 4
```

| | | | | | | | | | | | | | | | |
|---|---|---|---|---|---|---|---|---|---|---|---|---|---|---|---|
| Met | Thr | Pro | Ile | Leu | Thr | Val | Leu | Ile | Cys | Leu | Gly | Leu | Ser | Leu | Gly |
| 1 | | | | 5 | | | | | 10 | | | | | 15 | |
| Pro | Arg | Thr | His | Val | Gln | Ala | Gly | His | Leu | Pro | Lys | Pro | Thr | Leu | Trp |
| | | | 20 | | | | | 25 | | | | | 30 | | |
| Ala | Glu | Pro | Gly | Ser | Val | Ile | Thr | Gln | Gly | Ser | Pro | Val | Thr | Leu | Arg |
| | | 35 | | | | | 40 | | | | | 45 | | | |
| Cys | Gln | Gly | Gly | Gln | Glu | Thr | Gln | Glu | Tyr | Arg | Leu | Tyr | Arg | Glu | Lys |
| 50 | | | | | 55 | | | | | 60 | | | | | |
| Lys | Thr | Ala | Leu | Trp | Ile | Thr | Arg | Ile | Pro | Gln | Glu | Leu | Val | Lys | Lys |
| 65 | | | | 70 | | | | | 75 | | | | | 80 | |
| Gly | Gln | Phe | Pro | Ile | Pro | Ser | Ile | Thr | Trp | Glu | His | Ala | Gly | Arg | Tyr |
| | | | | 85 | | | | | 90 | | | | | 95 | |
| Arg | Cys | Tyr | Tyr | Gly | Ser | Asp | Thr | Ala | Gly | Arg | Ser | Glu | Ser | Ser | Asp |
| | | | 100 | | | | | 105 | | | | | 110 | | |
| Pro | Leu | Glu | Leu | Val | Val | Thr | Gly | Ala | Tyr | Ile | Lys | Pro | Thr | Leu | Ser |
| | | 115 | | | | | 120 | | | | | 125 | | | |
| Ala | Gln | Pro | Ser | Pro | Val | Val | Asn | Ser | Gly | Gly | Asn | Val | Ile | Leu | Gln |
| 130 | | | | | 135 | | | | | 140 | | | | | |
| Cys | Asp | Ser | Gln | Val | Ala | Phe | Asp | Gly | Phe | Ser | Leu | Cys | Lys | Glu | Gly |
| 145 | | | | 150 | | | | | 155 | | | | | 160 | |
| Glu | Asp | Glu | His | Pro | Gln | Cys | Leu | Asn | Ser | Gln | Pro | His | Ala | Arg | Gly |
| | | | | 165 | | | | | 170 | | | | | 175 | |
| Ser | Ser | Arg | Ala | Ile | Phe | Ser | Val | Gly | Pro | Val | Ser | Pro | Ser | Arg | Arg |
| | | | 180 | | | | | 185 | | | | | 190 | | |
| Trp | Trp | Tyr | Arg | Cys | Tyr | Ala | Tyr | Asp | Ser | Asn | Ser | Pro | Tyr | Glu | Trp |
| | | | | 195 | | | | | 200 | | | | | 205 | |
| Ser | Leu | Pro | Ser | Asp | Leu | Leu | Glu | Leu | Leu | Val | Leu | Gly | Val | Ser | Lys |
| | | 210 | | | | | 215 | | | | | 220 | | | |
| Lys | Pro | Ser | Leu | Ser | Val | Gln | Pro | Gly | Pro | Ile | Val | Ala | Pro | Glu | Glu |
| 225 | | | | | 230 | | | | | 235 | | | | | 240 |
| Thr | Leu | Thr | Leu | Gln | Cys | Gly | Ser | Asp | Ala | Gly | Tyr | Asn | Arg | Phe | Val |
| | | | | 245 | | | | | 250 | | | | | 255 | |
| Leu | Tyr | Lys | Asp | Gly | Glu | Arg | Asp | Phe | Leu | Gln | Leu | Ala | Gly | Ala | Gln |
| | | | 260 | | | | | 265 | | | | | 270 | | |
| Pro | Gln | Ala | Gly | Leu | Ser | Gln | Ala | Asn | Phe | Thr | Leu | Gly | Pro | Val | Ser |
| | | 275 | | | | | 280 | | | | | 285 | | | |
| Arg | Ser | Tyr | Gly | Gly | Gln | Tyr | Arg | Cys | Tyr | Gly | Ala | His | Asn | Leu | Ser |
| | | 290 | | | | | 295 | | | | | 300 | | | |
| Ser | Glu | Trp | Ser | Ala | Pro | Ser | Asp | Pro | Leu | Asp | Ile | Leu | Ile | Ala | Gly |
| 305 | | | | | 310 | | | | | 315 | | | | | 320 |
| Gln | Phe | Tyr | Asp | Arg | Val | Ser | Leu | Ser | Val | Gln | Pro | Gly | Pro | Thr | Val |
| | | | | 325 | | | | | 330 | | | | | 335 | |
| Ala | Ser | Gly | Glu | Asn | Val | Thr | Leu | Leu | Cys | Gln | Ser | Gln | Gly | Trp | Met |
| | | | 340 | | | | | 345 | | | | | 350 | | |
| Gln | Thr | Phe | Leu | Leu | Thr | Lys | Glu | Gly | Ala | Ala | Asp | Asp | Pro | Trp | Arg |
| | | 355 | | | | | 360 | | | | | 365 | | | |
| Leu | Arg | Ser | Thr | Tyr | Gln | Ser | Gln | Lys | Tyr | Gln | Ala | Glu | Phe | Pro | Met |
| | | 370 | | | | | 375 | | | | | 380 | | | |

-continued

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
            405                 410                 415

Leu Val Val Ser Gly Pro Ser Gly Pro Ser Ser Pro Thr Thr Gly
            420                 425                 430

Pro Thr Ser Thr Ser Ala Gly Pro Glu Asp Gln Pro Leu Thr Pro Thr
            435                 440                 445

Gly Ser Asp Pro Gln Ser Gly Leu Gly Arg His Leu Gly Val Val Ile
450                 455                 460

Gly Ile Leu Val Ala Val Ile Leu Leu Leu Leu Leu Leu Leu Leu
465                 470                 475                 480

Phe Leu Ile Leu Arg His Arg Gln Gly Lys His Trp Thr Ser Thr
                485                 490                 495

Gln Arg Lys Ala Asp Phe Gln His Pro Ala Gly Ala Val Gly Pro Glu
500                 505                 510

Pro Thr Asp Arg Gly Leu Gln Trp Arg Ser Ser Pro Ala Ala Asp Ala
            515                 520                 525

Gln Glu Glu Asn Leu Tyr Ala Ala Val Lys His Thr Gln Pro Glu Asp
530                 535                 540

Gly Val Glu Met Asp Thr Arg Gln Ser Pro His Asp Glu Asp Pro Gln
545                 550                 555                 560

Ala Val Thr Tyr Ala Glu Val Lys His Ser Arg Pro Arg Arg Glu Met
            565                 570                 575

Ala Ser Pro Pro Ser Pro Leu Ser Gly Glu Phe Leu Asp Thr Lys Asp
            580                 585                 590

Arg Gln Ala Glu Glu Asp Arg Gln Met Asp Thr Glu Ala Ala Ala Ser
            595                 600                 605

Glu Ala Pro Gln Asp Val Thr Tyr Ala Gln Leu His Ser Leu Thr Leu
            610                 615                 620

Arg Arg Glu Ala Thr Glu Pro Pro Pro Ser Gln Glu Gly Pro Ser Pro
625                 630                 635                 640

Ala Val Pro Ser Ile Tyr Ala Thr Leu Ala Ile His
                645                 650

<210> SEQ ID NO 5
<211> LENGTH: 30
<212> TYPE: DNA
<213> ORGANISM: human

<400> SEQUENCE: 5
tatgtcgacc atgaccccca tcctcacggt                                    30

<210> SEQ ID NO 6
<211> LENGTH: 52
<212> TYPE: DNA
<213> ORGANISM: human

<400> SEQUENCE: 6
tatgggctct gctccaggag aagatcttcc ttctataacc cccaggtgcc t t          52

<210> SEQ ID NO 7
<211> LENGTH: 1605
<212> TYPE: DNA
<213> ORGANISM: human
<220> FEATURE:
<221> NAME/KEY: CDS
<222> LOCATION: (93)..(1412)

```
<400> SEQUENCE: 7
gagcctccaa gtgtccacac cctgtgtgtc ctctgtcctg ccagcaccga g ggctcatcc      60 atccacagag cagtgcagtg ggaggagacg cc atg acc ccc at c ctc acg gtc     113
                                    Met Thr Pro Ile Leu Thr Val
                                     1               5 ctg atc tgt ctc ggg ctg agc ctg gac ccc a gg acc cac gtg cag gca     161
Leu Ile Cys Leu Gly Leu Ser Leu Asp Pro A rg Thr His Val Gln Ala
         10                  15                    20 ggg ccc ctc ccc aag ccc acc ctc tgg gct g ag cca ggc tct gtg atc     209
Gly Pro Leu Pro Lys Pro Thr Leu Trp Ala G lu Pro Gly Ser Val Ile
 25                  30                     35 acc caa ggg agt cct gtg acc ctc agg tgt c ag ggg agc ctg gag acg     257
Thr Gln Gly Ser Pro Val Thr Leu Arg Cys G ln Gly Ser Leu Glu Thr
 40                  45                    50                  55 cag gag tac cat cta tat aga gaa aag aaa a ca gca ctc tgg att aca     305
Gln Glu Tyr His Leu Tyr Arg Glu Lys Lys T hr Ala Leu Trp Ile Thr
                 60                    65                  70 cgg atc cca cag gag ctt gtg aag aag ggc c ag ttc ccc atc cta tcc     353
Arg Ile Pro Gln Glu Leu Val Lys Lys Gly G ln Phe Pro Ile Leu Ser
             75                  80                    85 atc acc tgg gaa cat gca ggg cgg tat tgc t gt atc tat ggc agc cac     401
Ile Thr Trp Glu His Ala Gly Arg Tyr Cys C ys Ile Tyr Gly Ser His
         90                  95                    100 act gca ggc ctc tca gag agc agt gac ccc c tg gag ctg gtg gtg aca     449
Thr Ala Gly Leu Ser Glu Ser Ser Asp Pro L eu Glu Leu Val Val Thr
 105                 110                   115 gga gcc tac agc aaa ccc acc ctc tca gct c tg ccc agc cct gtg gtg     497
Gly Ala Tyr Ser Lys Pro Thr Leu Ser Ala L eu Pro Ser Pro Val Val
120                 125                    130                 135 acc tca gga agg aat gtg acc atc cag tgt g ac tca cag gtg gca ttt     545
Thr Ser Gly Arg Asn Val Thr Ile Gln Cys A sp Ser Gln Val Ala Phe
                 140                   145                 150 gat ggc ttc att ctg tgt aag gaa gga gaa g at gaa cac cca caa tgc     593
Asp Gly Phe Ile Leu Cys Lys Glu Gly Glu A sp Glu His Pro Gln Cys
             155                 160                   165 ctg aac tcc cat tcc cat gcc cgt ggg tca t cc cgg gcc atc ttc tcc     641
Leu Asn Ser His Ser His Ala Arg Gly Ser S er Arg Ala Ile Phe Ser
         170                 175                   180 gtg ggc ccc gtg agc cca agt cgc agg tgg t cg tac agg tgc tat ggt     689
Val Gly Pro Val Ser Pro Ser Arg Arg Trp S er Tyr Arg Cys Tyr Gly
 185                 190                   195 tat gac tcg cgc gct ccc tat gtg tgg tct c ta ccc agt gat ctc ctg     737
Tyr Asp Ser Arg Ala Pro Tyr Val Trp Ser L eu Pro Ser Asp Leu Leu
200                 205                    210                 215 ggg ctc ctg gtc cca ggt gtt tct aag aag c ca tca ctc tca gtg cag     785
Gly Leu Leu Val Pro Gly Val Ser Lys Lys P ro Ser Leu Ser Val Gln
                 220                   225                 230 ccg ggt cct gtc gtg gcc cct ggg gag aag c tg acc ttc cag tgt ggc     833
Pro Gly Pro Val Val Ala Pro Gly Glu Lys L eu Thr Phe Gln Cys Gly
             235                 240                   245 tct gat gcc ggc tac gac aga ttt gtt ctg t ac aag gag tgg gga cgt     881
Ser Asp Ala Gly Tyr Asp Arg Phe Val Leu T yr Lys Glu Trp Gly Arg
         250                 255                   260 gac ttc ctc cag cgc cct ggc cgg cag ccc c ag gct ggg ctc tcc cag     929
Asp Phe Leu Gln Arg Pro Gly Arg Gln Pro G ln Ala Gly Leu Ser Gln
 265                 270                   275 gcc aac ttc acc ctg ggc cct gtg agc cgc t cc tac ggg ggc cag tac     977
Ala Asn Phe Thr Leu Gly Pro Val Ser Arg S er Tyr Gly Gly Gln Tyr
280                 285                    290                 295
```

-continued

```
aca tgc tcc ggt gca tac aac ctc tcc tcc g ag tgg tcg gcc ccc agc    1025
Thr Cys Ser Gly Ala Tyr Asn Leu Ser Ser G lu Trp Ser Ala Pro Ser
            300                 305                 310 gac ccc ctg gac atc ctg atc aca gga cag a tc cgt gcc aga ccc ttc    1073
Asp Pro Leu Asp Ile Leu Ile Thr Gly Gln I le Arg Ala Arg Pro Phe
            315                 320                 325 ctc tcc gtg cgg ccg ggc ccc aca gtg gcc t ca gga gag aac gtg acc    1121
Leu Ser Val Arg Pro Gly Pro Thr Val Ala S er Gly Glu Asn Val Thr
            330                 335                 340 ctg ctg tgt cag tca cag gga ggg atg cac a ct ttc ctt ttg acc aag    1169
Leu Leu Cys Gln Ser Gln Gly Gly Met His T hr Phe Leu Leu Thr Lys
        345                 350                 355 gag ggg gca gct gat tcc ccg ctg cgt cta a aa tca aag cgc caa tct    1217
Glu Gly Ala Ala Asp Ser Pro Leu Arg Leu L ys Ser Lys Arg Gln Ser
360                 365                 370                 375 cat aag tac cag gct gaa ttc ccc atg agt c ct gtg acc tcg gcc cac    1265
His Lys Tyr Gln Ala Glu Phe Pro Met Ser P ro Val Thr Ser Ala His
            380                 385                 390 gcg ggg acc tac agg tgc tac ggc tca ctc a gc tcc aac ccc tac ctg    1313
Ala Gly Thr Tyr Arg Cys Tyr Gly Ser Leu S er Ser Asn Pro Tyr Leu
            395                 400                 405 ctg act cac ccc agt gac ccc ctg gag ctc g tg gtc tca gga gca gct    1361
Leu Thr His Pro Ser Asp Pro Leu Glu Leu V al Val Ser Gly Ala Ala
        410                 415                 420 gag acc ctc agc cca cca caa aac aag tcc g ac tcc aag gct ggt gag    1409
Glu Thr Leu Ser Pro Pro Gln Asn Lys Ser A sp Ser Lys Ala Gly Glu
425                 430                 435 tga ggagatgctt gccgtgatga cgctgggcac agagggtcag gtcctgtc aa         1462 gaggagctgg gtgtcctggg tggacatttg aagaattata ttcattccaa c ttgaagaat  1522 tattcaacac ctttaacaat gtatatgtga agtactttat tctttcatat t ttaaaaata  1582 aaagataatt atccatgaga aaa                                           1605
```

<210> SEQ ID NO 8
<211> LENGTH: 439
<212> TYPE: PRT
<213> ORGANISM: human
<400> SEQUENCE: 8

```
Met Thr Pro Ile Leu Thr Val Leu Ile Cys L eu Gly Leu Ser Leu Asp
 1               5                  10                  15

Pro Arg Thr His Val Gln Ala Gly Pro Leu P ro Lys Pro Thr Leu Trp
            20                  25                  30

Ala Glu Pro Gly Ser Val Ile Thr Gln Gly S er Pro Val Thr Leu Arg
        35                  40                  45

Cys Gln Gly Ser Leu Glu Thr Gln Glu Tyr H is Leu Tyr Arg Glu Lys
    50                  55                  60

Lys Thr Ala Leu Trp Ile Thr Arg Ile Pro G ln Glu Leu Val Lys Lys
65                  70                  75                  80

Gly Gln Phe Pro Ile Leu Ser Ile Thr Trp G lu His Ala Gly Arg Tyr
                85                  90                  95

Cys Cys Ile Tyr Gly Ser His Thr Ala Gly L eu Ser Glu Ser Ser Asp
            100                 105                 110

Pro Leu Glu Leu Val Val Thr Gly Ala Tyr S er Lys Pro Thr Leu Ser
        115                 120                 125

Ala Leu Pro Ser Pro Val Val Thr Ser Gly A rg Asn Val Thr Ile Gln
    130                 135                 140
```

-continued

```
Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Val Pro Gly Val Ser Lys
    210                 215                 220

Lys Pro Ser Leu Ser Val Gln Pro Gly Pro Val Val Ala Pro Gly Glu
225                 230                 235                 240

Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Thr Cys Ser Gly Ala Tyr Asn Leu Ser
    290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
    370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
                405                 410                 415

Leu Val Val Ser Gly Ala Ala Glu Thr Leu Ser Pro Pro Gln Asn Lys
            420                 425                 430

Ser Asp Ser Lys Ala Gly Glu
        435
```

<210> SEQ ID NO 9
<211> LENGTH: 2221
<212> TYPE: DNA
<213> ORGANISM: human
<220> FEATURE:
<221> NAME/KEY: CDS
<222> LOCATION: (184)..(1980)

<400> SEQUENCE: 9

```
gctcactgcc acacgcagct cagcctgggc ggcacagcca gatgcgagat g cgtctctgc      60 tgatctgagt ctgcctgcag catggacctg gtcttccct gaagcatctc c agggctgga     120 gggacgactg ccatgcaccg agggctcatc catccgcaga gcagggcagt g ggaggagac    180 gcc atg acc ccc atc gtc aca gtc ctg atc t gt ctc ggg ctg agt ctg      228
    Met Thr Pro Ile Val Thr Val Leu Ile Cys Leu Gly Leu Ser Leu
      1               5                  10                  15
```

-continued

| | | |
|---|---|---|
| ggc ccc agg acc cac gtg cag aca ggg acc a tc ccc aag ccc acc ctg<br>Gly Pro Arg Thr His Val Gln Thr Gly Thr I le Pro Lys Pro Thr Leu<br>                20                    25                   30 | 276 |
| tgg gct gag cca gac tct gtg atc acc cag g gg agt ccc gtc acc ctc<br>Trp Ala Glu Pro Asp Ser Val Ile Thr Gln G ly Ser Pro Val Thr Leu<br>          35                     40                     45 | 324 |
| agt tgt cag ggg agc ctt gaa gcc cag gag t ac cgt cta tat agg gag<br>Ser Cys Gln Gly Ser Leu Glu Ala Gln Glu T yr Arg Leu Tyr Arg Glu<br>        50                    55                       60 | 372 |
| aaa aaa tca gca tct tgg att aca cgg ata c ga cca gag ctt gtg aag<br>Lys Lys Ser Ala Ser Trp Ile Thr Arg Ile A rg Pro Glu Leu Val Lys<br>65                   70                      75 | 420 |
| aac ggc cag ttc cac atc cca tcc atc acc t gg gaa cac aca ggg cga<br>Asn Gly Gln Phe His Ile Pro Ser Ile Thr T rp Glu His Thr Gly Arg<br>80                   85                     90                   95 | 468 |
| tat ggc tgt cag tat tac agc cgc gct cgg t gg tct gag ctc agt gac<br>Tyr Gly Cys Gln Tyr Tyr Ser Arg Ala Arg T rp Ser Glu Leu Ser Asp<br>                 100                    105                 110 | 516 |
| ccc ctg gtg ctg gtg atg aca gga gcc tac c ca aaa ccc acc ctc tca<br>Pro Leu Val Leu Val Met Thr Gly Ala Tyr P ro Lys Pro Thr Leu Ser<br>               115                    120                 125 | 564 |
| gcc cag ccc agc cct gtg gtg acc tca gga g ga agg gtg acc ctc cag<br>Ala Gln Pro Ser Pro Val Val Thr Ser Gly G ly Arg Val Thr Leu Gln<br>          130                    135                  140 | 612 |
| tgt gag tca cag gtg gca ttt ggc ggc ttc a tt ctg tgt aag gaa gga<br>Cys Glu Ser Gln Val Ala Phe Gly Gly Phe I le Leu Cys Lys Glu Gly<br>             145                    150                 155 | 660 |
| gaa gat gaa cac cca caa tgc ctg aac tcc c ag ccc cat gcc cgt ggg<br>Glu Asp Glu His Pro Gln Cys Leu Asn Ser G ln Pro His Ala Arg Gly<br>160                   165                    170                 175 | 708 |
| tcg tcc cgc gcc atc ttc tcc gtg ggc ccc g tg agc ccg aat cgc agg<br>Ser Ser Arg Ala Ile Phe Ser Val Gly Pro V al Ser Pro Asn Arg Arg<br>               180                    185                 190 | 756 |
| tgg tcg cac agg tgc tat ggt tat gac ttg a ac tct ccc tat gtg tgg<br>Trp Ser His Arg Cys Tyr Gly Tyr Asp Leu A sn Ser Pro Tyr Val Trp<br>             195                    200                 205 | 804 |
| tct tca ccc agt gat ctc ctg gag ctc ctg g tc cca ggt gtt tct aag<br>Ser Ser Pro Ser Asp Leu Leu Glu Leu Leu V al Pro Gly Val Ser Lys<br>          210                    215                  220 | 852 |
| aag cca tca ctc tca gtg cag ccg ggt cct g tc gtg gcc cct ggg gaa<br>Lys Pro Ser Leu Ser Val Gln Pro Gly Pro V al Val Ala Pro Gly Glu<br>          225                    230                 235 | 900 |
| agc ctg acc ctc cag tgt gtc tct gat gtc g gc tat gac aga ttt gtt<br>Ser Leu Thr Leu Gln Cys Val Ser Asp Val G ly Tyr Asp Arg Phe Val<br>240                   245                    250                 255 | 948 |
| ctg tac aag gag ggg gaa cgt gac ctt cgc c ag ctc cct ggc cgg cag<br>Leu Tyr Lys Glu Gly Glu Arg Asp Leu Arg G ln Leu Pro Gly Arg Gln<br>               260                    265                 270 | 996 |
| ccc cag gct ggg ctc tcc cag gcc aac ttc a cc ctg ggc cct gtg agc<br>Pro Gln Ala Gly Leu Ser Gln Ala Asn Phe T hr Leu Gly Pro Val Ser<br>          275                    280                 285 | 1044 |
| cgc tcc tac ggg ggc cag tac aga tgc tac g gt gca tac aac ctc tcc<br>Arg Ser Tyr Gly Gly Gln Tyr Arg Cys Tyr G ly Ala Tyr Asn Leu Ser<br>          290                    295                 300 | 1092 |
| tcc gag tgg tcg gcc ccc agc gac ccc ctg g ac atc ctg atc aca gga<br>Ser Glu Trp Ser Ala Pro Ser Asp Pro Leu A sp Ile Leu Ile Thr Gly<br>          305                    310                 315 | 1140 |
| cag atc cat ggc aca ccc ttc atc tca gtg c ag cca ggc ccc aca gtg<br>Gln Ile His Gly Thr Pro Phe Ile Ser Val G ln Pro Gly Pro Thr Val<br>320                   325                    330                 335 | 1188 |

```
gcc tca gga gag aac gtg acc ctg ctg tgt c ag tca tgg cgg cag ttc      1236
Ala Ser Gly Glu Asn Val Thr Leu Leu Cys G ln Ser Trp Arg Gln Phe
                    340                 345                 350 cac act ttc ctt ctg acc aag gcg gga gca g ct gat gcc cca ctc cgt      1284
His Thr Phe Leu Leu Thr Lys Ala Gly Ala A la Asp Ala Pro Leu Arg
                355                 360                 365 cta aga tca ata cac gaa tat cct aag tac c ag gct gaa ttc ccc atg      1332
Leu Arg Ser Ile His Glu Tyr Pro Lys Tyr G ln Ala Glu Phe Pro Met
            370                 375                 380 agt cct gtg acc tca gcc cac gcg ggg acc t ac agg tgc tac ggc tca      1380
Ser Pro Val Thr Ser Ala His Ala Gly Thr T yr Arg Cys Tyr Gly Ser
        385                 390                 395 ctc aac tcc gac ccc tac ctg ctg tct cac c cc agt gag ccc ctg gag      1428
Leu Asn Ser Asp Pro Tyr Leu Leu Ser His P ro Ser Glu Pro Leu Glu
400                 405                 410                 415 ctc gtg gtc tca gga ccc tcc atg ggt tcc a gc ccc cca ccc acc ggt      1476
Leu Val Val Ser Gly Pro Ser Met Gly Ser S er Pro Pro Pro Thr Gly
                    420                 425                 430 ccc atc tcc aca cct gca ggc cct gag gac c ag ccc ctc acc ccc act      1524
Pro Ile Ser Thr Pro Ala Gly Pro Glu Asp G ln Pro Leu Thr Pro Thr
                435                 440                 445 ggg tcg gat ccc caa agt ggt ctg gga agg c ac ctg ggg gtt gtg atc      1572
Gly Ser Asp Pro Gln Ser Gly Leu Gly Arg H is Leu Gly Val Val Ile
            450                 455                 460 ggc atc ttg gtg gcc gtc gtc cta ctg ctc c tc ctc ctc ctc ctc         1620
Gly Ile Leu Val Ala Val Val Leu Leu Leu L eu Leu Leu Leu Leu Leu
        465                 470                 475 ttc ctc atc ctc cga cat cga cgt cag ggc a aa cac tgg aca tcg acc      1668
Phe Leu Ile Leu Arg His Arg Arg Gln Gly L ys His Trp Thr Ser Thr
480                 485                 490                 495 cag aga aag gct gat ttc caa cat cct gca g gg gct gtg ggg cca gag      1716
Gln Arg Lys Ala Asp Phe Gln His Pro Ala G ly Ala Val Gly Pro Glu
                    500                 505                 510 ccc aca gac aga ggc ctg cag tgg agg tcc a gc cca gct gcc gac gcc      1764
Pro Thr Asp Arg Gly Leu Gln Trp Arg Ser S er Pro Ala Ala Asp Ala
                515                 520                 525 cag gaa gaa aac ctc tat gct gcc gtg aag g ac aca cag cct gaa gat      1812
Gln Glu Glu Asn Leu Tyr Ala Ala Val Lys A sp Thr Gln Pro Glu Asp
            530                 535                 540 ggg gtg gag atg gac act cgg gct gct gca t ct gaa gcc ccc cag gat      1860
Gly Val Glu Met Asp Thr Arg Ala Ala Ala S er Glu Ala Pro Gln Asp
        545                 550                 555 gtg acc tac gcc cag ctg cac agc ttg acc c tc aga cgg aag gca act      1908
Val Thr Tyr Ala Gln Leu His Ser Leu Thr L eu Arg Arg Lys Ala Thr
560                 565                 570                 575 gag cct cct cca tcc cag gaa agg gaa cct c ca gct gag ccc agc atc      1956
Glu Pro Pro Pro Ser Gln Glu Arg Glu Pro P ro Ala Glu Pro Ser Ile
                    580                 585                 590 tac gcc acc ctg gcc atc cac tag cccggagggt a cgcagactc cacactcagt   2010
Tyr Ala Thr Leu Ala Ile His
                595 agaaggagac tcaggactgc tgaaggcacg ggagctgccc ccagtggaca c caatgaacc    2070 ccagtcagcc tggaccccta caaagacca tgaggagatg ctgggaactt t gggactcac    2130 ttgattctgc agtcgaaata actaatatcc ctacatttt taattaaagc a acagacttc    2190 tcaataaaag caggtcgtct cgttccaatc t                                   2221
```

```
<210> SEQ ID NO 10
<211> LENGTH: 598
<212> TYPE: PRT
<213> ORGANISM: human

<400> SEQUENCE: 10

Met Thr Pro Ile Val Thr Val Leu Ile Cys Leu Gly Leu Ser Leu Gly
 1               5                  10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala Tyr Asn Leu Ser Ser
    290                 295                 300

Glu Trp Ser Ala Pro Ser Asp Pro Leu Asp Ile Leu Ile Thr Gly Gln
305                 310                 315                 320

Ile His Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380
```

-continued

```
Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Ile Gly
450                 455                 460

Ile Leu Val Ala Val Val Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys Asp Thr Gln Pro Glu Asp Gly
530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
                580                 585                 590

Ala Thr Leu Ala Ile His
            595
```

<210> SEQ ID NO 11
<211> LENGTH: 2446
<212> TYPE: DNA
<213> ORGANISM: human
<220> FEATURE:
<221> NAME/KEY: CDS
<222> LOCATION: (171)..(1040)

<400> SEQUENCE: 11

```
cgcagctcaa cctgagctac acagccagat gcgagatgct tctctgctga tctgagtctg     60
cctgcagcat ggaccttggt cttccctgaa gcatctccag ggctggaggg acgactgcca    120
tgcacctagg gcttatccat ccgcagagca gggcagtggg aggagacgct atg acc       176
                                                        Met Thr
                                                         1 ccc atc ctc acg gtc ctg atc tgt ctc ggg ctg agt ctg ggc ccc cgg     224
Pro Ile Leu Thr Val Leu Ile Cys Leu Gly Leu Ser Leu Gly Pro Arg
         5                  10                  15 acc cac gtg cag gca ggg acc ctc ccc aag ccc aca ctc tgg gct gag     272
Thr His Val Gln Ala Gly Thr Leu Pro Lys Pro Thr Leu Trp Ala Glu
     20                  25                  30 cca ggc tct gtg atc acc cag ggg agt ccc gtg acc ctc tgg tgt cag     320
Pro Gly Ser Val Ile Thr Gln Gly Ser Pro Val Thr Leu Trp Cys Gln
 35                  40                  45                  50 ggg atc ctg gag acc cag gag tac cgt ctg tat aga gaa aag aaa aca     368
Gly Ile Leu Glu Thr Gln Glu Tyr Arg Leu Tyr Arg Glu Lys Lys Thr
                 55                  60                  65
```

-continued

| | | |
|---|---|---|
| gca ccc tgg att aca cgg atc cca cag gag a tt gtg aag aag ggc cag<br>Ala Pro Trp Ile Thr Arg Ile Pro Gln Glu I le Val Lys Lys Gly Gln<br>        70                  75                    80 | | 416 |
| ttc ccc atc ccg tcc atc acc tgg gaa cac a cc ggg cgg tat cgc tgt<br>Phe Pro Ile Pro Ser Ile Thr Trp Glu His T hr Gly Arg Tyr Arg Cys<br>            85                  90                95 | | 464 |
| ttc tac ggt agc cac act gca ggc tgg tca g ag ccc agt gac ccc ctg<br>Phe Tyr Gly Ser His Thr Ala Gly Trp Ser G lu Pro Ser Asp Pro Leu<br>    100                 105                 110 | | 512 |
| gag ctg gtg gtg aca gga gcc tac atc aaa c cc acc ctc tcg gct cta<br>Glu Leu Val Val Thr Gly Ala Tyr Ile Lys P ro Thr Leu Ser Ala Leu<br>115                 120                 125                 130 | | 560 |
| ccc agc cct gtg gtg acc tca gga ggg aac g tg acc ctc cat tgt gtc<br>Pro Ser Pro Val Val Thr Ser Gly Gly Asn V al Thr Leu His Cys Val<br>                135                 140                 145 | | 608 |
| tca cag gtg gca ttt ggc agc ttc att ctg t gt aag gaa gga gaa gat<br>Ser Gln Val Ala Phe Gly Ser Phe Ile Leu C ys Lys Glu Gly Glu Asp<br>        150                 155                 160 | | 656 |
| gaa cac cca caa tgc ctg aac tca cag ccc c gt acc cat ggg tgg tcc<br>Glu His Pro Gln Cys Leu Asn Ser Gln Pro A rg Thr His Gly Trp Ser<br>            165                 170                 175 | | 704 |
| cgg gcc atc ttc tct gtg ggc ccc gtg agc c cg agt cgc agg tgg tcg<br>Arg Ala Ile Phe Ser Val Gly Pro Val Ser P ro Ser Arg Arg Trp Ser<br>    180                 185                 190 | | 752 |
| tac agg tgc tat gct tat gac tcg aac tct c cc cat gtg tgg tct cta<br>Tyr Arg Cys Tyr Ala Tyr Asp Ser Asn Ser P ro His Val Trp Ser Leu<br>195                 200                 205                 210 | | 800 |
| ccc agt gat ctc ctg gag ctc ctg gtc cca g ga gca gct gag acc ctc<br>Pro Ser Asp Leu Leu Glu Leu Leu Val Pro G ly Ala Ala Glu Thr Leu<br>                215                 220                 225 | | 848 |
| agc cca cca caa aac aag tcc gat tcc aag g ct gga gca gct aac acc<br>Ser Pro Pro Gln Asn Lys Ser Asp Ser Lys A la Gly Ala Ala Asn Thr<br>        230                 235                 240 | | 896 |
| ctc agc cca tca caa aac aag act gcc tca c ac ccc cag gat tac aca<br>Leu Ser Pro Ser Gln Asn Lys Thr Ala Ser H is Pro Gln Asp Tyr Thr<br>            245                 250                 255 | | 944 |
| gtg gag aat ctc atc cgc atg ggc ata gct g gc ttg gtc ctg gtg gtc<br>Val Glu Asn Leu Ile Arg Met Gly Ile Ala G ly Leu Val Leu Val Val<br>    260                 265                 270 | | 992 |
| ctc ggg att ctg cta ttt gag gct cag cac a gc cag aga agc ctc tga<br>Leu Gly Ile Leu Leu Phe Glu Ala Gln His S er Gln Arg Ser Leu<br>275                 280                 285 | | 1040 |
| gatgcagccg ggaggtgaac agcagagaga agaatgtacc cttcagagtg g tggagcctt | | 1100 |
| gggaacagat ctgatgatgc caggaggttc cgggagacaa tttagggctg a tgctatctg | | 1160 |
| gactgtctgc caatcatttt tagagggagg aatcagtgtt ggattgcaga g acattttct | | 1220 |
| ggagtgatcc atgaaggacc attaacatgt gtaccttttc ctctctatta a tgttgactt | | 1280 |
| cccttggttg gatcctcttc tttccccacc cccagacaga catgaggcta c atcccacat | | 1340 |
| ggcagcgttg gtccacacc tctgcacatc tgtgtgctct ggtccatggt g tgtaacaca | | 1400 |
| gtcttcttta ttactcattg ccatactccc tggtgtgctt tactgagcct c catctcttc | | 1460 |
| aattcagagt tccaaacgtg cttcagtaac taaatcaatg ggagagtatc g gatttcaac | | 1520 |
| caggaaaaga taaatccacc ctgatgccct gacaccctct ctgaaccta c gagcccttc | | 1580 |
| cctcttctc acatgctacc tgtgcagctt ctccttagat cattgtgtaa c catcactgc | | 1640 |
| catcctgttc cacacatggt catcacccta cacccattca gcagccactc c ccattccct | | 1700 |
| cttccctcca gcacctgcta accacaaatg tgctttctgt ctctacggat t tgcctattc | | 1760 |

-continued

```
tgtctgaaaa catttcaatc tcctttgacc tgtgagctcc tcacttcgag a cttcctgcc        1820 tttccaggca gaaccaaagt acaccacgtc aaaagcaatg ataggcattt g cagtgtgtt        1880 ggtgatccac gaaaggaaaa tcacggaagc aggatagaaa tccagctgca g acaagacct        1940 caggtcgatg aatcttgaca agcagttgag ctgttttttt ctactcacct a ggacagtca        2000 ggcagaagta tgcaaaatga ctggggctga ttcttttctg aattgtcgca a acagcaaga        2060 ggacttgagt cctagcatta aagagttcaa catgtctagg tccaagacca c tgttgtgtt        2120 tgaaggatgt aaaaccctgc tgcataggat ggaatatttg gagggaggat c ctgaaaaac        2180 atgagggatc aaatagtcct caactttcta ggacaaaggg agcagctatt t gccatctac        2240 cctccagaat aaagaaatct tatcattcac catctaccct ctagaataaa g aaatcttat        2300 cattcgccat ctaccctgta gaataaagaa atcttatcat tcaccgtcta c cctctagag        2360 taaacaaatc ttatcattca ccatctaccc tctagaataa agaaatctta t cattcgcca        2420 tctaccctct agaataaaga aatctt                                              2446
```

<210> SEQ ID NO 12
<211> LENGTH: 289
<212> TYPE: PRT
<213> ORGANISM: human

<400> SEQUENCE: 12

```
Met Thr Pro Ile Leu Thr Val Leu Ile Cys L eu Gly Leu Ser Leu Gly
  1               5                  10                  15

Pro Arg Thr His Val Gln Ala Gly Thr Leu P ro Lys Pro Thr Leu Trp
             20                  25                  30

Ala Glu Pro Gly Ser Val Ile Thr Gln Gly S er Pro Val Thr Leu Trp
         35                  40                  45

Cys Gln Gly Ile Leu Glu Thr Gln Glu Tyr A rg Leu Tyr Arg Glu Lys
     50                  55                  60

Lys Thr Ala Pro Trp Ile Thr Arg Ile Pro G ln Glu Ile Val Lys Lys
 65                  70                  75                  80

Gly Gln Phe Pro Ile Pro Ser Ile Thr Trp G lu His Thr Gly Arg Tyr
                 85                  90                  95

Arg Cys Phe Tyr Gly Ser His Thr Ala Gly T rp Ser Glu Pro Ser Asp
            100                 105                 110

Pro Leu Glu Leu Val Val Thr Gly Ala Tyr I le Lys Pro Thr Leu Ser
        115                 120                 125

Ala Leu Pro Ser Pro Val Val Thr Ser Gly G ly Asn Val Thr Leu His
    130                 135                 140

Cys Val Ser Gln Val Ala Phe Gly Ser Phe I le Leu Cys Lys Glu Gly
145                 150                 155                 160

Glu Asp Glu His Pro Gln Cys Leu Asn Ser G ln Pro Arg Thr His Gly
                165                 170                 175

Trp Ser Arg Ala Ile Phe Ser Val Gly Pro V al Ser Pro Ser Arg Arg
            180                 185                 190

Trp Ser Tyr Arg Cys Tyr Ala Tyr Asp Ser A sn Ser Pro His Val Trp
        195                 200                 205

Ser Leu Pro Ser Asp Leu Leu Glu Leu Leu V al Pro Gly Ala Ala Glu
    210                 215                 220

Thr Leu Ser Pro Pro Gln Asn Lys Ser Asp S er Lys Ala Gly Ala Ala
225                 230                 235                 240

Asn Thr Leu Ser Pro Ser Gln Asn Lys Thr A la Ser His Pro Gln Asp
                245                 250                 255
```

```
Tyr Thr Val Glu Asn Leu Ile Arg Met Gly I le Ala Gly Leu Val Leu
            260                 265                 270

Val Val Leu Gly Ile Leu Leu Phe Glu Ala G ln His Ser Gln Arg Ser
        275                 280                 285

Leu

<210> SEQ ID NO 13
<211> LENGTH: 1910
<212> TYPE: DNA
<213> ORGANISM: human
<220> FEATURE:
<221> NAME/KEY: CDS
<222> LOCATION: (183)..(1652)

<400> SEQUENCE: 13
ctcactgcca cacgcagctc aacctgagct acacagccag atgcgagatg c ttctctgct      60 gatctgagtc tgcctgcagc atggaccttg gtcttccctg aagcatctcc a gggctggag    120 ggacgactgc catgcaccga gggctcatcc atccgcagag cagggcagtg g gaggagacg    180 ct atg acc ccc atc gtc aca gtc ctg atc tg t ctc agg ctg agt ctg       227
   Met Thr Pro Ile Val Thr Val Leu Ile  Cys Leu Arg Leu Ser Leu
     1               5                  10                  15 ggc ccc cgg acc cac gtg cag gca ggg acc c tc ccc aag ccc aca ctc     275
Gly Pro Arg Thr His Val Gln Ala Gly Thr L eu Pro Lys Pro Thr Leu
                20                  25                  30 tgg gct gag cca ggc tct gtg atc acc cag g gg agt ccc gtg acc ctc     323
Trp Ala Glu Pro Gly Ser Val Ile Thr Gln G ly Ser Pro Val Thr Leu
            35                  40                  45 tgg tgt cag ggg atc ctg gag acc cag gag t ac cgt ctg tat aga gaa     371
Trp Cys Gln Gly Ile Leu Glu Thr Gln Glu T yr Arg Leu Tyr Arg Glu
        50                  55                  60 aag aaa aca gca ccc tgg att aca cgg atc c ca cag gag att gtg aag     419
Lys Lys Thr Ala Pro Trp Ile Thr Arg Ile P ro Gln Glu Ile Val Lys
    65                  70                  75 aag ggc cag ttc ccc atc cca tcc atc acc t gg gaa cac aca ggg cgg     467
Lys Gly Gln Phe Pro Ile Pro Ser Ile Thr T rp Glu His Thr Gly Arg
 80                  85                  90                  95 tat cgc tgt ttc tac ggt agc cac act gca g gc tgg tca gag ccc agt     515
Tyr Arg Cys Phe Tyr Gly Ser His Thr Ala G ly Trp Ser Glu Pro Ser
                100                 105                 110 gac ccc ctg gag ctg gtg gtg aca gga gcc t ac atc aaa ccc acc ctc     563
Asp Pro Leu Glu Leu Val Val Thr Gly Ala T yr Ile Lys Pro Thr Leu
            115                 120                 125 tca gct cta ccc agc cct gtg gtg acc tca g ga ggg aac gtg acc ctc     611
Ser Ala Leu Pro Ser Pro Val Val Thr Ser G ly Gly Asn Val Thr Leu
        130                 135                 140 cat tgt gtc tca cag gtg gca ttt ggc agc t tc att ctg tgt aag gaa     659
His Cys Val Ser Gln Val Ala Phe Gly Ser P he Ile Leu Cys Lys Glu
    145                 150                 155 gga gaa gat gaa cac cca caa tgc ctg aac t ca cag ccc cgt acc cat     707
Gly Glu Asp Glu His Pro Gln Cys Leu Asn S er Gln Pro Arg Thr His
160                 165                 170                 175 ggg tgg tcc cgg gcc atc ttc tct gtg ggc c cc gtg agc ccg agt cgc     755
Gly Trp Ser Arg Ala Ile Phe Ser Val Gly P ro Val Ser Pro Ser Arg
                180                 185                 190 agg tgg tcg tac agg tgc tat gct tat gac t cg aac tct ccc cat gtg     803
Arg Trp Ser Tyr Arg Cys Tyr Ala Tyr Asp S er Asn Ser Pro His Val
            195                 200                 205
```

```
                                              -continued tgg tct cta ccc agt gat ctc ctg gag ctc c tg gtc cta ggt gtt tct      851
Trp Ser Leu Pro Ser Asp Leu Leu Glu Leu L eu Val Leu Gly Val Ser
            210                 215                 220 aag aag cca tca ctc tca gtg cag cca ggt c ct ata gtg gcc cct ggg      899
Lys Lys Pro Ser Leu Ser Val Gln Pro Gly P ro Ile Val Ala Pro Gly
            225                 230                 235 gag agc ctg acc ctc cag tgt gtt tct gat g tc agc tac gac aga ttt      947
Glu Ser Leu Thr Leu Gln Cys Val Ser Asp V al Ser Tyr Asp Arg Phe
240                 245                 250                 255 gtt ctg tat aag gag gga gaa cgt gac ttc c tc cag ctc cct ggc cca      995
Val Leu Tyr Lys Glu Gly Glu Arg Asp Phe L eu Gln Leu Pro Gly Pro
            260                 265                 270 cag ccc cag gct ggg ctc tcc cag gcc aac t tc acc ctg ggc cct gtg      1043
Gln Pro Gln Ala Gly Leu Ser Gln Ala Asn P he Thr Leu Gly Pro Val
            275                 280                 285 agc cgc tcc tac ggg ggc cag tac aga tgc t cc ggt gca tac aac ctc      1091
Ser Arg Ser Tyr Gly Gly Gln Tyr Arg Cys S er Gly Ala Tyr Asn Leu
            290                 295                 300 tcc tcc gag tgg tcg gcc ccc agc gac ccc c tg gac atc ctg atc gca      1139
Ser Ser Glu Trp Ser Ala Pro Ser Asp Pro L eu Asp Ile Leu Ile Ala
305                 310                 315 gga cag ttc cgt ggc aga ccc ttc atc tcg g tg cat ccg ggc ccc acg      1187
Gly Gln Phe Arg Gly Arg Pro Phe Ile Ser V al His Pro Gly Pro Thr
320                 325                 330                 335 gtg gcc tca gga gag aac gtg acc ctg ctg t gt cag tca tgg ggg ccg      1235
Val Ala Ser Gly Glu Asn Val Thr Leu Leu C ys Gln Ser Trp Gly Pro
            340                 345                 350 ttc cac act ttc ctt ctg acc aag gcg gga g ca gct gat gcc ccc ctc      1283
Phe His Thr Phe Leu Leu Thr Lys Ala Gly A la Ala Asp Ala Pro Leu
            355                 360                 365 cgt ctc aga tca ata cac gaa tat cct aag t ac cag gct gaa ttc cct      1331
Arg Leu Arg Ser Ile His Glu Tyr Pro Lys T yr Gln Ala Glu Phe Pro
            370                 375                 380 atg agt cct gtg acc tca gcc cac tcg ggg a cc tac agg tgc tac ggc      1379
Met Ser Pro Val Thr Ser Ala His Ser Gly T hr Tyr Arg Cys Tyr Gly
385                 390                 395 tca ctc agc tcc aac ccc tac ctg ctg tct c ac ccc agt gac tcc ctg      1427
Ser Leu Ser Ser Asn Pro Tyr Leu Leu Ser H is Pro Ser Asp Ser Leu
400                 405                 410                 415 gag ctc atg gtc tca gga gca gct gag acc c tc agc cca cca caa aac      1475
Glu Leu Met Val Ser Gly Ala Ala Glu Thr L eu Ser Pro Pro Gln Asn
            420                 425                 430 aag tcc gat tcc aag gct gga gca gct aac a cc ctc agc cca tca caa      1523
Lys Ser Asp Ser Lys Ala Gly Ala Ala Asn T hr Leu Ser Pro Ser Gln
            435                 440                 445 aac aag act gcc tca cac ccc cag gat tac a ca gtg gag aat ctc atc      1571
Asn Lys Thr Ala Ser His Pro Gln Asp Tyr T hr Val Glu Asn Leu Ile
            450                 455                 460 cgc atg ggc ata gct ggc ttg gtc ctg gtg g tc ctc ggg att ctg cta      1619
Arg Met Gly Ile Ala Gly Leu Val Leu Val V al Leu Gly Ile Leu Leu
465                 470                 475 ttt gag gct cag cac agc cag aga agc ctc t ga gatgcagccg ggaggtgaac   1672
Phe Glu Ala Gln His Ser Gln Arg Ser Leu
480                 485 agcagagaga agaatgtacc cttcagagtg gtggagcctt gggaacagat ctgatgatgc    1732
caggaggttc cgggagacaa tttagggctg atgttatctg gactgtctgc caatcatttt    1792
tagagggagg aatcagtgtt ggattgcaga gacattttct ggagtgatcc atgaaggacc    1852
attaacatgt gataccttc ctctctatta atgttgactt cccttggttg gatcctct       1910
```

```
<210> SEQ ID NO 14
<211> LENGTH: 489
<212> TYPE: PRT
<213> ORGANISM: human

<400> SEQUENCE: 14

Met Thr Pro Ile Val Thr Val Leu Ile Cys Leu Arg Leu Ser Leu Gly
 1               5                  10                  15

Pro Arg Thr His Val Gln Ala Gly Thr Leu Pro Lys Pro Thr Leu Trp
                20                  25                  30

Ala Glu Pro Gly Ser Val Ile Thr Gln Gly Ser Pro Val Thr Leu Trp
            35                  40                  45

Cys Gln Gly Ile Leu Glu Thr Gln Glu Tyr Arg Leu Tyr Arg Glu Lys
        50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Gly Glu
225                 230                 235                 240

Ser Leu Thr Leu Gln Cys Val Ser Asp Val Ser Tyr Asp Arg Phe Val
                245                 250                 255

Leu Tyr Lys Glu Gly Glu Arg Asp Phe Leu Gln Leu Pro Gly Pro Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Ser Gly Ala Tyr Asn Leu Ser
    290                 295                 300

Ser Glu Trp Ser Ala Pro Ser Asp Pro Leu Asp Ile Leu Ile Ala Gly
305                 310                 315                 320

Gln Phe Arg Gly Arg Pro Phe Ile Ser Val His Pro Gly Pro Thr Val
                325                 330                 335

Ala Ser Gly Glu Asn Val Thr Leu Leu Cys Gln Ser Trp Gly Pro Phe
            340                 345                 350

His Thr Phe Leu Leu Thr Lys Ala Gly Ala Ala Asp Ala Pro Leu Arg
        355                 360                 365

Leu Arg Ser Ile His Glu Tyr Pro Lys Tyr Gln Ala Glu Phe Pro Met
    370                 375                 380
```

```
Ser Pro Val Thr Ser Ala His Ser Gly Thr Tyr Arg Cys Tyr Gly Ser
385                 390                 395                 400

Leu Ser Ser Asn Pro Tyr Leu Leu Ser His Pro Ser Asp Ser Leu Glu
                405                 410                 415

Leu Met Val Ser Gly Ala Ala Glu Thr Leu Ser Pro Pro Gln Asn Lys
                420                 425                 430

Ser Asp Ser Lys Ala Gly Ala Ala Asn Thr Leu Ser Pro Ser Gln Asn
            435                 440                 445

Lys Thr Ala Ser His Pro Gln Asp Tyr Thr Val Glu Asn Leu Ile Arg
        450                 455                 460

Met Gly Ile Ala Gly Leu Val Leu Val Val Leu Gly Ile Leu Leu Phe
465                 470                 475                 480

Glu Ala Gln His Ser Gln Arg Ser Leu
                485

<210> SEQ ID NO 15
<211> LENGTH: 1725
<212> TYPE: DNA
<213> ORGANISM: human
<220> FEATURE:
<221> NAME/KEY: CDS
<222> LOCATION: (40)..(1491)

<400> SEQUENCE: 15
ctcatccatc cgcagagcag ggcagtggga ggagacgcc atg acc cc c atc ctc     54
                                          Met Thr Pro Ile Leu
                                            1               5 acg gtc ctg atc tgt ctc ggg ctg agt ctg g gc ccc agg acc cac gtg  102
Thr Val Leu Ile Cys Leu Gly Leu Ser Leu G ly Pro Arg Thr His Val
             10                  15                  20 cag gca ggg cac ctc ccc aag ccc acc ctc t gg gct gag cca ggc tct  150
Gln Ala Gly His Leu Pro Lys Pro Thr Leu T rp Ala Glu Pro Gly Ser
         25                  30                  35 gtg atc atc cag gga agt cct gtg acc ctc a gg tgt cag ggg agc ctt  198
Val Ile Ile Gln Gly Ser Pro Val Thr Leu A rg Cys Gln Gly Ser Leu
     40                  45                  50 cag gct gag gag tac cat cta tat agg gaa a ac aaa tca gca tcc tgg  246
Gln Ala Glu Glu Tyr His Leu Tyr Arg Glu A sn Lys Ser Ala Ser Trp
 55                  60                  65 gtt aga cgg ata caa gag cct ggg aag aat g gc cag ttc ccc atc cca  294
Val Arg Arg Ile Gln Glu Pro Gly Lys Asn G ly Gln Phe Pro Ile Pro
 70                  75                  80                  85 tcc atc acc tgg gaa cac gca ggg cgg tat c ac tgt cag tac tac agc  342
Ser Ile Thr Trp Glu His Ala Gly Arg Tyr H is Cys Gln Tyr Tyr Ser
             90                  95                 100 cac aat cac tca tca gag tac agt gac ccc c tg gag ctg gtg gtg aca  390
His Asn His Ser Ser Glu Tyr Ser Asp Pro L eu Glu Leu Val Val Thr
            105                 110                 115 gga gcc tac agc aaa ccc acc ctc tca gct c tg ccc agc cct gtg gtg  438
Gly Ala Tyr Ser Lys Pro Thr Leu Ser Ala L eu Pro Ser Pro Val Val
            120                 125                 130 acc tta gga ggg aac gtg acc ctc cag tgt g tc tca cag gtg gca ttt  486
Thr Leu Gly Gly Asn Val Thr Leu Gln Cys V al Ser Gln Val Ala Phe
        135                 140                 145 gac ggc ttc att ctg tgt aag gaa gga gaa g at gaa cac cca caa cgc  534
Asp Gly Phe Ile Leu Cys Lys Glu Gly Glu A sp Glu His Pro Gln Arg
150                 155                 160                 165 ctg aac tcc cat tcc cat gcc cgt ggg tgg t cc tgg gcc atc ttc tcc  582
Leu Asn Ser His Ser His Ala Arg Gly Trp S er Trp Ala Ile Phe Ser
                170                 175                 180
```

```
gtg ggc ccc gtg agc ccg agt cgc agg tgg t cg tac agg tgc tat gct      630
Val Gly Pro Val Ser Pro Ser Arg Arg Trp S er Tyr Arg Cys Tyr Ala
            185                 190                 195 tat gac tcg aac tct ccc tat gtg tgg tct c ta ccc agt gat ctc ctg      678
Tyr Asp Ser Asn Ser Pro Tyr Val Trp Ser L eu Pro Ser Asp Leu Leu
            200                 205                 210 gag ctc ctg gtc cca ggt gtt tct aag aag c ca tca ctc tca gtg cag      726
Glu Leu Leu Val Pro Gly Val Ser Lys Lys P ro Ser Leu Ser Val Gln
            215                 220                 225 cca ggt cct atg gtg gcc ccc ggg gag agc c tg acc ctc cag tgt gtc      774
Pro Gly Pro Met Val Ala Pro Gly Glu Ser L eu Thr Leu Gln Cys Val
230                 235                 240                 245 tct gat gtc ggc tac gac aga ttt gtt ctg t at aag gag gga gaa cgt      822
Ser Asp Val Gly Tyr Asp Arg Phe Val Leu T yr Lys Glu Gly Glu Arg
                250                 255                 260 gac ttc ctc cag cgc cct ggt tgg cag ccc c ag gct ggg ctc tcc cag      870
Asp Phe Leu Gln Arg Pro Gly Trp Gln Pro G ln Ala Gly Leu Ser Gln
            265                 270                 275 gcc aac ttc acc ctg ggc cct gtg agc ccc t cc cac ggg ggc cag tac      918
Ala Asn Phe Thr Leu Gly Pro Val Ser Pro S er His Gly Gly Gln Tyr
            280                 285                 290 aga tgc tac agt gca cac aac ctc tcc tcc g ag tgg tcg gcc ccc agt      966
Arg Cys Tyr Ser Ala His Asn Leu Ser Ser G lu Trp Ser Ala Pro Ser
295                 300                 305 gac ccc ctg gac atc ctg atc aca gga cag t tc tat gac aga ccc tct     1014
Asp Pro Leu Asp Ile Leu Ile Thr Gly Gln P he Tyr Asp Arg Pro Ser
310                 315                 320                 325 ctc tcg gtg cag ccg gtc ccc aca gta gcc c ca gga aag aac gtg acc     1062
Leu Ser Val Gln Pro Val Pro Thr Val Ala P ro Gly Lys Asn Val Thr
                330                 335                 340 ctg ctg tgt cag tca cgg ggg cag ttc cac a ct ttc ctt ctg acc aag     1110
Leu Leu Cys Gln Ser Arg Gly Gln Phe His T hr Phe Leu Leu Thr Lys
            345                 350                 355 gag ggg gca ggc cat ccc cca ctg cat ctg a ga tca gag cac caa gct     1158
Glu Gly Ala Gly His Pro Pro Leu His Leu A rg Ser Glu His Gln Ala
            360                 365                 370 cag cag aac cag gct gaa ttc cgc atg ggt c ct gtg acc tca gcc cac     1206
Gln Gln Asn Gln Ala Glu Phe Arg Met Gly P ro Val Thr Ser Ala His
            375                 380                 385 gtg ggg acc tac aga tgc tac agc tca ctc a gc tcc aac ccc tac ctg     1254
Val Gly Thr Tyr Arg Cys Tyr Ser Ser Leu S er Ser Asn Pro Tyr Leu
390                 395                 400                 405 ctg tct ctc ccc agt gac ccc ctg gag ctc g tg gtc tca gaa gca gct     1302
Leu Ser Leu Pro Ser Asp Pro Leu Glu Leu V al Val Ser Glu Ala Ala
            410                 415                 420 gag acc ctc agc cca tca caa aac aag aca g ac tcc acg act aca tcc     1350
Glu Thr Leu Ser Pro Ser Gln Asn Lys Thr A sp Ser Thr Thr Thr Ser
            425                 430                 435 cta ggc caa cac ccc cag gat tac aca gtg g ag aat ctc atc cgc atg     1398
Leu Gly Gln His Pro Gln Asp Tyr Thr Val G lu Asn Leu Ile Arg Met
            440                 445                 450 ggt gtg gct ggc ttg gtc ctg gtg gtc ctc g gg att ctg cta ttt gag     1446
Gly Val Ala Gly Leu Val Leu Val Val Leu G ly Ile Leu Leu Phe Glu
455                 460                 465 gct cag cac agc cag aga agc cta caa gat g ca gcc ggg agg tga        1491
Ala Gln His Ser Gln Arg Ser Leu Gln Asp A la Ala Gly Arg
470                 475                 480
```

-continued

```
acagcagaga ggacaatgca tccttcagcg tggtggagcc tcaggacag a tctgatgat      1551 cccaggaggc tctggaggac aatctaggac ctacattatc tggactgtat g ctggtcatt      1611 tctagagaca gcaatcaata tttgagtgta aggaaactgt ctggggtgat t cctagaaga      1671 tcattaaact gtggtacatt tttttgtcta aaaagcaggt cgtctcgttc c aag           1725
```

<210> SEQ ID NO 16
<211> LENGTH: 483
<212> TYPE: PRT
<213> ORGANISM: human

<400> SEQUENCE: 16

```
Met Thr Pro Ile Leu Thr Val Leu Ile Cys L eu Gly Leu Ser Leu Gly
 1               5                  10                  15

Pro Arg Thr His Val Gln Ala Gly His Leu P ro Lys Pro Thr Leu Trp
                20                  25                  30

Ala Glu Pro Gly Ser Val Ile Ile Gln Gly S er Pro Val Thr Leu Arg
            35                  40                  45

Cys Gln Gly Ser Leu Gln Ala Glu Glu Tyr H is Leu Tyr Arg Glu Asn
        50                  55                  60

Lys Ser Ala Ser Trp Val Arg Arg Ile Gln G lu Pro Gly Lys Asn Gly
    65                  70                  75                  80

Gln Phe Pro Ile Pro Ser Ile Thr Trp Glu H is Ala Gly Arg Tyr His
                85                  90                  95

Cys Gln Tyr Tyr Ser His Asn His Ser Ser G lu Tyr Ser Asp Pro Leu
               100                 105                 110

Glu Leu Val Val Thr Gly Ala Tyr Ser Lys P ro Thr Leu Ser Ala Leu
           115                 120                 125

Pro Ser Pro Val Val Thr Leu Gly Gly Asn V al Thr Leu Gln Cys Val
       130                 135                 140

Ser Gln Val Ala Phe Asp Gly Phe Ile Leu C ys Lys Glu Gly Glu Asp
145                 150                 155                 160

Glu His Pro Gln Arg Leu Asn Ser His Ser H is Ala Arg Gly Trp Ser
                165                 170                 175

Trp Ala Ile Phe Ser Val Gly Pro Val Ser P ro Ser Arg Arg Trp Ser
            180                 185                 190

Tyr Arg Cys Tyr Ala Tyr Asp Ser Asn Ser P ro Tyr Val Trp Ser Leu
        195                 200                 205

Pro Ser Asp Leu Leu Glu Leu Leu Val Pro G ly Val Ser Lys Lys Pro
    210                 215                 220

Ser Leu Ser Val Gln Pro Gly Pro Met Val A la Pro Gly Glu Ser Leu
225                 230                 235                 240

Thr Leu Gln Cys Val Ser Asp Val Gly Tyr A sp Arg Phe Val Leu Tyr
                245                 250                 255

Lys Glu Gly Glu Arg Asp Phe Leu Gln Arg P ro Gly Trp Gln Pro Gln
            260                 265                 270

Ala Gly Leu Ser Gln Ala Asn Phe Thr Leu G ly Pro Val Ser Pro Ser
        275                 280                 285

His Gly Gly Gln Tyr Arg Cys Tyr Ser Ala H is Asn Leu Ser Ser Glu
    290                 295                 300

Trp Ser Ala Pro Ser Asp Pro Leu Asp Ile L eu Ile Thr Gly Gln Phe
305                 310                 315                 320

Tyr Asp Arg Pro Ser Leu Ser Val Gln Pro V al Pro Thr Val Ala Pro
                325                 330                 335
```

```
Gly Lys Asn Val Thr Leu Leu Cys Gln Ser Arg Gly Gln Phe His Thr
            340                 345                 350
Phe Leu Leu Thr Lys Glu Gly Ala Gly His Pro Leu His Leu Arg
            355                 360             365
Ser Glu His Gln Ala Gln Gln Asn Gln Ala Glu Phe Arg Met Gly Pro
            370                 375                 380
Val Thr Ser Ala His Val Gly Thr Tyr Arg Cys Tyr Ser Ser Leu Ser
385                 390                 395                 400
Ser Asn Pro Tyr Leu Leu Ser Leu Pro Ser Asp Pro Leu Glu Leu Val
                405                 410                 415
Val Ser Glu Ala Ala Glu Thr Leu Ser Pro Ser Gln Asn Lys Thr Asp
            420                 425                 430
Ser Thr Thr Thr Ser Leu Gly Gln His Pro Gln Asp Tyr Thr Val Glu
            435                 440                 445
Asn Leu Ile Arg Met Gly Val Ala Gly Leu Val Leu Val Val Leu Gly
            450                 455                 460
Ile Leu Leu Phe Glu Ala Gln His Ser Gln Arg Ser Leu Gln Asp Ala
465                 470                 475                 480
Ala Gly Arg

<210> SEQ ID NO 17
<211> LENGTH: 1625
<212> TYPE: DNA
<213> ORGANISM: human
<220> FEATURE:
<221> NAME/KEY: CDS
<222> LOCATION: (30)..(1376)

<400> SEQUENCE: 17
cacagctggg gcccctggga ggagacgcc atg atc ccc acc tt c acg gct ctg          53
                                Met Ile Pro Thr Phe Thr Ala Leu
                                  1               5 ctc tgc ctc ggg ctg agt ctg ggc ccc agg a cc cac atg cag gca ggg        101
Leu Cys Leu Gly Leu Ser Leu Gly Pro Arg Thr His Met Gln Ala Gly
     10                  15                  20 ccc ctc ccc aaa ccc acc ctc tgg gct gag c ca ggc tct gtg atc agc        149
Pro Leu Pro Lys Pro Thr Leu Trp Ala Glu Pro Gly Ser Val Ile Ser
 25                  30                  35                  40 tgg ggg aac tct gtg acc atc tgg tgt cag g gg acc ctg gag gct cgg        197
Trp Gly Asn Ser Val Thr Ile Trp Cys Gln Gly Thr Leu Glu Ala Arg
                 45                  50                  55 gag tac cgt ctg gat aaa gag gaa agc cca g ca ccc tgg gac aga cag        245
Glu Tyr Arg Leu Asp Lys Glu Glu Ser Pro Ala Pro Trp Asp Arg Gln
             60                  65                  70 aac cca ctg gag ccc aag aac aag gcc aga t tc tcc atc cca tcc atg        293
Asn Pro Leu Glu Pro Lys Asn Lys Ala Arg Phe Ser Ile Pro Ser Met
         75                  80                  85 aca gag gac tat gca ggg aga tac cgc tgt t ac tat cgc agc cct gta        341
Thr Glu Asp Tyr Ala Gly Arg Tyr Arg Cys Tyr Tyr Arg Ser Pro Val
     90                  95                 100 ggc tgg tca cag ccc agt gac ccc ctg gag c tg gtg atg aca gga gcc        389
Gly Trp Ser Gln Pro Ser Asp Pro Leu Glu Leu Val Met Thr Gly Ala
105                 110                 115                 120 tac agt aaa ccc acc ctt tca gcc ctg ccg a gt cct ctt gtg acc tca        437
Tyr Ser Lys Pro Thr Leu Ser Ala Leu Pro Ser Pro Leu Val Thr Ser
                125                 130                 135 gga aag agc gtg acc ctg ctg tgt cag tca c gg agc cca atg gac act        485
Gly Lys Ser Val Thr Leu Leu Cys Gln Ser Arg Ser Pro Met Asp Thr
            140                 145                 150
```

-continued

```
ttt ctt ctg atc aag gag cgg gca gcc cat c cc cta ctg cat ctg aga        533
Phe Leu Leu Ile Lys Glu Arg Ala Ala His P ro Leu Leu His Leu Arg
        155                 160                 165 tca gag cac gga gct cag cag cac cag gct g aa ttc ccc atg agt cct        581
Ser Glu His Gly Ala Gln Gln His Gln Ala G lu Phe Pro Met Ser Pro
    170                 175                 180 gtg acc tca gtg cac ggg ggg acc tac agg t gc ttc agc tca cac ggc        629
Val Thr Ser Val His Gly Gly Thr Tyr Arg C ys Phe Ser Ser His Gly
185                 190                 195                 200 ttc tcc cac tac ctg ctg tca cac ccc agt g ac ccc ctg gag ctc ata        677
Phe Ser His Tyr Leu Leu Ser His Pro Ser A sp Pro Leu Glu Leu Ile
                205                 210                 215 gtc tca gga tcc ttg gag ggt ccc agg ccc t ca ccc aca agg tcc gtc        725
Val Ser Gly Ser Leu Glu Gly Pro Arg Pro S er Pro Thr Arg Ser Val
            220                 225                 230 tca aca gct gca ggc cct gag gac cag ccc c tc atg cct aca ggg tca        773
Ser Thr Ala Ala Gly Pro Glu Asp Gln Pro L eu Met Pro Thr Gly Ser
        235                 240                 245 gtc ccc cac agt ggt ctg aga agg cac tgg g ag gta ctg atc ggg gtc        821
Val Pro His Ser Gly Leu Arg Arg His Trp G lu Val Leu Ile Gly Val
    250                 255                 260 ttg gtg gtc tcc atc ctg ctt ctc tcc ctc c tc ctc ttc ctc ctc ctc        869
Leu Val Val Ser Ile Leu Leu Leu Ser Leu L eu Leu Phe Leu Leu Leu
265                 270                 275                 280 caa cac tgg cgt cag gga aaa cac agg aca t tg gcc cag aga cag gct        917
Gln His Trp Arg Gln Gly Lys His Arg Thr L eu Ala Gln Arg Gln Ala
                285                 290                 295 gat ttc caa cgt cct cca ggg gct gcc gag c ca gag ccc aag gac ggg        965
Asp Phe Gln Arg Pro Pro Gly Ala Ala Glu P ro Glu Pro Lys Asp Gly
            300                 305                 310 ggc cta cag agg agg tcc agc cca gct gct g ac gtc cag gga gaa aac       1013
Gly Leu Gln Arg Arg Ser Ser Pro Ala Ala A sp Val Gln Gly Glu Asn
        315                 320                 325 ttc tgt gct gcc gtg aag aac aca cag cct g ag gac ggg gtg gaa atg       1061
Phe Cys Ala Ala Val Lys Asn Thr Gln Pro G lu Asp Gly Val Glu Met
    330                 335                 340 gac act cgg cag agc cca cac gat gaa gac c cc cag gca gtg acg tat       1109
Asp Thr Arg Gln Ser Pro His Asp Glu Asp P ro Gln Ala Val Thr Tyr
345                 350                 355                 360 gcc aag gtg aaa cac tcc aga cct agg aga g aa atg gcc tct cct ccc       1157
Ala Lys Val Lys His Ser Arg Pro Arg Arg G lu Met Ala Ser Pro Pro
                365                 370                 375 tcc cca ctg tct ggg gaa ttc ctg gac aca a ag gac aga cag gca gaa       1205
Ser Pro Leu Ser Gly Glu Phe Leu Asp Thr L ys Asp Arg Gln Ala Glu
            380                 385                 390 gag gac aga cag atg gac act gag gct gct g ca tct gaa gcc ccc cag       1253
Glu Asp Arg Gln Met Asp Thr Glu Ala Ala A la Ser Glu Ala Pro Gln
        395                 400                 405 gat gtg acc tac gcc cgg ctg cac agc ttt a cc ctc aga cag aag gca       1301
Asp Val Thr Tyr Ala Arg Leu His Ser Phe T hr Leu Arg Gln Lys Ala
    410                 415                 420 act gag cct cct cca tcc cag gaa ggg gcc t ct cca gct gag ccc agt       1349
Thr Glu Pro Pro Pro Ser Gln Glu Gly Ala S er Pro Ala Glu Pro Ser
425                 430                 435                 440 gtc tat gcc act ctg gcc atc cac taa tccagggg gg acccagaccc             1396
Val Tyr Ala Thr Leu Ala Ile His
                445 cacaagccat ggagactcag gacccagaa ggcatggaag ctgcctccag t agacatcac      1456 tgaaccccag ccagcccaga ccctgacac agaccactag aagattccgg g aacgttggg     1516
```

-continued

```
agtcacctga ttctgcaaag ataaataata tccctgcatt atcaaaataa a gtagcagac    1576 ctctcaattc acaatgagtt aactgataaa acaaaacaga agtcaaaaa                 1625
```

<210> SEQ ID NO 18
<211> LENGTH: 448
<212> TYPE: PRT
<213> ORGANISM: human

<400> SEQUENCE: 18

```
Met Ile Pro Thr Phe Thr Ala Leu Leu Cys L eu Gly Leu Ser Leu Gly
  1               5                  10                  15

Pro Arg Thr His Met Gln Ala Gly Pro Leu P ro Lys Pro Thr Leu Trp
             20                  25                  30

Ala Glu Pro Gly Ser Val Ile Ser Trp Gly A sn Ser Val Thr Ile Trp
         35                  40                  45

Cys Gln Gly Thr Leu Glu Ala Arg Glu Tyr A rg Leu Asp Lys Glu Glu
     50                  55                  60

Ser Pro Ala Pro Trp Asp Arg Gln Asn Pro L eu Glu Pro Lys Asn Lys
 65                  70                  75                  80

Ala Arg Phe Ser Ile Pro Ser Met Thr Glu A sp Tyr Ala Gly Arg Tyr
                 85                  90                  95

Arg Cys Tyr Tyr Arg Ser Pro Val Gly Trp S er Gln Pro Ser Asp Pro
            100                 105                 110

Leu Glu Leu Val Met Thr Gly Ala Tyr Ser L ys Pro Thr Leu Ser Ala
        115                 120                 125

Leu Pro Ser Pro Leu Val Thr Ser Gly Lys S er Val Thr Leu Leu Cys
    130                 135                 140

Gln Ser Arg Ser Pro Met Asp Thr Phe Leu L eu Ile Lys Glu Arg Ala
145                 150                 155                 160

Ala His Pro Leu Leu His Leu Arg Ser Glu H is Gly Ala Gln Gln His
                165                 170                 175

Gln Ala Glu Phe Pro Met Ser Pro Val Thr S er Val His Gly Gly Thr
            180                 185                 190

Tyr Arg Cys Phe Ser Ser His Gly Phe Ser H is Tyr Leu Leu Ser His
        195                 200                 205

Pro Ser Asp Pro Leu Glu Leu Ile Val Ser G ly Ser Leu Glu Gly Pro
    210                 215                 220

Arg Pro Ser Pro Thr Arg Ser Val Ser Thr A la Ala Gly Pro Glu Asp
225                 230                 235                 240

Gln Pro Leu Met Pro Thr Gly Ser Val Pro H is Ser Gly Leu Arg Arg
                245                 250                 255

His Trp Glu Val Leu Ile Gly Val Leu Val V al Ser Ile Leu Leu Leu
            260                 265                 270

Ser Leu Leu Leu Phe Leu Leu Leu Gln His T rp Arg Gln Gly Lys His
        275                 280                 285

Arg Thr Leu Ala Gln Arg Gln Ala Asp Phe G ln Arg Pro Pro Gly Ala
    290                 295                 300

Ala Glu Pro Glu Pro Lys Asp Gly Gly Leu G ln Arg Arg Ser Ser Pro
305                 310                 315                 320

Ala Ala Asp Val Gln Gly Glu Asn Phe Cys A la Ala Val Lys Asn Thr
                325                 330                 335

Gln Pro Glu Asp Gly Val Glu Met Asp Thr A rg Gln Ser Pro His Asp
            340                 345                 350
```

```
Glu Asp Pro Gln Ala Val Thr Tyr Ala Lys Val Lys His Ser Arg Pro
        355                 360                 365
Arg Arg Glu Met Ala Ser Pro Pro Ser Pro Leu Ser Gly Glu Phe Leu
    370                 375                 380
Asp Thr Lys Asp Arg Gln Ala Glu Asp Arg Gln Met Asp Thr Glu
385                 390                 395                 400
Ala Ala Ala Ser Glu Ala Pro Gln Asp Val Thr Tyr Ala Arg Leu His
                405                 410                 415
Ser Phe Thr Leu Arg Gln Lys Ala Thr Glu Pro Pro Pro Ser Gln Glu
                420                 425                 430
Gly Ala Ser Pro Ala Glu Pro Ser Val Tyr Ala Thr Leu Ala Ile His
                435                 440                 445
```

<210> SEQ ID NO 19
<211> LENGTH: 2194
<212> TYPE: DNA
<213> ORGANISM: human
<220> FEATURE:
<221> NAME/KEY: CDS
<222> LOCATION: (67)..(1962)

<400> SEQUENCE: 19

```
tctctgtcct gccagcactg agggctcatc cctctgcaga gcgcggggtc a ccggaagga       60 gacgcc atg acg ccc gcc ctc aca gcc ctg ctc tgc ctt ggg ctg agt        108
       Met Thr Pro Ala Leu Thr Ala Leu Leu Cys Leu Gly Leu Ser
        1               5                   10 ctg ggc ccc agg acc cgc gtg cag gca ggg c cc ttc ccc aaa ccc acc     156
Leu Gly Pro Arg Thr Arg Val Gln Ala Gly P ro Phe Pro Lys Pro Thr
 15              20                  25                  30 ctc tgg gct gag cca ggc tct gtg atc agc t gg ggg agc ccc gtg acc    204
Leu Trp Ala Glu Pro Gly Ser Val Ile Ser T rp Gly Ser Pro Val Thr
                35                  40                  45 atc tgg tgt cag ggg agc ctg gag gcc cag g ag tac caa ctg gat aaa    252
Ile Trp Cys Gln Gly Ser Leu Glu Ala Gln G lu Tyr Gln Leu Asp Lys
            50                  55                  60 gag gga agc cca gag ccc ttg gac aga aat a ac cca ctg gaa ccc aag    300
Glu Gly Ser Pro Glu Pro Leu Asp Arg Asn A sn Pro Leu Glu Pro Lys
        65                  70                  75 aac aag gcc aga ttc tcc atc cca tcc atg a ca cag cac cat gca ggg    348
Asn Lys Ala Arg Phe Ser Ile Pro Ser Met T hr Gln His His Ala Gly
80                  85                  90 aga tac cgc tgc cac tat tac agc tct gca g gc tgg tca gag ccc agc    396
Arg Tyr Arg Cys His Tyr Tyr Ser Ser Ala G ly Trp Ser Glu Pro Ser
95                  100                 105                 110 gac ccc ctg gag ctg gtg atg aca gga gcc t at agc aaa ccc acc ctc    444
Asp Pro Leu Glu Leu Val Met Thr Gly Ala T yr Ser Lys Pro Thr Leu
                115                 120                 125 tca gcc ctg ccc agc cct gtg gtg gcc tca g gg ggg aat atg acc ctc    492
Ser Ala Leu Pro Ser Pro Val Val Ala Ser G ly Gly Asn Met Thr Leu
                130                 135                 140 cga tgt ggc tca cag aag aga tat cac cat t tt gtt ctg atg aag gaa    540
Arg Cys Gly Ser Gln Lys Arg Tyr His His P he Val Leu Met Lys Glu
            145                 150                 155 gga gaa cac cag ctc ccc cgg acc ctg gac t ca cag cag ctc cac agt    588
Gly Glu His Gln Leu Pro Arg Thr Leu Asp S er Gln Gln Leu His Ser
        160                 165                 170 ggg ggg ttc cag gcc ctg ttc cct gtg ggc c cc gtg aac ccc agc cac    636
Gly Gly Phe Gln Ala Leu Phe Pro Val Gly P ro Val Asn Pro Ser His
175                 180                 185                 190
```

-continued

```
agg tgg agg ttc aca tgc tat tac tat tat a tg aac acc ccc cgg gtg         684
Arg Trp Arg Phe Thr Cys Tyr Tyr Tyr Tyr M et Asn Thr Pro Arg Val
                195                 200                 205 tgg tcc cac ccc agt gac ccc ctg gag att c tg ccc tca ggc gtg tct         732
Trp Ser His Pro Ser Asp Pro Leu Glu Ile L eu Pro Ser Gly Val Ser
                210                 215                 220 agg aag ccc tcc ctc ctg acc ctg cag ggc c ct gtc ctg gcc cct ggg         780
Arg Lys Pro Ser Leu Leu Thr Leu Gln Gly P ro Val Leu Ala Pro Gly
                225                 230                 235 cag agt ctg acc ctc cag tgt ggc tct gat g tc ggc tac gac aga ttt         828
Gln Ser Leu Thr Leu Gln Cys Gly Ser Asp V al Gly Tyr Asp Arg Phe
                240                 245                 250 gtt ctg tat aag gag ggg gaa cgt gac ttc c tc cag cgc cct ggc cag         876
Val Leu Tyr Lys Glu Gly Glu Arg Asp Phe L eu Gln Arg Pro Gly Gln
255                 260                 265                 270 cag ccc cag gct ggg ctc tcc cag gcc aac t tc acc ctg ggc cct gtg         924
Gln Pro Gln Ala Gly Leu Ser Gln Ala Asn P he Thr Leu Gly Pro Val
                275                 280                 285 agc ccc tcc aat ggg ggc cag tac agg tgc t ac ggt gca cac aac ctc         972
Ser Pro Ser Asn Gly Gly Gln Tyr Arg Cys T yr Gly Ala His Asn Leu
                290                 295                 300 tcc tcc gag tgg tcg gcc ccc agc gac ccc c tg aac atc ctg atg gca        1020
Ser Ser Glu Trp Ser Ala Pro Ser Asp Pro L eu Asn Ile Leu Met Ala
                305                 310                 315 gga cag atc tat gac acc gtc tcc ctg tca g ca cag ccg ggc ccc aca        1068
Gly Gln Ile Tyr Asp Thr Val Ser Leu Ser A la Gln Pro Gly Pro Thr
320                 325                 330 gtg gcc tca gga gag aac gtg acc ctg ctg t gt cag tca tgg tgg cag        1116
Val Ala Ser Gly Glu Asn Val Thr Leu Leu C ys Gln Ser Trp Trp Gln
335                 340                 345                 350 ttt gac act ttc ctt ctg acc aaa gaa ggg g ca gcc cat ccc cca ctg        1164
Phe Asp Thr Phe Leu Leu Thr Lys Glu Gly A la Ala His Pro Pro Leu
                355                 360                 365 cgt ctg aga tca atg tac gga gct cat aag t ac cag gct gaa ttc ccc        1212
Arg Leu Arg Ser Met Tyr Gly Ala His Lys T yr Gln Ala Glu Phe Pro
                370                 375                 380 atg agt cct gtg acc tca gcc cac gcg ggg a cc tac agg tgc tac ggc        1260
Met Ser Pro Val Thr Ser Ala His Ala Gly T hr Tyr Arg Cys Tyr Gly
                385                 390                 395 tca cgc agc tcc aac ccc tac ctg ctg tct c ac ccc agt gag ccc ctg        1308
Ser Arg Ser Ser Asn Pro Tyr Leu Leu Ser H is Pro Ser Glu Pro Leu
                400                 405                 410 gag ctc gtg gtc tca gga cac tct gga ggc t cc agc ctc cca ccc aca        1356
Glu Leu Val Val Ser Gly His Ser Gly Gly S er Ser Leu Pro Pro Thr
415                 420                 425                 430 ggg ccg ccc tcc aca cct ggt ctg gga aga t ac ctg gag gtt ttg att        1404
Gly Pro Pro Ser Thr Pro Gly Leu Gly Arg T yr Leu Glu Val Leu Ile
                435                 440                 445 ggg gtc tcg gtg gcc ttc gtc ctg ctg ctc t tc ctc ctc ctc ttc ctc        1452
Gly Val Ser Val Ala Phe Val Leu Leu Leu P he Leu Leu Leu Phe Leu
                450                 455                 460 ctc ctc cga cgt cag cgt cac agc aaa cac a gg aca tct gac cag aga        1500
Leu Leu Arg Arg Gln Arg His Ser Lys His A rg Thr Ser Asp Gln Arg
                465                 470                 475 aag act gat ttc cag cgt cct gca ggg gct g cg gag aca gag ccc aag        1548
Lys Thr Asp Phe Gln Arg Pro Ala Gly Ala A la Glu Thr Glu Pro Lys
                480                 485                 490 gac agg ggc ctg ctg agg agg tcc agc cca g ct gct gac gtc cag gaa        1596
Asp Arg Gly Leu Leu Arg Arg Ser Ser Pro A la Ala Asp Val Gln Glu
495                 500                 505                 510
```

-continued

```
gaa aac ctc tat gct gcc gtg aag gac aca c ag tct gag gac ggg gtg     1644
Glu Asn Leu Tyr Ala Ala Val Lys Asp Thr G ln Ser Glu Asp Gly Val
                515                 520                 525 gag ctg gac agt cag agc cca cac gat gaa g ac ccc cac gca gtg acg     1692
Glu Leu Asp Ser Gln Ser Pro His Asp Glu A sp Pro His Ala Val Thr
            530                 535                 540 tat gcc ccg gtg aaa cac tcc agt cct agg a ga gaa atg gcc tct cct     1740
Tyr Ala Pro Val Lys His Ser Ser Pro Arg A rg Glu Met Ala Ser Pro
        545                 550                 555 cct tcc cca ctg tct ggg gaa ttc ctg gac a ca aag gac aga cag gca     1788
Pro Ser Pro Leu Ser Gly Glu Phe Leu Asp T hr Lys Asp Arg Gln Ala
    560                 565                 570 gaa gag gac aga cag atg gac act gag gct g ct gca tct gaa gcc tcc     1836
Glu Glu Asp Arg Gln Met Asp Thr Glu Ala A la Ala Ser Glu Ala Ser
575                 580                 585                 590 cag gat gtg acc tac gcc cag ctg cac agc t tg acc ctt aga cgg aag     1884
Gln Asp Val Thr Tyr Ala Gln Leu His Ser L eu Thr Leu Arg Arg Lys
                595                 600                 605 gca act gag cct cct cca tcc cag gaa ggg g aa cct cca gct gag ccc     1932
Ala Thr Glu Pro Pro Pro Ser Gln Glu Gly G lu Pro Pro Ala Glu Pro
            610                 615                 620 agc atc tac gcc act ctg gcc atc cac tag c ccgggggt acgcagaccc       1982
Ser Ile Tyr Ala Thr Leu Ala Ile His
        625                 630 cacactcagc agaaggagac tcaggactgc tgaaggacgg gagctgcccc c agtggacac   2042 cagtgaaccc cagtcagcct ggacccctaa cacagaccat gaggagacgc t gggaacttg   2102 tgggactcac ctgactcaaa gatgactaat atcgtcccat tttggaaata a agcaacaga   2162 cttctcaagc aggtcgtctc gttccaagat ct                                  2194
```

<210> SEQ ID NO 20
<211> LENGTH: 631
<212> TYPE: PRT
<213> ORGANISM: human

<400> SEQUENCE: 20

```
Met Thr Pro Ala Leu Thr Ala Leu Leu Cys L eu Gly Leu Ser Leu Gly
  1               5                  10                  15

Pro Arg Thr Arg Val Gln Ala Gly Pro Phe P ro Lys Pro Thr Leu Trp
                 20                  25                  30

Ala Glu Pro Gly Ser Val Ile Ser Trp Gly S er Pro Val Thr Ile Trp
             35                  40                  45

Cys Gln Gly Ser Leu Glu Ala Gln Glu Tyr G ln Leu Asp Lys Glu Gly
         50                  55                  60

Ser Pro Glu Pro Leu Asp Arg Asn Asn Pro L eu Glu Pro Lys Asn Lys
 65                  70                  75                  80

Ala Arg Phe Ser Ile Pro Ser Met Thr Gln H is His Ala Gly Arg Tyr
                 85                  90                  95

Arg Cys His Tyr Tyr Ser Ser Ala Gly Trp S er Glu Pro Ser Asp Pro
            100                 105                 110

Leu Glu Leu Val Met Thr Gly Ala Tyr Ser L ys Pro Thr Leu Ser Ala
        115                 120                 125

Leu Pro Ser Pro Val Val Ala Ser Gly Gly A sn Met Thr Leu Arg Cys
    130                 135                 140

Gly Ser Gln Lys Arg Tyr His His Phe Val L eu Met Lys Glu Gly Glu
145                 150                 155                 160
```

```
His Gln Leu Pro Arg Thr Leu Asp Ser Gln Gln Leu His Ser Gly Gly
                165                 170                 175

Phe Gln Ala Leu Phe Pro Val Gly Pro Val Asn Pro Ser His Arg Trp
            180                 185                 190

Arg Phe Thr Cys Tyr Tyr Tyr Met Asn Thr Pro Arg Val Trp Ser
            195                 200                 205

His Pro Ser Asp Pro Leu Glu Ile Leu Pro Ser Gly Val Ser Arg Lys
            210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
                260                 265                 270

Gln Ala Gly Leu Ser Gln Ala Asn Phe Thr Leu Gly Pro Val Ser Pro
            275                 280                 285

Ser Asn Gly Gly Gln Tyr Arg Cys Tyr Gly Ala His Asn Leu Ser Ser
            290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
            355                 360                 365

Arg Ser Met Tyr Gly Ala His Lys Tyr Gln Ala Glu Phe Pro Met Ser
            370                 375                 380

Pro Val Thr Ser Ala His Ala Gly Thr Tyr Arg Cys Tyr Gly Ser Arg
385                 390                 395                 400

Ser Ser Asn Pro Tyr Leu Leu Ser His Pro Ser Glu Pro Leu Glu Leu
                405                 410                 415

Val Val Ser Gly His Ser Gly Gly Ser Ser Leu Pro Pro Thr Gly Pro
                420                 425                 430

Pro Ser Thr Pro Gly Leu Gly Arg Tyr Leu Glu Val Leu Ile Gly Val
            435                 440                 445

Ser Val Ala Phe Val Leu Leu Leu Phe Leu Leu Leu Phe Leu Leu Leu
450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
            485                 490                 495

Gly Leu Leu Arg Arg Ser Ser Pro Ala Ala Asp Val Gln Glu Glu Asn
            500                 505                 510

Leu Tyr Ala Ala Val Lys Asp Thr Gln Ser Glu Asp Gly Val Glu Leu
            515                 520                 525

Asp Ser Gln Ser Pro His Asp Glu Asp Pro His Ala Val Thr Tyr Ala
            530                 535                 540

Pro Val Lys His Ser Ser Pro Arg Arg Glu Met Ala Ser Pro Pro Ser
545                 550                 555                 560

Pro Leu Ser Gly Glu Phe Leu Asp Thr Lys Asp Arg Gln Ala Glu Glu
                565                 570                 575
```

```
                                         -continued

Asp Arg Gln Met Asp Thr Glu Ala Ala S er Glu Ala Ser Gln Asp
            580                 585                 590

Val Thr Tyr Ala Gln Leu His Ser Leu Thr L eu Arg Arg Lys Ala Thr
            595                 600                 605

Glu Pro Pro Ser Gln Glu Gly Glu Pro P ro Ala Glu Pro Ser Ile
        610                 615                 620

Tyr Ala Thr Leu Ala Ile His
625                 630

<210> SEQ ID NO 21
<211> LENGTH: 2061
<212> TYPE: DNA
<213> ORGANISM: human
<220> FEATURE:
<221> NAME/KEY: CDS
<222> LOCATION: (67)..(1839)

<400> SEQUENCE: 21
tttgtgtcct gccaggcacc gtggtctcat ccgcctgcac agctgagtcc a gtgggagct            60 gacgcc atg acc ctc acc ctc tca gtc ctg att tgc ctc ggg ctg agt           108
       Met Thr Leu Thr Leu Ser V al Leu Ile Cys Leu Gly Leu Ser
           1               5                   10 gtg ggc ccc agg acc tgc gtg cag gca ggc a cc ctc ccc aaa ccc acc         156
Val Gly Pro Arg Thr Cys Val Gln Ala Gly T hr Leu Pro Lys Pro Thr
 15              20                  25                  30 ctc tgg gct gag cca gcc tct gtg ata gct c gg ggg aag ccc gtg acc         204
Leu Trp Ala Glu Pro Ala Ser Val Ile Ala A rg Gly Lys Pro Val Thr
                 35                  40                  45 ctc tgg tgt cag ggg ccc ctg gag act gag g ag tac cgt ctg gat aag         252
Leu Trp Cys Gln Gly Pro Leu Glu Thr Glu G lu Tyr Arg Leu Asp Lys
             50                  55                  60 gag gga ctc cca tgg gcc cgg aag aga cag a ac cca ctg gag cct gga         300
Glu Gly Leu Pro Trp Ala Arg Lys Arg Gln A sn Pro Leu Glu Pro Gly
         65                  70                  75 gcc aag gcc aag ttc cac att cca tcc acg g tg tat gac agt gca ggg         348
Ala Lys Ala Lys Phe His Ile Pro Ser Thr V al Tyr Asp Ser Ala Gly
     80                  85                  90 cga tac cgc tgc tac tat gag acc cct gca g gc tgg tca gag ccc agt         396
Arg Tyr Arg Cys Tyr Tyr Glu Thr Pro Ala G ly Trp Ser Glu Pro Ser
 95                 100                 105                 110 gac ccc ctg gag ctg gtg gcg aca gga ttc t at gca gaa ccc act ctt         444
Asp Pro Leu Glu Leu Val Ala Thr Gly Phe T yr Ala Glu Pro Thr Leu
                115                 120                 125 tta gcc ctg ccg agt cct gtg gtg gcc tca g ga gga aat gtg acc ctc         492
Leu Ala Leu Pro Ser Pro Val Val Ala Ser G ly Gly Asn Val Thr Leu
            130                 135                 140 cag tgt gat aca ctg gac gga ctt ctc acg t tt gtt ctt gtt gag gaa         540
Gln Cys Asp Thr Leu Asp Gly Leu Leu Thr P he Val Leu Val Glu Glu
        145                 150                 155 gaa cag aag ctc ccc agg acc ctg tac tca c ag aag ctc ccc aaa ggg         588
Glu Gln Lys Leu Pro Arg Thr Leu Tyr Ser G ln Lys Leu Pro Lys Gly
    160                 165                 170 cca tcc cag gcc ctg ttc cct gtg ggt ccc g tg acc ccc agc tgc agg         636
Pro Ser Gln Ala Leu Phe Pro Val Gly Pro V al Thr Pro Ser Cys Arg
175                 180                 185                 190 tgg agg ttc aga tgc tat tac tat tac agg a aa aac cct cag gtg tgg         684
Trp Arg Phe Arg Cys Tyr Tyr Tyr Tyr Arg L ys Asn Pro Gln Val Trp
                195                 200                 205
```

| | | |
|---|---|---|
| tcg aac ccc agt gac ctc ctg gag att ctg g tc cca ggc gtg tct agg | 732 | |
| Ser Asn Pro Ser Asp Leu Leu Glu Ile Leu V al Pro Gly Val Ser Arg | | |
| 210 215 220 | | |
| aag ccc tcc ctc ctg atc ccg cag ggc tct g tc gtg gcc cgc gga ggc | 780 | |
| Lys Pro Ser Leu Leu Ile Pro Gln Gly Ser V al Val Ala Arg Gly Gly | | |
| 225 230 235 | | |
| agc ctg acc ctg cag tgt cgc tct gat gtc g gc tat gac ata ttc gtt | 828 | |
| Ser Leu Thr Leu Gln Cys Arg Ser Asp Val G ly Tyr Asp Ile Phe Val | | |
| 240 245 250 | | |
| ctg tac aag gag ggg gaa cat gac ctc gtc c ag ggc tct ggc cag cag | 876 | |
| Leu Tyr Lys Glu Gly Glu His Asp Leu Val G ln Gly Ser Gly Gln Gln | | |
| 255 260 265 270 | | |
| ccc cag gct ggg ctc tcc cag gcc aac ttc a cc ctg ggc cct gtg agc | 924 | |
| Pro Gln Ala Gly Leu Ser Gln Ala Asn Phe T hr Leu Gly Pro Val Ser | | |
| 275 280 285 | | |
| cgc tcc cac ggg ggc cag tac aga tgc tac g gt gca cac aac ctc tcc | 972 | |
| Arg Ser His Gly Gly Gln Tyr Arg Cys Tyr G ly Ala His Asn Leu Ser | | |
| 290 295 300 | | |
| cct agg tgg tcg gcc ccc agc gac ccc ctg g ac atc ctg atc gca gga | 1020 | |
| Pro Arg Trp Ser Ala Pro Ser Asp Pro Leu A sp Ile Leu Ile Ala Gly | | |
| 305 310 315 | | |
| ctg atc cct gac ata ccc gcc ctc tcg gtg c ag ccg ggc ccc aag gtg | 1068 | |
| Leu Ile Pro Asp Ile Pro Ala Leu Ser Val G ln Pro Gly Pro Lys Val | | |
| 320 325 330 | | |
| gcc tca gga gag aac gtg acc ctg ctg tgt c ag tca tgg cat cag ata | 1116 | |
| Ala Ser Gly Glu Asn Val Thr Leu Leu Cys G ln Ser Trp His Gln Ile | | |
| 335 340 345 350 | | |
| gac act ttc ttt ttg acc aag gag ggg gca g cc cat ccc ccg ctg tgt | 1164 | |
| Asp Thr Phe Phe Leu Thr Lys Glu Gly Ala A la His Pro Pro Leu Cys | | |
| 355 360 365 | | |
| cta aag tca aag tac cag tct tat aga cac c ag gct gaa ttc tcc atg | 1212 | |
| Leu Lys Ser Lys Tyr Gln Ser Tyr Arg His G ln Ala Glu Phe Ser Met | | |
| 370 375 380 | | |
| agt cct gtg acc tca gcc cag ggt gga acc t ac cga tgc tac agc gca | 1260 | |
| Ser Pro Val Thr Ser Ala Gln Gly Gly Thr T yr Arg Cys Tyr Ser Ala | | |
| 385 390 395 | | |
| atc agg tcc tac ccc tac ctg ctg tcc agc c ct agt tac ccc cag gag | 1308 | |
| Ile Arg Ser Tyr Pro Tyr Leu Leu Ser Ser P ro Ser Tyr Pro Gln Glu | | |
| 400 405 410 | | |
| ctc gtg gtc tca gga ccc tct ggg gat ccc a gc ctc tca cct aca ggc | 1356 | |
| Leu Val Val Ser Gly Pro Ser Gly Asp Pro S er Leu Ser Pro Thr Gly | | |
| 415 420 425 430 | | |
| tcc acc ccc aca cct ggc cct gag gac cag c cc ctc acc ccc acg ggg | 1404 | |
| Ser Thr Pro Thr Pro Gly Pro Glu Asp Gln P ro Leu Thr Pro Thr Gly | | |
| 435 440 445 | | |
| ttg gat ccc cag agt ggt ctg gga agg cac c tg ggg gtt gtg act ggg | 1452 | |
| Leu Asp Pro Gln Ser Gly Leu Gly Arg His L eu Gly Val Val Thr Gly | | |
| 450 455 460 | | |
| gtc tca gtg gcc ttc gtc ctg ctg ttc c tc ctc ctc ttc ctc ctc | 1500 | |
| Val Ser Val Ala Phe Val Leu Leu Phe L eu Leu Leu Phe Leu Leu | | |
| 465 470 475 | | |
| ctc cga cat cgg cat cag agc aaa cac agg a ca tcg gcc cat ttc tac | 1548 | |
| Leu Arg His Arg His Gln Ser Lys His Arg T hr Ser Ala His Phe Tyr | | |
| 480 485 490 | | |
| cgt cct gca ggg gct gcg ggg cca gag ccc a ag gac cag ggc ctg cag | 1596 | |
| Arg Pro Ala Gly Ala Ala Gly Pro Glu Pro L ys Asp Gln Gly Leu Gln | | |
| 495 500 505 510 | | |
| aag agg gcc agc cca gtt gct gac atc cag g ag gaa att ctc aat gct | 1644 | |
| Lys Arg Ala Ser Pro Val Ala Asp Ile Gln G lu Glu Ile Leu Asn Ala | | |
| 515 520 525 | | |

-continued

```
gcc gtg aag gac aca cag ccc aag gac ggg g tg gag atg gat gct cgg      1692
Ala Val Lys Asp Thr Gln Pro Lys Asp Gly V al Glu Met Asp Ala Arg
            530                 535                 540 gct gct gca tct gaa gcc ccc cag gat gtg a cc tac gcc cag ctg cac      1740
Ala Ala Ala Ser Glu Ala Pro Gln Asp Val T hr Tyr Ala Gln Leu His
        545                 550                 555 agc ttg acc ctc aga cgg gag gca act gag c ct cct cca tcc cag gaa      1788
Ser Leu Thr Leu Arg Arg Glu Ala Thr Glu P ro Pro Pro Ser Gln Glu
560                 565                 570 agg gaa cct cca gct gaa ccc agc atc tac g cc ccc ctg gcc atc cac      1836
Arg Glu Pro Pro Ala Glu Pro Ser Ile Tyr A la Pro Leu Ala Ile His
575                 580                 585                 590 tag ccacgggg acccagatct catactcaac agaaggagac tcagagac tc             1889 cagaaggcac aggagctgcc cccagtggac accaatgaac cccagccagc c tggacccct    1949 aacaaagacc accaggacat cctgggaact ctgggactca ctagattctg c agtcaaaga    2009 tgactaatat ccttgcattt ttgaaatgaa gccacagact tctcaataaa t c            2061
```

<210> SEQ ID NO 22
<211> LENGTH: 590
<212> TYPE: PRT
<213> ORGANISM: human

<400> SEQUENCE: 22

```
Met Thr Leu Thr Leu Ser Val Leu Ile Cys L eu Gly Leu Ser Val Gly
 1               5                  10                  15

Pro Arg Thr Cys Val Gln Ala Gly Thr Leu P ro Lys Pro Thr Leu Trp
                20                  25                  30

Ala Glu Pro Ala Ser Val Ile Ala Arg Gly L ys Pro Val Thr Leu Trp
            35                  40                  45

Cys Gln Gly Pro Leu Glu Thr Glu Glu Tyr A rg Leu Asp Lys Glu Gly
        50                  55                  60

Leu Pro Trp Ala Arg Lys Arg Gln Asn Pro L eu Glu Pro Gly Ala Lys
 65                  70                  75                  80

Ala Lys Phe His Ile Pro Ser Thr Val Tyr A sp Ser Ala Gly Arg Tyr
                85                  90                  95

Arg Cys Tyr Tyr Glu Thr Pro Ala Gly Trp S er Glu Pro Ser Asp Pro
            100                 105                 110

Leu Glu Leu Val Ala Thr Gly Phe Tyr Ala G lu Pro Thr Leu Leu Ala
        115                 120                 125

Leu Pro Ser Pro Val Val Ala Ser Gly Gly A sn Val Thr Leu Gln Cys
    130                 135                 140

Asp Thr Leu Asp Gly Leu Leu Thr Phe Val L eu Val Glu Glu Gln
145                 150                 155                 160

Lys Leu Pro Arg Thr Leu Tyr Ser Gln Lys L eu Pro Lys Gly Pro Ser
                165                 170                 175

Gln Ala Leu Phe Pro Val Gly Pro Val Thr P ro Ser Cys Arg Trp Arg
            180                 185                 190

Phe Arg Cys Tyr Tyr Tyr Arg Lys Asn P ro Gln Val Trp Ser Asn
        195                 200                 205

Pro Ser Asp Leu Leu Glu Ile Leu Val Pro G ly Val Ser Arg Lys Pro
    210                 215                 220

Ser Leu Leu Ile Pro Gln Gly Ser Val Ala Arg Gly Gly Ser Leu
225                 230                 235                 240

Thr Leu Gln Cys Arg Ser Asp Val Gly Tyr A sp Ile Phe Val Leu Tyr
                245                 250                 255
```

| | | | | | | | | | | | |
|---|---|---|---|---|---|---|---|---|---|---|---|
|Lys|Glu|Gly|Glu|His|Asp|Leu|Val|Gln|Gly|Ser|Gly|Gln|Gln|Pro|Gln|
| | | |260| | | |265| | | |270| | | | |

Ala Gly Leu Ser Gln Ala Asn Phe Thr Leu Gly Pro Val Ser Arg Ser
            275                 280                 285

His Gly Gly Gln Tyr Arg Cys Tyr Gly Ala His Asn Leu Ser Pro Arg
        290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                325                 330                 335

Gly Glu Asn Val Thr Leu Leu Cys Gln Ser Trp His Gln Ile Asp Thr
            340                 345                 350

Phe Phe Leu Thr Lys Glu Gly Ala Ala His Pro Pro Leu Cys Leu Lys
        355                 360                 365

Ser Lys Tyr Gln Ser Tyr Arg His Gln Ala Glu Phe Ser Met Ser Pro
    370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                405                 410                 415

Val Ser Gly Pro Ser Gly Asp Pro Ser Leu Ser Pro Thr Gly Ser Thr
            420                 425                 430

Pro Thr Pro Gly Pro Glu Asp Gln Pro Leu Thr Pro Thr Gly Leu Asp
        435                 440                 445

Pro Gln Ser Gly Leu Gly Arg His Leu Gly Val Val Thr Gly Val Ser
    450                 455                 460

Val Ala Phe Val Leu Leu Leu Phe Leu Leu Leu Phe Leu Leu Leu Arg
465                 470                 475                 480

His Arg His Gln Ser Lys His Arg Thr Ser Ala His Phe Tyr Arg Pro
                485                 490                 495

Ala Gly Ala Ala Gly Pro Glu Pro Lys Asp Gln Gly Leu Gln Lys Arg
            500                 505                 510

Ala Ser Pro Val Ala Asp Ile Gln Glu Glu Ile Leu Asn Ala Ala Val
        515                 520                 525

Lys Asp Thr Gln Pro Lys Asp Gly Val Glu Met Asp Ala Arg Ala Ala
    530                 535                 540

Ala Ser Glu Ala Pro Gln Asp Val Thr Tyr Ala Gln Leu His Ser Leu
545                 550                 555                 560

Thr Leu Arg Arg Glu Ala Thr Glu Pro Pro Pro Ser Gln Glu Arg Glu
                565                 570                 575

Pro Pro Ala Glu Pro Ser Ile Tyr Ala Pro Leu Ala Ile His
            580                 585                 590

<210> SEQ ID NO 23
<211> LENGTH: 28
<212> TYPE: DNA
<213> ORGANISM: human

<400> SEQUENCE: 23
tatgcggccg ccatgatgac aatgtggt                                      28

<210> SEQ ID NO 24
<211> LENGTH: 25
<212> TYPE: DNA
<213> ORGANISM: human

-continued

<400> SEQUENCE: 24
tatgcggccg ccccttgcga tagcg                                      25

<210> SEQ ID NO 25
<211> LENGTH: 31
<212> TYPE: DNA
<213> ORGANISM: human

<400> SEQUENCE: 25
atagtcgaca acgccatcat gagatgtggt g                               31

<210> SEQ ID NO 26
<211> LENGTH: 29
<212> TYPE: DNA
<213> ORGANISM: human

<400> SEQUENCE: 26
taaagatctg ggctcgttag ctgtcgggt                                  29

<210> SEQ ID NO 27
<211> LENGTH: 33
<212> TYPE: DNA
<213> ORGANISM: human

<400> SEQUENCE: 27
tatagatcta cccccaggtg ccttcccaga cca                             33

<210> SEQ ID NO 28
<211> LENGTH: 42
<212> TYPE: PRT
<213> ORGANISM: human
<220> FEATURE:
<221> NAME/KEY: VARIANT
<222> LOCATION: (2)
<223> OTHER INFORMATION: Xaa is Gly or Arg
<220> FEATURE:
<221> NAME/KEY: VARIANT
<222> LOCATION: (5)
<223> OTHER INFORMATION: Xaa is Leu or Val
<220> FEATURE:
<221> NAME/KEY: VARIANT
<222> LOCATION: (6)
<223> OTHER INFORMATION: Xaa is Gly or Asp
<220> FEATURE:
<221> NAME/KEY: VARIANT
<222> LOCATION: (10)
<223> OTHER INFORMATION: Xaa is His, Arg or Cys
<220> FEATURE:
<221> NAME/KEY: VARIANT
<222> LOCATION: (11)
<223> OTHER INFORMATION: Xaa is Val or Met
<220> FEATURE:
<221> NAME/KEY: VARIANT
<222> LOCATION: (13)
<223> OTHER INFORMATION: Xaa is Ala or Thr
<220> FEATURE:
<221> NAME/KEY: VARIANT
<222> LOCATION: (15)
<223> OTHER INFORMATION: Xaa is His, Pro or Thr
<220> FEATURE:
<221> NAME/KEY: VARIANT
<222> LOCATION: (16)
<223> OTHER INFORMATION: Xaa is Leu, Ile or Phe
<220> FEATURE:
<221> NAME/KEY: VARIANT
<222> LOCATION: (18)
<223> OTHER INFORMATION: Xaa is Gly, Asp or Ala
<220> FEATURE:
<221> NAME/KEY: VARIANT
<222> LOCATION: (26)
<223> OTHER INFORMATION: Xaa is Thr, Ile, Se r or Ala

```
<220> FEATURE:
<221> NAME/KEY: VARIANT
<222> LOCATION: (30)
<223> OTHER INFORMATION: Xaa is Thr, Ile, Ser or Ala
<220> FEATURE:
<221> NAME/KEY: VARIANT
<222> LOCATION: (31)
<223> OTHER INFORMATION: Xaa is a sequence of 70 amino acids
<220> FEATURE:
<221> NAME/KEY: VARIANT
<222> LOCATION: (37)
<223> OTHER INFORMATION: Xaa is Gly or Val
<220> FEATURE:
<221> NAME/KEY: VARIANT
<222> LOCATION: (40)
<223> OTHER INFORMATION: Xaa is Met or Ala

<400> SEQUENCE: 28

Leu Xaa Leu Ser Xaa Xaa Pro Arg Thr Xaa Xaa Gln Xaa Gly Xaa Xaa
 1               5                  10                  15

Pro Xaa Pro Thr Leu Trp Ala Glu Pro Xaa Ser Phe Ile Xaa Xaa Ser
             20                  25                  30

Asp Pro Lys Leu Xaa Leu Val Xaa Thr Gly
         35                  40

<210> SEQ ID NO 29
<211> LENGTH: 1016
<212> TYPE: DNA
<213> ORGANISM: human
<220> FEATURE:
<221> NAME/KEY: CDS
<222> LOCATION: (69)..(968)

<400> SEQUENCE: 29
ctgagtctgc ctgtggcatg gacctgcatc ttccctgaag catctccagg g ctgaaaaat    60 cactgacc atg gca cca tgg tct cat cca tct gca  cag ctg cag cca gtg   110
         Met Ala Pro Trp Ser His Pro Ser Ala Gln Leu Gln Pro Val
          1               5                  10 gga gga gac gcc gtg agc cct gcc ctc atg g tt ctg ctc tgc ctc ggg    158
Gly Gly Asp Ala Val Ser Pro Ala Leu Met Val Leu Leu Cys Leu Gly
 15                  20                  25                  30 ctg agt ctg ggc ccc agg acc cac gtg cag g ca ggg aac ctc tcc aaa    206
Leu Ser Leu Gly Pro Arg Thr His Val Gln Ala Gly Asn Leu Ser Lys
                 35                  40                  45 gcc acc ctc tgg gct gag cca ggc tct gtg a tc agc cgg ggg aac tct    254
Ala Thr Leu Trp Ala Glu Pro Gly Ser Val Ile Ser Arg Gly Asn Ser
             50                  55                  60 gtg acc atc cgg tgt cag ggg acc ctg gag g cc cag gaa tac cgt ctg    302
Val Thr Ile Arg Cys Gln Gly Thr Leu Glu Ala Gln Glu Tyr Arg Leu
         65                  70                  75 gtt aaa gag gga agc cca gaa ccc tgg gac a ca cag aac cca ctg gag    350
Val Lys Glu Gly Ser Pro Glu Pro Trp Asp Thr Gln Asn Pro Leu Glu
     80                  85                  90 ccc aag aac aag gcc aga ttc tcc atc cca t cc atg aca gag cac cat    398
Pro Lys Asn Lys Ala Arg Phe Ser Ile Pro Ser Met Thr Glu His His
 95                 100                 105                 110 gca ggg aga tac cgc tgt tac tac tac agc c ct gca ggc tgg tca gag    446
Ala Gly Arg Tyr Arg Cys Tyr Tyr Tyr Ser Pro Ala Gly Trp Ser Glu
                115                 120                 125 ccc agc gac ccc ctg gag ctg gtg gtg aca g ga ttc tac aac aaa ccc    494
Pro Ser Asp Pro Leu Glu Leu Val Val Thr Gly Phe Tyr Asn Lys Pro
            130                 135                 140
```

```
acc ctc tca gcc ctg ccc agt cct gtg gtg a cc tca gga gag aac gtg        542
Thr Leu Ser Ala Leu Pro Ser Pro Val Val T hr Ser Gly Glu Asn Val
            145                 150                 155 acc ctc cag tgt ggc tca cgg ctg aga ttc g ac agg ttc att ctg act        590
Thr Leu Gln Cys Gly Ser Arg Leu Arg Phe A sp Arg Phe Ile Leu Thr
160                 165                 170 gag gaa gga gac cac aag ctc tcc tgg acc t tg gac tca cag ctg acc        638
Glu Glu Gly Asp His Lys Leu Ser Trp Thr L eu Asp Ser Gln Leu Thr
175                 180                 185                 190 ccc agt ggg cag ttc cag gcc ctg ttc cct g tg ggc cct gtg acc ccc        686
Pro Ser Gly Gln Phe Gln Ala Leu Phe Pro V al Gly Pro Val Thr Pro
                195                 200                 205 agc cac agg tgg atg ctc aga tgc tat ggc t ct cgc agg cat atc ctg        734
Ser His Arg Trp Met Leu Arg Cys Tyr Gly S er Arg Arg His Ile Leu
            210                 215                 220 cag gta tgg tca gaa ccc agt gac ctc ctg g ag att ccg gtc tca gga        782
Gln Val Trp Ser Glu Pro Ser Asp Leu Leu G lu Ile Pro Val Ser Gly
            225                 230                 235 gca gct gat aac ctc agt ccg tca caa aac a ag tct gac tct ggg act        830
Ala Ala Asp Asn Leu Ser Pro Ser Gln Asn L ys Ser Asp Ser Gly Thr
240                 245                 250 gcc tca cac ctt cag gat tac gca gta gag a at ctc atc cgc atg ggc        878
Ala Ser His Leu Gln Asp Tyr Ala Val Glu A sn Leu Ile Arg Met Gly
255                 260                 265                 270 atg gcc ggc ttg atc ctg gtg gtc ctt ggg a tt ctg ata ttt cag gat        926
Met Ala Gly Leu Ile Leu Val Val Leu Gly I le Leu Ile Phe Gln Asp
                275                 280                 285 tgg cac agc cag aga agc ccc caa gct gca g ct gga agg tga                968
Trp His Ser Gln Arg Ser Pro Gln Ala Ala A la Gly Arg
            290                 295                 300 acagaagaga gaacaatgca ccattgaatg ctggagcctt ggaagcga                   1016

<210> SEQ ID NO 30
<211> LENGTH: 299
<212> TYPE: PRT
<213> ORGANISM: human

<400> SEQUENCE: 30

Met Ala Pro Trp Ser His Pro Ser Ala Gln L eu Gln Pro Val Gly Gly
  1               5                  10                  15

Asp Ala Val Ser Pro Ala Leu Met Val Leu L eu Cys Leu Gly Leu Ser
                 20                  25                  30

Leu Gly Pro Arg Thr His Val Gln Ala Gly A sn Leu Ser Lys Ala Thr
             35                  40                  45

Leu Trp Ala Glu Pro Gly Ser Val Ile Ser A rg Gly Asn Ser Val Thr
 50                  55                  60

Ile Arg Cys Gln Gly Thr Leu Glu Ala Gln G lu Tyr Arg Leu Val Lys
 65                  70                  75                  80

Glu Gly Ser Pro Glu Pro Trp Asp Thr Gln A sn Pro Leu Glu Pro Lys
                 85                  90                  95

Asn Lys Ala Arg Phe Ser Ile Pro Ser Met T hr Glu His His Ala Gly
            100                 105                 110

Arg Tyr Arg Cys Tyr Tyr Tyr Ser Pro Ala G ly Trp Ser Glu Pro Ser
            115                 120                 125

Asp Pro Leu Glu Leu Val Val Thr Gly Phe T yr Asn Lys Pro Thr Leu
        130                 135                 140

Ser Ala Leu Pro Ser Pro Val Val Thr Ser G ly Glu Asn Val Thr Leu
145                 150                 155                 160
```

```
Gln Cys Gly Ser Arg Leu Arg Phe Asp Arg P he Ile Leu Thr Glu Glu
                165                 170                 175
Gly Asp His Lys Leu Ser Trp Thr Leu Asp S er Gln Leu Thr Pro Ser
            180                 185                 190
Gly Gln Phe Gln Ala Leu Phe Pro Val Gly P ro Val Thr Pro Ser His
        195                 200                 205
Arg Trp Met Leu Arg Cys Tyr Gly Ser Arg A rg His Ile Leu Gln Val
    210                 215                 220
Trp Ser Glu Pro Ser Asp Leu Leu Glu Ile P ro Val Ser Gly Ala Ala
225                 230                 235                 240
Asp Asn Leu Ser Pro Ser Gln Asn Lys Ser A sp Ser Gly Thr Ala Ser
                245                 250                 255
His Leu Gln Asp Tyr Ala Val Glu Asn Leu I le Arg Met Gly Met Ala
            260                 265                 270
Gly Leu Ile Leu Val Val Leu Gly Ile Leu I le Phe Gln Asp Trp His
        275                 280                 285
Ser Gln Arg Ser Pro Gln Ala Ala Ala Gly A rg
    290                 295

<210> SEQ ID NO 31
<211> LENGTH: 1007
<212> TYPE: DNA
<213> ORGANISM: human
<220> FEATURE:
<221> NAME/KEY: CDS
<222> LOCATION: (95)..(958)

<400> SEQUENCE: 31
caggtgtcag atgtgtctct gctgatctga gtctgcctgt ggcatggacc t gcatcttcc        60 ctgaagcatc tccagggctg aaaaatcact gacc atg gca cca tgg tct cat cca       115
                                     Met Ala Pro Trp Ser His Pro
                                       1               5 tct gca cag ctg cag cca gtg gga gga gac g cc gtg agc cct gcc ctc        163
Ser Ala Gln Leu Gln Pro Val Gly Gly Asp A la Val Ser Pro Ala Leu
         10                  15                  20 atg gtt ctg ctc tgc ctc ggg aac ctc tcc a aa gcc acc ctc tgg gct        211
Met Val Leu Leu Cys Leu Gly Asn Leu Ser L ys Ala Thr Leu Trp Ala
     25                  30                  35 gag cca ggc tct gtg atc agc cgg ggg aac t ct gtg acc atc cgg tgt        259
Glu Pro Gly Ser Val Ile Ser Arg Gly Asn S er Val Thr Ile Arg Cys
 40                  45                  50                  55 cag ggg acc ctg gag gcc cag gaa tac cgt c tg gtt aaa gag gga agc        307
Gln Gly Thr Leu Glu Ala Gln Glu Tyr Arg L eu Val Lys Glu Gly Ser
                 60                  65                  70 cca gaa ccc tgg gac aca cag aac cca ctg g ag ccc aag aac aag gcc        355
Pro Glu Pro Trp Asp Thr Gln Asn Pro Leu G lu Pro Lys Asn Lys Ala
             75                  80                  85 aga ttc tcc atc cca tcc atg aca gag cac c at gca ggg aga tac cgc        403
Arg Phe Ser Ile Pro Ser Met Thr Glu His H is Ala Gly Arg Tyr Arg
         90                  95                 100 tgt tac tac tac agc cct gca ggc tgg tca g ag ccc agc gac ccc ctg        451
Cys Tyr Tyr Tyr Ser Pro Ala Gly Trp Ser G lu Pro Ser Asp Pro Leu
    105                 110                 115 gag ctg gtg gtg aca gga ttc tac aac aaa c cc acc ctc tca gcc ctg        499
Glu Leu Val Val Thr Gly Phe Tyr Asn Lys P ro Thr Leu Ser Ala Leu
120                 125                 130                 135 ccc agt cct gtg gtg acc tca gga gag aac g tg acc ctc cag tgt ggc        547
Pro Ser Pro Val Val Thr Ser Gly Glu Asn V al Thr Leu Gln Cys Gly
                140                 145                 150
```

-continued

| | | |
|---|---|---|
| tca cgg ctg aga ttc gac agg ttc att ctg a ct gag gaa gga gac cac<br>Ser Arg Leu Arg Phe Asp Arg Phe Ile Leu T hr Glu Glu Gly Asp His<br>            155                        160                      165 | 595 |
| aag ctc tcc tgg acc ttg gac tca cag ctg a cc ccc agt ggg cag ttc<br>Lys Leu Ser Trp Thr Leu Asp Ser Gln Leu T hr Pro Ser Gly Gln Phe<br>            170                        175                      180 | 643 |
| cag gcc ctg ttc cct gtg ggc cct gtg acc c cc agc cac agg tgg atg<br>Gln Ala Leu Phe Pro Val Gly Pro Val Thr P ro Ser His Arg Trp Met<br>185                        190                        195 | 691 |
| ctc aga tgc tat ggc tct cgc agg cat atc c tg cag gta tgg tca gaa<br>Leu Arg Cys Tyr Gly Ser Arg Arg His Ile L eu Gln Val Trp Ser Glu<br>200                        205                        210                      215 | 739 |
| ccc agt gac ctc ctg gag att ccg gtc tca g ga gca gct gat aac ctc<br>Pro Ser Asp Leu Leu Glu Ile Pro Val Ser G ly Ala Ala Asp Asn Leu<br>            220                        225                      230 | 787 |
| agt ccg tca caa aac aag tct gac tct ggg a ct gcc tca cac ctt cag<br>Ser Pro Ser Gln Asn Lys Ser Asp Ser Gly T hr Ala Ser His Leu Gln<br>            235                        240                      245 | 835 |
| gat tac gca gta gag aat ctc atc cgc atg g gc atg gcc ggc ttg atc<br>Asp Tyr Ala Val Glu Asn Leu Ile Arg Met G ly Met Ala Gly Leu Ile<br>            250                        255                      260 | 883 |
| ctg gtg gtc ctt ggg att ctg ata ttt cag g at tgg cac agc cag aga<br>Leu Val Val Leu Gly Ile Leu Ile Phe Gln A sp Trp His Ser Gln Arg<br>265                        270                        275 | 931 |
| agc ccc caa gct gca gct gga agg tga acagaaga ga gaacaatgca<br>Ser Pro Gln Ala Ala Ala Gly Arg<br>280                        285 | 978 |
| ccattgaatg ctggagcctt ggaagcgaa | 1007 |

<210> SEQ ID NO 32
<211> LENGTH: 287
<212> TYPE: PRT
<213> ORGANISM: human

<400> SEQUENCE: 32

Met Ala Pro Trp Ser His Pro Ser Ala Gln L eu Gln Pro Val Gly Gly
 1               5                    10                  15

Asp Ala Val Ser Pro Ala Leu Met Val Leu L eu Cys Leu Gly Asn Leu
                20                    25                    30

Ser Lys Ala Thr Leu Trp Ala Glu Pro Gly S er Val Ile Ser Arg Gly
            35                    40                    45

Asn Ser Val Thr Ile Arg Cys Gln Gly Thr L eu Glu Ala Gln Glu Tyr
        50                    55                    60

Arg Leu Val Lys Glu Gly Ser Pro Glu Pro T rp Asp Thr Gln Asn Pro
65                        70                    75                    80

Leu Glu Pro Lys Asn Lys Ala Arg Phe Ser I le Pro Ser Met Thr Glu
                85                    90                    95

His His Ala Gly Arg Tyr Arg Cys Tyr Tyr T yr Ser Pro Ala Gly Trp
                100                    105                  110

Ser Glu Pro Ser Asp Pro Leu Glu Leu Val V al Thr Gly Phe Tyr Asn
            115                    120                  125

Lys Pro Thr Leu Ser Ala Leu Pro Ser Pro V al Val Thr Ser Gly Glu
        130                    135                    140

Asn Val Thr Leu Gln Cys Gly Ser Arg Leu A rg Phe Asp Arg Phe Ile
145                        150                    155                    160

Leu Thr Glu Glu Gly Asp His Lys Leu Ser T rp Thr Leu Asp Ser Gln
                165                    170                  175

-continued

```
Leu Thr Pro Ser Gly Gln Phe Gln Ala Leu Phe Pro Val Gly Pro Val
            180                 185                 190

Thr Pro Ser His Arg Trp Met Leu Arg Cys Tyr Gly Ser Arg Arg His
            195                 200                 205

Ile Leu Gln Val Trp Ser Glu Pro Ser Asp Leu Leu Glu Ile Pro Val
            210                 215                 220

Ser Gly Ala Ala Asp Asn Leu Ser Pro Ser Gln Asn Lys Ser Asp Ser
225                 230                 235                 240

Gly Thr Ala Ser His Leu Gln Asp Tyr Ala Val Glu Asn Leu Ile Arg
                    245                 250                 255

Met Gly Met Ala Gly Leu Ile Leu Val Val Leu Gly Ile Leu Ile Phe
                    260                 265                 270

Gln Asp Trp His Ser Gln Arg Ser Pro Gln Ala Ala Ala Gly Arg
                    275                 280                 285

<210> SEQ ID NO 33
<211> LENGTH: 956
<212> TYPE: DNA
<213> ORGANISM: human
<220> FEATURE:
<221> NAME/KEY: CDS
<222> LOCATION: (115)..(912)

<400> SEQUENCE: 33
ctcagcctgg gctacacagc caggtgtcag atgtgtctct gctgatctga g tctgcctgt      60 ggcatggacc tgcatcttcc ctgaagcatc tccagggctg aaaaatcact g acc atg      117
                                                        Met
                                                          1 gca cca tgg tct cat cca tct gca cag ctg c ag cca gtg gga gga gac      165
Ala Pro Trp Ser His Pro Ser Ala Gln Leu Gln Pro Val Gly Gly Asp
          5                  10                  15 gcc gtg agc cct gcc ctc atg gtt ctg ctc t gc ctc ggg ctg agt ctg      213
Ala Val Ser Pro Ala Leu Met Val Leu Leu Cys Leu Gly Leu Ser Leu
         20                  25                  30 ggc ccc agg acc cac gtg cag gca ggg aac c tc tcc aaa gcc acc ctc      261
Gly Pro Arg Thr His Val Gln Ala Gly Asn Leu Ser Lys Ala Thr Leu
     35                  40                  45 tgg gct gag cca ggc tct gtg atc agc cgg g gg aac tct gtg acc atc      309
Trp Ala Glu Pro Gly Ser Val Ile Ser Arg Gly Asn Ser Val Thr Ile
 50                  55                  60                  65 cgg tgt cag ggg acc ctg gag gcc cag gaa t ac cgt ctg gtt aaa gag      357
Arg Cys Gln Gly Thr Leu Glu Ala Gln Glu Tyr Arg Leu Val Lys Glu
                 70                  75                  80 gga agc cca gaa ccc tgg gac aca cag aac c ca ctg gag ccc aag aac      405
Gly Ser Pro Glu Pro Trp Asp Thr Gln Asn Pro Leu Glu Pro Lys Asn
             85                  90                  95 aag gcc aga ttc tcc atc cca tcc atg aca g ag cac cat gca ggg aga      453
Lys Ala Arg Phe Ser Ile Pro Ser Met Thr Glu His His Ala Gly Arg
         100                 105                 110 tac cgc tgt tac tac tac agc cct gca ggc t gg tca gag ccc agc gac      501
Tyr Arg Cys Tyr Tyr Tyr Ser Pro Ala Gly Trp Ser Glu Pro Ser Asp
     115                 120                 125 ccc ctg gag ctg gtg gtg aca gga ttc tac a ac aaa ccc acc ctc tca      549
Pro Leu Glu Leu Val Val Thr Gly Phe Tyr Asn Lys Pro Thr Leu Ser
130                 135                 140                 145 gcc ctg ccc agt cct gtg gtg acc tca gga g ag aac gtg acc ctc cag      597
Ala Leu Pro Ser Pro Val Val Thr Ser Gly Glu Asn Val Thr Leu Gln
                 150                 155                 160
```

```
tgt ggc tca cgg ctg aga ttc gac agg ttc a tt ctg act gag gaa gga        645
Cys Gly Ser Arg Leu Arg Phe Asp Arg Phe I le Leu Thr Glu Glu Gly
            165                 170                 175 gac cac aag ctc tcc tgg acc ttg gac tca c ag ctg acc ccc agt ggg        693
Asp His Lys Leu Ser Trp Thr Leu Asp Ser G ln Leu Thr Pro Ser Gly
            180                 185                 190 cag ttc cag gcc ctg ttc cct gtg ggc cct g tg acc ccc agc cac agg        741
Gln Phe Gln Ala Leu Phe Pro Val Gly Pro V al Thr Pro Ser His Arg
    195                 200                 205 tgg atg ctc aga tgc tat ggc tct agg c at atc ctg cag gta tgg           789
Trp Met Leu Arg Cys Tyr Gly Ser Arg Arg H is Ile Leu Gln Val Trp
210             215                 220                 225 tca gaa ccc agt gac ctc ctg gag att ccg g tc tca ggt gag gaa gcc        837
Ser Glu Pro Ser Asp Leu Leu Glu Ile Pro V al Ser Gly Glu Glu Ala
                230                 235                 240 aca gtc ttc tct agt aca att cag gga agc c ag aca ggt tgt gga gag       885
Thr Val Phe Ser Ser Thr Ile Gln Gly Ser G ln Thr Gly Cys Gly Glu
                245                 250                 255 ctt tac agg cag ggc agc ccc tgc taa gaaagaca aa aaggggaagg             932
Leu Tyr Arg Gln Gly Ser Pro Cys
        260                 265 agaacacaga aatcctaggg acac                                             956

<210> SEQ ID NO 34
<211> LENGTH: 265
<212> TYPE: PRT
<213> ORGANISM: human

<400> SEQUENCE: 34

Met Ala Pro Trp Ser His Pro Ser Ala Gln L eu Gln Pro Val Gly Gly
1               5                   10                  15

Asp Ala Val Ser Pro Ala Leu Met Val Leu L eu Cys Leu Gly Leu Ser
                20                  25                  30

Leu Gly Pro Arg Thr His Val Gln Ala Gly A sn Leu Ser Lys Ala Thr
            35                  40                  45

Leu Trp Ala Glu Pro Gly Ser Val Ile Ser A rg Gly Asn Ser Val Thr
        50                  55                  60

Ile Arg Cys Gln Gly Thr Leu Glu Ala Gln G lu Tyr Arg Leu Val Lys
65                  70                  75                  80

Glu Gly Ser Pro Glu Pro Trp Asp Thr Gln A sn Pro Leu Glu Pro Lys
                85                  90                  95

Asn Lys Ala Arg Phe Ser Ile Pro Ser Met T hr Glu His His Ala Gly
            100                 105                 110

Arg Tyr Arg Cys Tyr Tyr Tyr Ser Pro Ala G ly Trp Ser Glu Pro Ser
        115                 120                 125

Asp Pro Leu Glu Leu Val Val Thr Gly Phe T yr Asn Lys Pro Thr Leu
    130                 135                 140

Ser Ala Leu Pro Ser Pro Val Val Thr Ser G ly Glu Asn Val Thr Leu
145                 150                 155                 160

Gln Cys Gly Ser Arg Leu Arg Phe Asp Arg P he Ile Leu Thr Glu Glu
                165                 170                 175

Gly Asp His Lys Leu Ser Trp Thr Leu Asp S er Gln Leu Thr Pro Ser
            180                 185                 190

Gly Gln Phe Gln Ala Leu Phe Pro Val Gly P ro Val Thr Pro Ser His
        195                 200                 205

Arg Trp Met Leu Arg Cys Tyr Gly Ser Arg A rg His Ile Leu Gln Val
    210                 215                 220
```

```
Trp Ser Glu Pro Ser Asp Leu Leu Glu Ile Pro Val Ser Gly Glu Glu
225                 230                 235                 240

Ala Thr Val Phe Ser Ser Thr Ile Gln Gly Ser Gln Thr Gly Cys Gly
                245                 250                 255

Glu Leu Tyr Arg Gln Gly Ser Pro Cys
                260                 265

<210> SEQ ID NO 35
<211> LENGTH: 997
<212> TYPE: DNA
<213> ORGANISM: human
<220> FEATURE:
<221> NAME/KEY: CDS
<222> LOCATION: (73)..(834)

<400> SEQUENCE: 35
tgatctgagt ctgcctgtgg catggacctg catcttccct gaagcatctc c agggctgaa    60 aaatcactga cc atg gca cca tgg tct cat cca tc t gca cag ctg cag cca   111
              Met Ala Pro Trp Ser His Pro Ser Ala Gln Leu Gln Pro
                1               5                  10 gtg gga gga gac gcc gtg agc cct gcc ctc a tg gtt ctg ctc tgc ctc     159
Val Gly Gly Asp Ala Val Ser Pro Ala Leu Met Val Leu Leu Cys Leu
 15              20                  25 ggg aac ctc tcc aaa gcc acc ctc tgg gct g ag cca ggc tct gtg atc     207
Gly Asn Leu Ser Lys Ala Thr Leu Trp Ala Glu Pro Gly Ser Val Ile
 30              35                  40                  45 agc cgg ggg aac tct gtg acc atc cgg tgt c ag ggg acc ctg gag gcc     255
Ser Arg Gly Asn Ser Val Thr Ile Arg Cys Gln Gly Thr Leu Glu Ala
                 50                  55                  60 cag gaa tac cgt ctg gtt aaa gag gga agc c ca gaa ccc tgg gac aca     303
Gln Glu Tyr Arg Leu Val Lys Glu Gly Ser Pro Glu Pro Trp Asp Thr
             65                  70                  75 cag aac cca ctg gag ccc aag aac aag gcc a ga ttc tcc atc cca tcc     351
Gln Asn Pro Leu Glu Pro Lys Asn Lys Ala Arg Phe Ser Ile Pro Ser
         80                  85                  90 atg aca gag cac cat gca ggg aga tac cgc t gt tac tac tac agc cct     399
Met Thr Glu His His Ala Gly Arg Tyr Arg Cys Tyr Tyr Tyr Ser Pro
     95                 100                 105 gca ggc tgg tca gag ccc agc gac ccc ctg g ag ctg gtg gtg aca gga    447
Ala Gly Trp Ser Glu Pro Ser Asp Pro Leu Glu Leu Val Val Thr Gly
110                 115                 120                 125 ttc tac aac aaa ccc acc ctc tca gcc ctg c cc agt cct gtg gtg acc    495
Phe Tyr Asn Lys Pro Thr Leu Ser Ala Leu Pro Ser Pro Val Val Thr
                130                 135                 140 tca gga gag aac gtg acc ctc cag tgt ggc t ca cgg ctg aga ttc gac    543
Ser Gly Glu Asn Val Thr Leu Gln Cys Gly Ser Arg Leu Arg Phe Asp
            145                 150                 155 agg ttc att ctg act gag gaa gga gac cac a ag ctc tcc tgg acc ttg    591
Arg Phe Ile Leu Thr Glu Glu Gly Asp His Lys Leu Ser Trp Thr Leu
        160                 165                 170 gac tca cag ctg acc ccc agt ggg cag ttc c ag gcc ctg ttc cct gtg    639
Asp Ser Gln Leu Thr Pro Ser Gly Gln Phe Gln Ala Leu Phe Pro Val
    175                 180                 185 ggc cct gtg acc ccc agc cac agg tgg atg c tc aga tgc tat ggc tct    687
Gly Pro Val Thr Pro Ser His Arg Trp Met Leu Arg Cys Tyr Gly Ser
190                 195                 200                 205 cgc agg cat atc ctg cag gta tgg tca gaa c cc agt gac ctc ctg gag    735
Arg Arg His Ile Leu Gln Val Trp Ser Glu Pro Ser Asp Leu Leu Glu
                210                 215                 220
```

```
att ccg gtc tca ggt gag gaa gcc aca gtc t tc tct agt aca att cag    783
Ile Pro Val Ser Gly Glu Glu Ala Thr Val P he Ser Ser Thr Ile Gln
        225                 230                 235 gga agc cag aca ggt tgt gga gag ctt tac a gg cag ggc agc ccc tgc    831
Gly Ser Gln Thr Gly Cys Gly Glu Leu Tyr A rg Gln Gly Ser Pro Cys
        240                 245                 250 taa gaaagacaaa aaggggaagg agaacacaga aatcctaggg acacaaat tc         884 agggtgagga aacaaagca aggctgggc acagtggctc acacgtgtaa t ctcagcact    944 ttgggaggcc gaggcaggtg gatcacctga tgtcaggagt tcaagaccag c ct         997
```

<210> SEQ ID NO 36
<211> LENGTH: 253
<212> TYPE: PRT
<213> ORGANISM: human

<400> SEQUENCE: 36

```
Met Ala Pro Trp Ser His Pro Ser Ala Gln L eu Gln Pro Val Gly Gly
 1               5                  10                  15

Asp Ala Val Ser Pro Ala Leu Met Val Leu L eu Cys Leu Gly Asn Leu
            20                  25                  30

Ser Lys Ala Thr Leu Trp Ala Glu Pro Gly S er Val Ile Ser Arg Gly
        35                  40                  45

Asn Ser Val Thr Ile Arg Cys Gln Gly Thr L eu Glu Ala Gln Glu Tyr
    50                  55                  60

Arg Leu Val Lys Glu Gly Ser Pro Glu Pro T rp Asp Thr Gln Asn Pro
65                  70                  75                  80

Leu Glu Pro Lys Asn Lys Ala Arg Phe Ser I le Pro Ser Met Thr Glu
                85                  90                  95

His His Ala Gly Arg Tyr Arg Cys Tyr Tyr T yr Ser Pro Ala Gly Trp
            100                 105                 110

Ser Glu Pro Ser Asp Pro Leu Glu Leu Val V al Thr Gly Phe Tyr Asn
        115                 120                 125

Lys Pro Thr Leu Ser Ala Leu Pro Ser Pro V al Val Thr Ser Gly Glu
    130                 135                 140

Asn Val Thr Leu Gln Cys Gly Ser Arg Leu A rg Phe Asp Arg Phe Ile
145                 150                 155                 160

Leu Thr Glu Glu Gly Asp His Lys Leu Ser T rp Thr Leu Asp Ser Gln
                165                 170                 175

Leu Thr Pro Ser Gly Gln Phe Gln Ala Leu P he Pro Val Gly Pro Val
            180                 185                 190

Thr Pro Ser His Arg Trp Met Leu Arg Cys T yr Gly Ser Arg Arg His
        195                 200                 205

Ile Leu Gln Val Trp Ser Glu Pro Ser Asp L eu Leu Glu Ile Pro Val
    210                 215                 220

Ser Gly Glu Glu Ala Thr Val Phe Ser Ser T hr Ile Gln Gly Ser Gln
225                 230                 235                 240

Thr Gly Cys Gly Glu Leu Tyr Arg Gln Gly S er Pro Cys
                245                 250
```

<210> SEQ ID NO 37
<211> LENGTH: 1451
<212> TYPE: DNA
<213> ORGANISM: human
<220> FEATURE:
<221> NAME/KEY: CDS
<222> LOCATION: (1)..(1347)

```
<400> SEQUENCE: 37 ccc aag ccc acc ctc tgg gct aag cca ggc t ct gtg atc agc tgg aga        48
Pro Lys Pro Thr Leu Trp Ala Lys Pro Gly S er Val Ile Ser Trp Arg
 1               5                  10                  15 agc ccc atg acc atg tgg tgt cag ggg acc c tg gaa gcc cag gag tac        96
Ser Pro Met Thr Met Trp Cys Gln Gly Thr L eu Glu Ala Gln Glu Tyr
             20                  25                  30 cat ctg tat aaa gag gga agc aca gag ccc t gg gac aga acg aat cca       144
His Leu Tyr Lys Glu Gly Ser Thr Glu Pro T rp Asp Arg Thr Asn Pro
         35                  40                  45 ctg gag acc agg aac aag gcc aga tac tcc a tc cca tcc atg aca cag       192
Leu Glu Thr Arg Asn Lys Ala Arg Tyr Ser I le Pro Ser Met Thr Gln
     50                  55                  60 cac cat gca gtg aga tat cag tgt tac tat c tc agc cct gca ggc tgg       240
His His Ala Val Arg Tyr Gln Cys Tyr Tyr L eu Ser Pro Ala Gly Trp
 65                  70                  75                  80 tca gag ccc agt gac ccc ctg gag ctg gtg a tg aca gga ttc tac agc       288
Ser Glu Pro Ser Asp Pro Leu Glu Leu Val M et Thr Gly Phe Tyr Ser
                 85                  90                  95 aaa ccc acc ctc tca gcc ctg ccc agc cct g tg gtg gcc tca ggg ggg       336
Lys Pro Thr Leu Ser Ala Leu Pro Ser Pro V al Val Ala Ser Gly Gly
             100                 105                 110 aaa gtg acc ctc cga tgt ggc tca cag aag g ga tat cac cat ttt gtt       384
Lys Val Thr Leu Arg Cys Gly Ser Gln Lys G ly Tyr His His Phe Val
         115                 120                 125 ctg atg aag gaa gga gaa cac cag ctc ccc c gg acc ctg gac tca cag       432
Leu Met Lys Glu Gly Glu His Gln Leu Pro A rg Thr Leu Asp Ser Gln
     130                 135                 140 cag ctc cac agt ggg ggg ttc cag gcc ctg t tc cct gtg ggc ccc gtg       480
Gln Leu His Ser Gly Gly Phe Gln Ala Leu P he Pro Val Gly Pro Val
145                 150                 155                 160 acc ccc agc cac agg tgg agg ttc aca tgc t at tac tat tat atg aac       528
Thr Pro Ser His Arg Trp Arg Phe Thr Cys T yr Tyr Tyr Tyr Met Asn
                 165                 170                 175 acc ccc cag gtg tgg tcc cac ccc agt gac c cc ctg gag att ctg ccc       576
Thr Pro Gln Val Trp Ser His Pro Ser Asp P ro Leu Glu Ile Leu Pro
             180                 185                 190 tca gga cag agc tct ccc cct gtc ctg gcc c ct gga gag acc ctg acc       624
Ser Gly Gln Ser Ser Pro Pro Val Leu Ala P ro Gly Glu Thr Leu Thr
         195                 200                 205 ctc cag tgt ggc tct gat gtc ggc tac gac a ga ttc act ctg tac aag       672
Leu Gln Cys Gly Ser Asp Val Gly Tyr Asp A rg Phe Thr Leu Tyr Lys
     210                 215                 220 gag ggg gaa tgt gac ttc ctc cag cgc cct g gc cag cag ccc cag gct       720
Glu Gly Glu Cys Asp Phe Leu Gln Arg Pro G ly Gln Gln Pro Gln Ala
225                 230                 235                 240 ggg ctc tcc cag gcc aac ttc acc ctg ggc c ct gtg agg ggc tcc cac       768
Gly Leu Ser Gln Ala Asn Phe Thr Leu Gly P ro Val Arg Gly Ser His
                 245                 250                 255 ggg ggc cag tac aga tgc tcc ggt gca cac a ac ctc tcc tcc gag tgg       816
Gly Gly Gln Tyr Arg Cys Ser Gly Ala His A sn Leu Ser Ser Glu Trp
             260                 265                 270 tcg gcc ccc agt gac ccc ctg gac atc ctg a tc gca gga cag atc cct       864
Ser Ala Pro Ser Asp Pro Leu Asp Ile Leu I le Ala Gly Gln Ile Pro
         275                 280                 285 ggc aga ccc tcc ctc tcg gtg cag ttg tgg c cc aca gtg gcc tca gga       912
Gly Arg Pro Ser Leu Ser Val Gln Leu Trp P ro Thr Val Ala Ser Gly
     290                 295                 300
```

```
gag aac gtg acc ctg ctg tgt caa tca caa g ag tgg atg cac act ttc       960
Glu Asn Val Thr Leu Leu Cys Gln Ser Gln G lu Trp Met His Thr Phe
305                 310                 315                 320 ctt ctg acc aag gag ggg gca gcc cat ccc c tg ctg tgt ctg aga tca      1008
Leu Leu Thr Lys Glu Gly Ala Ala His Pro L eu Leu Cys Leu Arg Ser
                325                 330                 335 aag tac gga gct cat aag tac cag gct gaa t tc ccc atg agt cct gtg     1056
Lys Tyr Gly Ala His Lys Tyr Gln Ala Glu P he Pro Met Ser Pro Val
            340                 345                 350 acc tca gcc cac acg ggg acc tac agg tgc t ac ggc tca ctc agc tcc     1104
Thr Ser Ala His Thr Gly Thr Tyr Arg Cys T yr Gly Ser Leu Ser Ser
            355                 360                 365 gac ccc tac ctg ctg tct cac ccc agt ggc c cc gtg gag ctc gtg gtc     1152
Asp Pro Tyr Leu Leu Ser His Pro Ser Gly P ro Val Glu Leu Val Val
370                 375                 380 tca gcc tca cac ctt cag gat tac gca gtg g ag aat ctc atc cac atg     1200
Ser Ala Ser His Leu Gln Asp Tyr Ala Val G lu Asn Leu Ile His Met
385                 390                 395                 400 ggc gtg gct ggc ttg atc ctg gtg gtc ctc g gg att ctg tca ttt gag     1248
Gly Val Ala Gly Leu Ile Leu Val Val Leu G ly Ile Leu Ser Phe Glu
                405                 410                 415 gct tgg cac agc cag aga agc ttc cca aga t gc agc cgg gag gtg aac     1296
Ala Trp His Ser Gln Arg Ser Phe Pro Arg C ys Ser Arg Glu Val Asn
            420                 425                 430 agc aga gag gat aat gta ctt tat aga gtc g tg aag cct cag gaa cag     1344
Ser Arg Glu Asp Asn Val Leu Tyr Arg Val V al Lys Pro Gln Glu Gln
            435                 440                 445 atc tgatgatccc aggaggtgct ggaagaaaat ctagggccga tgctatct gg          1397
Ile actgtctgct ggtcatttcc agaggaagga atcaatgtcc gagtgcaggg a cat         1451

<210> SEQ ID NO 38
<211> LENGTH: 449
<212> TYPE: PRT
<213> ORGANISM: human

<400> SEQUENCE: 38

Pro Lys Pro Thr Leu Trp Ala Lys Pro Gly S er Val Ile Ser Trp Arg
 1               5                   10                  15

Ser Pro Met Thr Met Trp Cys Gln Gly Thr L eu Glu Ala Gln Glu Tyr
                20                  25                  30

His Leu Tyr Lys Glu Gly Ser Thr Glu Pro T rp Asp Arg Thr Asn Pro
            35                  40                  45

Leu Glu Thr Arg Asn Lys Ala Arg Tyr Ser I le Pro Ser Met Thr Gln
        50                  55                  60

His His Ala Val Arg Tyr Gln Cys Tyr Tyr L eu Ser Pro Ala Gly Trp
 65                 70                  75                  80

Ser Glu Pro Ser Asp Pro Leu Glu Leu Val M et Thr Gly Phe Tyr Ser
                85                  90                  95

Lys Pro Thr Leu Ser Ala Leu Pro Ser Pro V al Val Ala Ser Gly Gly
            100                 105                 110

Lys Val Thr Leu Arg Cys Gly Ser Gln Lys G ly Tyr His His Phe Val
        115                 120                 125

Leu Met Lys Glu Gly Glu His Gln Leu Pro A rg Thr Leu Asp Ser Gln
    130                 135                 140

Gln Leu His Ser Gly Gly Phe Gln Ala Leu P he Pro Val Gly Pro Val
145                 150                 155                 160
```

```
Thr Pro Ser His Arg Trp Arg Phe Thr Cys Tyr Tyr Tyr Met Asn
            165                 170                 175

Thr Pro Gln Val Trp Ser His Pro Ser Asp Pro Leu Glu Ile Leu Pro
            180                 185                 190

Ser Gly Gln Ser Ser Pro Pro Val Leu Ala Pro Gly Glu Thr Leu Thr
            195                 200                 205

Leu Gln Cys Gly Ser Asp Val Gly Tyr Asp Arg Phe Thr Leu Tyr Lys
        210                 215                 220

Glu Gly Glu Cys Asp Phe Leu Gln Arg Pro Gly Gln Gln Pro Gln Ala
225                 230                 235                 240

Gly Leu Ser Gln Ala Asn Phe Thr Leu Gly Pro Val Arg Gly Ser His
            245                 250                 255

Gly Gly Gln Tyr Arg Cys Ser Gly Ala His Asn Leu Ser Ser Glu Trp
            260                 265                 270

Ser Ala Pro Ser Asp Pro Leu Asp Ile Leu Ile Ala Gly Gln Ile Pro
            275                 280                 285

Gly Arg Pro Ser Leu Ser Val Gln Leu Trp Pro Thr Val Ala Ser Gly
            290                 295                 300

Glu Asn Val Thr Leu Leu Cys Gln Ser Gln Glu Trp Met His Thr Phe
305                 310                 315                 320

Leu Leu Thr Lys Glu Gly Ala Ala His Pro Leu Leu Cys Leu Arg Ser
            325                 330                 335

Lys Tyr Gly Ala His Lys Tyr Gln Ala Glu Phe Pro Met Ser Pro Val
            340                 345                 350

Thr Ser Ala His Thr Gly Thr Tyr Arg Cys Tyr Gly Ser Leu Ser Ser
            355                 360                 365

Asp Pro Tyr Leu Leu Ser His Pro Ser Gly Pro Val Glu Leu Val Val
        370                 375                 380

Ser Ala Ser His Leu Gln Asp Tyr Ala Val Glu Asn Leu Ile His Met
385                 390                 395                 400

Gly Val Ala Gly Leu Ile Leu Val Val Leu Gly Ile Leu Ser Phe Glu
            405                 410                 415

Ala Trp His Ser Gln Arg Ser Phe Pro Arg Cys Ser Arg Glu Val Asn
            420                 425                 430

Ser Arg Glu Asp Asn Val Leu Tyr Arg Val Val Lys Pro Gln Glu Gln
        435                 440                 445

Ile

<210> SEQ ID NO 39
<211> LENGTH: 8
<212> TYPE: PRT
<213> ORGANISM: human

<400> SEQUENCE: 39

Asp Tyr Lys Asp Asp Asp Asp Lys
  1               5
```